US009144558B2

(12) United States Patent
Cohen et al.

(10) Patent No.: US 9,144,558 B2
(45) Date of Patent: *Sep. 29, 2015

(54) BACLOFEN AND ACAMPROSATE BASED THERAPY OF NEUROLOGICAL DISORDERS

(71) Applicant: PHARNEXT, Issy les Moulineaux (FR)

(72) Inventors: Daniel Cohen, Le Vesinet (FR); Ilya Chumakov, Vaux le Penil (FR); Serguei Nabirochkin, Chatenay Malabry (FR); Emmanuel Vial, Paris (FR); Mickael Guedj, Paris (FR)

(73) Assignee: PHARNEXT, Issy les Moulineaux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/479,614

(22) Filed: Sep. 8, 2014

(65) Prior Publication Data

US 2014/0378440 A1 Dec. 25, 2014

Related U.S. Application Data

(63) Continuation-in-part of application No. 13/691,981, filed on Dec. 3, 2012, now Pat. No. 8,865,769, which is a continuation of application No. PCT/EP2012/053570, filed on Mar. 1, 2012.

(60) Provisional application No. 61/468,658, filed on Mar. 29, 2011, provisional application No. 61/493,606, filed on Jun. 6, 2011.

(30) Foreign Application Priority Data

Mar. 1, 2011 (EP) ..................................... 11305217
Jun. 6, 2011 (EP) ..................................... 11305687

(51) Int. Cl.
| | |
|---|---|
| A61K 31/255 | (2006.01) |
| A61K 31/205 | (2006.01) |
| A61K 31/19 | (2006.01) |
| A61K 31/197 | (2006.01) |
| A61K 31/445 | (2006.01) |
| A61K 45/06 | (2006.01) |
| A61K 31/185 | (2006.01) |
| A61K 31/13 | (2006.01) |
| A61K 31/27 | (2006.01) |
| A61K 31/55 | (2006.01) |

(52) U.S. Cl.
CPC ............... *A61K 31/197* (2013.01); *A61K 31/13* (2013.01); *A61K 31/185* (2013.01); *A61K 31/27* (2013.01); *A61K 31/445* (2013.01); *A61K 31/55* (2013.01); *A61K 45/06* (2013.01)

(58) Field of Classification Search
CPC . A61K 31/197; A61K 31/445; A61K 31/185; A61K 31/13; A61K 31/27; A61K 31/55
USPC ............ 514/171, 567, 255.01, 380, 347, 317, 514/247, 378, 319, 479
See application file for complete search history.

(56) References Cited

U.S. PATENT DOCUMENTS

| 6,391,922 B1 | 5/2002 | Fogel |
|---|---|---|
| 8,741,886 B2 | 6/2014 | Cohen et al. |
| 2001/0004640 A1 | 6/2001 | Inada et al. |
| 2001/0023246 A1 | 9/2001 | Barritault et al. |
| 2004/0102525 A1 | 5/2004 | Kozachuk |
| 2008/0188510 A1 | 8/2008 | Yoshino |
| 2009/0069419 A1 | 3/2009 | Jandeleit et al. |
| 2009/0197958 A1 | 8/2009 | Sastry et al. |
| 2011/0230659 A1 | 9/2011 | Tsukamoto et al. |
| 2012/0270836 A1 | 10/2012 | Cohen et al. |

FOREIGN PATENT DOCUMENTS

| EP | 1 563 846 | 8/2005 |
|---|---|---|
| EP | 1 837 034 | 9/2007 |
| WO | WO 01/58476 | 8/2001 |
| WO | WO 03/007993 | 1/2003 |
| WO | WO 03/080068 | 10/2003 |
| WO | WO 2007/053596 | 5/2007 |
| WO | WO 2008/006070 | 1/2008 |
| WO | WO 2008/143361 | 11/2008 |
| WO | WO 2009/133128 | 11/2009 |
| WO | WO 2009/133141 | 11/2009 |
| WO | WO 2009/133142 | 11/2009 |

(Continued)

OTHER PUBLICATIONS

Lipton, S.A. "Failures and Successes of NMDA Receptor Antagonists: Molecular Basis for the Use of Open-Channel Blockers like Memantine in the Treatment of Acute and Chronic Neurologic Insults" *NeuroRx, The Journal of American Society for Experimental NeuroTherapeutics*, Jan. 2004, pp. 101-110, vol. 1.

Sanger, D.J. et al. "Effects of NMDA receptor antagonists and sigma ligands on the acquisition of conditioned fear in mice" *Psychopharmacology*, 1991, pp. 27-34, vol. 104.

Jentsch, J.D. et al. "A low dose of the alpha$_2$ agonist clonidine ameliorates the visual attention and spatial working memory deficits produced by phencyclidine administration to rats" *Psychopharmacology*, 2004, pp. 76-83, vol. 175.

Olney, J.W. et al. "Pathological Changes Induced in Cerebrocortical Neurons by Phencyclidine and Related Drugs" *Science*, Jun. 16, 1989, pp. 1360-1362, vol. 244, No. 4910.

(Continued)

*Primary Examiner* — Jennifer M Kim
(74) *Attorney, Agent, or Firm* — Saliwanchik, Lloyd & Eisenschenk

(57) ABSTRACT

The present invention relates to combinations and methods for the treatment of neurological disorders related to glutamate excitotoxicity and Amyloid β toxicity. More specifically, the present invention relates to novel combinatorial therapies of Alzheimer's disease, Alzheimer's disease related disorders, amyotrophic lateral sclerosis, multiple sclerosis, Parkinson's disease, Huntington's disease, neuropathic pain, alcoholic neuropathy, alcoholism or alcohol withdrawal, or spinal cord injury, based on baclofen and acamprosate combination.

42 Claims, 26 Drawing Sheets

(56) References Cited

FOREIGN PATENT DOCUMENTS

| WO | WO 2010/061931 | 6/2010 |
|---|---|---|
| WO | WO 2011/054759 | 5/2011 |

OTHER PUBLICATIONS

Davis, S.M. et al. "Selfotel in Acute Ischemic Stroke: Possible Neurotoxic Effects of an NMDA Antagonist" *Stroke*, 2000, pp. 347-354, vol. 31.
Lengyel, C. et al. "Effect of a neuroprotective drug, eliprodil on cardiac repolarisation: importance of the decreased repolarisation reserve in the development of proarrhythmic risk" *British Journal of Pharmacology*, 2004, pp. 152-158, vol. 143.
Schneider, U. et al. "Effects of Acamprosate on Memory in Healthy Young Subjects" *Journal of Studies on Alcohol*, Mar. 1999, pp. 172-175, vol. 60.
Van Der Staay, F.J. et al. "Effects of the cognition impairer MK-801 on learning and memory in mice and rats" *Behavioural Brain Research* 2011, pp. 215-229, vol. 220.
Roberts, M. et al. "NMDA Receptor Antagonists Impair Memory for Nonspatial, Socially Transmitted Food Preference" *Behavioral Neuroscience*, 2002, pp. 1059-1069, vol. 116, No. 6.
Krystal, J.H. "Subanesthetic Effects of the Noncompetitive NMDA Antagonist, Ketamine, in Humans" *Arch. Gen. Psychiatry*, Mar. 1994, pp. 199-214, vol. 51.
Subhan, Z. et al. "Psychopharmacological Effects of Vinpocetine in Normal Healthy Volunteers" *Eur. J. Clin. Pharmacol*, 1985, pp. 567-571, vol. 28.
Thal, L.J. et al. "The Safety and Lack of Efficacy of Vinpocetine in Alzheimer's Disease" *J. Am. Geriatr. Soc.*, Jun. 1989, pp. 515-520, vol. 37, No. 6.
Sandyk, R. et al. "Baclofen-Induced Memory Impairment" *Clinical Neuropharmacology*, 1985, pp. 294-295, vol. 8, No. 3.
Lee, B.Y. et al. "Chronic stimulation of $GABA_A$ receptor with muscimol reduces amyloid β protein (25-35)-induced neurotoxicity in cultured rat cortical cells" *Neuroscience Research*, 2005, pp. 347-356, vol. 52.
Marcade, M. et al. "Etazolate, a neuroprotective drug linking $GABA_A$ receptor pharmacology to amyloid precursor protein processing" *Journal of Neurochemistry*, 2008, pp. 392-404, vol. 106.
Maubach, K. "$GABA_A$ Receptor Subtype Selective Cognition Enhancers" *Current Drug Targets. CNS & Neurological Disorders*, 2003, pp. 233-239, vol. 2.
2014 Alzheimer's disease facts and figures, *Alzheimer's & Dementia*, 2014, pp. e47-e92, vol. 10.
PHRMA, "Researching Alzheimer's Medicines : Setbacks and Stepping Stones" 2012, pp. 1-20.
Maria, B. "Renewed focus on dementia checked by drug challenges" *Chemistry World*, 2014, pp. 1-3.
Chumakov, I. et al. "Combining two repurposed drugs as a promising approach for Alzheimer's disease therapy" *Scientific Reports*, 2015, pp. 1-12, vol. 5.
Scart-Gres, C. et al. "OC30—First Evidence of PXT00864 Effect in the Treatment of Mild AD: Results on 30 Patients From the PLEODIAL I study" *J. Prev. Alz. Dis.*, Summary of Oral Communication at the 7th Conference Clinical Trials on Alzheimer's Disease, 2014, pp. 232-233, vol. 1.
Hama, A. et al. "Synergistic interaction between intrathecal gamma-aminobutyrate (GABA) receptor agonists and an N-methyl-D-aspartate (NMDA) receptor antagonist in rats with neuropathic spinal cord injury pain" *Society for Neuroscience Abstract Viewer and in Itinerary Planner*, 2010, p. 1, vol. 40.
Lyden, P.D. et al. "Combination therapy protects ischemic brain in rats. A glutamate antagonist plus a gamma-aminobutyric acid agonist" *Stroke*, 1994, pp. 189-196, vol. 25.
Costa, C. et al. "Coactivation of $GABA_A$ and $GABA_B$ Receptor Results in Neuroprotection During in Vitro Ischemia" *Stroke*, Jan. 15, 2004, pp. 596-600, vol. 35.
Zhou, C. et al. "Neuroprotection of Y-Aminobutyric Acid Receptor Agonists Via Enhancing Neuronal Nitric Oxide Synthase (Ser847) Phosphorylation Through Increased neuronal Nitric Oxide Synthase and PSD95 Interaction and Inhibited Protein Phosphatase Activity in Cerebral Ischemia" *Journal of Neuroscience Research*, 2008, pp. 2973-2983, vol. 86.
Louzada, P. R. et al. "Taurine prevents the neurotoxicity of β-amyloid and glutamate receptor agonists: activation of GABA receptors and possible implications for Alzheimer's disease and other neurological disorders" *The FASEB Journal*, Mar. 2004, vol. 18.
Engelhard, K. et al. "Der neuroprotektive Einfluss des Glutamat-Antagonisten Acamprosat nach experimenteller zerebraler Ischämie" *Der Anaesthesist*, Sep. 22, 2000, pp. 816, 818, and 820, vol. 49, No. 9.
Akan P. et al. "Pregnenolone protects the PC-12 cell line against amyloid beta peptide toxicity but its sulfate ester does not" *Chemico-Biological Interactions*, 2009, pp. 65-70, vol. 177, No. 1, XP-002613421.
Andrieu, S. et al. "Association of Alzheimer's Disease Onset With Ginkgo Biloba and Other Symptomatic Cognitive Treatments in a Population of Women Aged 75 Years and Older From the EPIDOS Study" *Journal of Gerontology: Medical Sciences*, Apr. 2003, pp. 372-377, vol. 58A, No. 4, XP-009144763.
Aplin, A. C. et al. "Vascular regression and survival are differentially regulated by MT1-MMP and TIMPs in the aortic ring model of angiogenesis" *Am. J. Physiol Cell Physiol*, Aug. 2009, pp. C471-C480, vol. 297, No. 2, XP-002613424.
Dobrek, L. et al. "Future Potential Indications for Pharmacotherapy Using Renin-Angiotensin-Aldosterone System Inhibitory Agents" *Adv. Clin. Exp. Med.*, May 2010, pp. 389-398, vol. 19, No. 3, XP-009144580.
Finsterer, J. et al. "Neurotoxocarosis" *Rev. Inst. Med. Trop. S. Paulo*, pp. 279-287, Sep.-Oct. 2007, vol. 49, No. 5, XP-002623261.
Kakinuma, Y. et al. "Donepezil, an acetylcholinesterase inhibitor against Alzheimer's dementia, promotes angiogenesis in an ischemic hindlimb model" *Journal of Molecular and Cellular Cardiology*, Apr. 2010, pp. 680-693, vol. 48, No. 4, XP-26949580.
Klein, H.E. et al. "Calcium antagonists in dementias. Assessment of the therapeutic efficacy" *Munchener Medizinische Wochenschrift*, 1995, pp. 38, 41-43, vol. 137, No. 47, XP-001525484.
Lee, S.T. et al. "Reduced circulating angiogenic cells in Alzheimer disease" *Neurology*, May 1, 2009, pp. 1858-1863, vol. 72, No. 21, XP-002610857.
Lu, Y. et al. "Neuroprotective activity and evaluation of Hsp90 inhibitors in an immortalized neuronal cell line" *Bioorganic & Medicinal Chemistry*, Feb. 2009, pp. 1709-1715, vol. 17, No. 4, XP-002613422.
Parnetti, L. et al. "Vascular Dementia Italian Sulodexide Study (VA. D.I.S.S.) Clinical and Biological Results" *Thrombosis Research*, pp. 225-233, vol. 87, No. 2, (1997).
Polizopoulou, Z. S. et al. "Evaluation of a Proposed Therapeutic Protocol in 12 Dogs with Tentative Degenerative Myelopathy" *Act Veterinaria Hungarica*, pp. 293-301, Sep. 2008, vol. 56, No. 3, XP-009142152.
Pooler, A. M. et al. "The 3-hydroxy-3-methylglutaryl co-enzyme A reductase inhibitor pravastatin enhances neurite outgrowth in hippocampal neurons" *Journal of Neurochemistry*, May 2006, pp. 716-723, vol. 97 No. 3, XP-002571001.
Roehl, A. B. et al. "Neuroprotective properties of levosimendan in an in vitro model of traumatic brain injury" *BMC Neurology*, Oct. 21, 2010, pp. 1-4, vol. 10, No. 1, XP-021074880.
Spuch, C. et al. "Induction of angiogenesis by implantation of encapsulated cells expressing vegf: A new therapy approach on Alzheimer's disease?" *Journal of Neurological Sciences*, Aug. 2009, p. 260, vol. 283, No. 1-2, Issue 1, XP-002571001.
Van Den Bussche, H. et al. "Prescription patterns and effectiveness perception of anti-dementia drugs—A comparison between General Practitioners, Neurologists and Psychiatrists" *Nervenheilkunde*, 2005, pp. 485-492, vol. 24, No. 6, XP-009144765.
Wang, B. et al. "Protective Effects of Wu-Zi-Yan-Zong-Fang on Amyloid β-induced Damage in Vivo and in Vitro" *Database Biosis [Online] Biosciences Information Service*, Aug. 2009, pp. 941-948, vol. 129, No. 8.
Yoshida, K. et al. "Eplerenone Enhances Neovascularization Induced by Endothelial Progenitor Cells in Rat Hindlimb Ischemia" *18th Scientific Meeting of the European-Society-of-Hypertension*, 22nd Scientific Meeting of the Inter, Berlin, Germany, Jun. 14-19, 2008, Poster session PJ-413, XP-009144604, abstract only.

(56) References Cited

OTHER PUBLICATIONS

Database Biosis [Online] Bioscience Information Service, Philadelphia, Pa, Yoshihiko, K. et al. "Donepezil, an acetylcholiesterase inhibitor against Alzheimer's dementia, promotes angiogenesis in an ischemic limb model of nicotinic alpha 7 k0 mice" Database Accession No. PREV200800197710, Oct. 2007, pp. 1-2, vol. 116, No. 16, Suppl. S., XP-002613420.

Database Biosis [Online] Bioscience Information Service, Philadelphia, Pa, Wang, B. et al. "Protective Effects of Wu-Zi-Yan-Zong-Fang on Amyloid β-induced Damage in Vivo and in Vitro" Database Accession No. PREV200900521928, Aug. 2009, pp. 1-2, vol. 129, No. 8, Suppl. S., XP-002613420.

Berenbaum, M.C., "Synergy, additivism and antagonism in immunosuppression: A Critical Review," *Clin. exp. Immunol.*, 1977, pp. 1-18, vol. 28.

Jalbert, J.J. et al., "Dementia of the Alzheimer Type," *Epidemiologic Reviews*, 2008, pp. 15-34, vol. 30.

Jantzen and Robinson, *Modern Pharaceutics 3rd Edition*, published 1996, Marcel Dekker Inc., New York, NY, ed. Gilbert S. Banker et al., p. 596.

Levin, E.D. et al., "Baclofen interactions with nicotine in rats: effects on memory," *Pharmacology, Biochemistry and Behavior*, 2004, pp. 343-348, vol. 79.

Rogers, S.L. et al., "Donepezil Improves Cognition and Global Function in Alzheimer Disease," *Arch Intern Med*, 1998, pp. 1021-1031, vol. 158.

Rosse, R.B. et al., "Baclofen Treatment in a Patient With Tardive Dystonia," *J. Clin Psychiatry*, 1986, pp. 474-475, vol. 47.

Wilcox, D.M. et al., "Anti-Aβ immunotherapy in Alzheimer's disease; relevance of transgenic mouse studies to clinical trials," *J. Alzheimers Dis.*, 2008, pp. 555-569, vol. 15, No. 4.

Flannery, B. A. et al. "Baclofen for Alcohol Dependence: A Preliminary Open-Label Study" *Alcohol Clin Exp Res.*, Oct. 2004, pp. 1517-1523, vol. 28, No. 10.

Colombo, G. et al. "Role of GABA(B) receptor in alcohol dependence: reducing effect of baclofen on alcohol intake and alcohol motivational properties in rats and amelioration of alcohol withdrawal syndrome and alcohol craving in human alcoholics" *Neurotoxicity Research*, 2004, vol. 6, No. 5, pp. 403-414, abstract No. 0015545024.

Soyka, M. "Efficacy of acamprostate in the relapse prevention of alcohol dependence. Results of clinical trials and therapeutical prospects" *Nervenheilkunde*, 1995, pp. 83-86, vol. 14, No. 2, abstract No. 1995201786.

Binbay, Z. et al. "The efficacy of donepezil in two cases with alcohol induced Karsakoff's syndrome" *Klinik Psikofarmakoloji Bulteni*, 2008, pp. 49-49, Vol. 18, No. 1, abstract No. 2008102413.

BACLOFEN AND ACAMPROSATE BASED THERAPY OF NEUROLOGICAL DISORDERS

CROSS-REFERENCE TO RELATED APPLICATIONS

This application is a continuation-in-part of U.S. application Ser. No. 13/691,981, filed Dec. 3, 2012, which is a continuation of International Application No. PCT/EP2012/053570, filed Mar. 1, 2012, which claims the benefit of U.S. Provisional Ser. No. 61/468,658, filed Mar. 29, 2011 and Ser. No. 61/493,606, filed Jun. 6, 2011.

FIELD OF THE INVENTION

The present invention relates to combinations and methods for the treatment of neurological diseases and disorders. More specifically, the present invention relates to novel combinatorial therapy of neurological disorders, based on baclofen and acamprosate combination.

BACKGROUND OF THE INVENTION

Alzheimer's disease (AD) is the prototypic cortical dementia characterized by memory deficit together with dysphasia (language disorder in which there is an impairment of speech and of comprehension of speech), dyspraxia (disability to coordinate and perform certain purposeful movements and gestures in the absence of motor or sensory impairments) and agnosia (ability to recognize objects, persons, sounds, shapes, or smells) attributable to involvement of the cortical association areas. Special symptoms such as spastic paraparesis (weakness affecting the lower extremities) can also be involved [1-4].

Incidence of Alzheimer's disease increases dramatically with the age. AD is at present the most common cause of dementia. It is clinically characterized by a global decline of cognitive function that progresses slowly and leaves end-stage patients bound to bed, incontinent and dependent on custodial care. Death occurs, on average, 9 years after diagnosis [5].

United Nation population projections estimate that the number of people older than 80 years will approach 370 million by the year 2050. Currently, it is estimated that 50% of people older than age 85 years are afflicted with AD. Therefore, more than 100 million people worldwide will suffer from dementia in 50 years. The vast number of people requiring constant care and other services will severely affect medical, monetary and human resources [6].

Memory impairment is the early feature of the disease and involves episodic memory (memory for day-today events). Semantic memory (memory for verbal and visual meaning) is involved later in the disease. By contrast, working memory (short-term memory involving structures and processes used for temporarily storing and manipulating information) and procedural memory (unconscious memory that is long-term memory of skills and procedure) are preserved until late. As the disease progresses, the additional features of language impairment, visual perceptual and spatial deficits, agnosias and apraxias emerge.

The classic picture of Alzheimer's disease is sufficiently characteristic to allow identification in approximately 80% of cases [7]. Nevertheless, clinical heterogeneity does occur and this is not only important for clinical management but provides further implication of specific medication treatments for functionally different forms [8].

The pathological hallmark of AD includes amyloid plaques containing beta-amyloid (Abeta), neurofibrillary tangles (NFT) containing Tau and neuronal and synaptic dysfunction and loss [9-11]. For the last decade, two major hypotheses on the cause of AD have been proposed: the "amyloid cascade hypothesis", which states that the neurodegenerative process is a series of events triggered by the abnormal processing of the Amyloid Precursor Protein (APP) [12], and the "neuronal cytoskeletal degeneration hypothesis" [13], which proposes that cytoskeletal changes are the triggering events. The most widely accepted theory explaining AD progression remains the amyloid cascade hypothesis [14-16] and AD researchers have mainly focused on determining the mechanisms underlying the toxicity associated with Abeta proteins. Microvascular permeability and remodeling, aberrant angiogenesis and blood brain barrier (BBB) breakdown have been identified as key events contributing to the APP toxicity in the amyloid cascade [17]. On the contrary, Tau protein has received much less attention from the pharmaceutical industry than amyloid, because of both fundamental and practical concerns. Moreover, synaptic density change is the pathological lesion that best correlates with cognitive impairment than the two others. Studies have revealed that the amyloid pathology appears to progress in a neurotransmitter-specific manner where the cholinergic terminals appear most vulnerable, followed by the glutamatergic terminals and finally by the GABAergic terminals [11]. Glutamate is the most abundant excitatory neurotransmitter in the mammalian nervous system. Under pathological conditions, its abnormal accumulation in the synaptic cleft leads to glutamate receptors overactivation [18]. Abnormal accumulation of glutamate in synaptic cleft leads to the overactivation of glutamate receptors that results in pathological processes and finally in neuronal cell death. This process, named excitotoxicity, is commonly observed in neuronal tissues during acute and chronic neurological disorders.

It is becoming evident that excitotoxicity is involved in the pathogenesis of multiple disorders of various etiology such as: spinal cord injury, stroke, traumatic brain injury, hearing loss, alcoholism and alcohol withdrawal, alcoholic neuropathy, or neuropathic pain as well as neurodegenerative diseases such as Frontotemporal dementia, multiple sclerosis, Alzheimer's disease, Amyotrophic Lateral Sclerosis, Parkinson's disease, and Huntington's disease [19-21]. The development of efficient treatment for these diseases remains major public health issues due to their incidence as well as lack of curative treatments.

Two kinds of medication are used for improving or slowing down symptoms of AD which lay on some acetylcholinesterase modulators and a blocker of NMDA glutamate receptors, memantine [22,23].

NMDAR antagonists that target various sites of this receptor have been tested to counteract excitotoxicity. Uncompetitive NMDAR antagonists target the ion channel pore thus reducing the calcium entry into postsynaptic neurons. Some of them reached the approval status. As an example, memantine is currently approved in moderate to severe Alzheimer's disease. It is clinically tested in other indications that include a component of excitotoxicity such as alcohol dependence (phase II), amyotrophic lateral sclerosis (phase III), dementia associated with Parkinson (phase II), epilepsy, Huntington's disease (phase IV), multiple sclerosis (phase IV), Parkinson's disease (phase IV) and traumatic brain injury (phase IV). This molecule is however of limited benefit to most Alzheimer's disease patients, because it has only modest symptomatic effects. Another approach in limiting excitotoxicity consists in inhibiting the presynaptic release of glutamate. Riluzole, currently approved in amyotrophic lateral sclerosis, showed encouraging results in ischemia and traumatic brain injury models [24-26]. It is at present tested in phase II trials in early multiple sclerosis, Parkinson's disease (does not show any better results than placebo) as well as spinal cord injury. In 1995, the drug reached orphan drug status for the treatment of amyotrophic lateral sclerosis and in 1996 for the treatment of Huntington's disease. The use of NMDA receptor antagonists such as memantine, felbamate, acamprosate and MRZ 2/579 for treating depression has also been suggested in US2010076075.

WO2009133128, WO2009133141, WO2009133142 and WO2011054759 disclose drug combinations for use in the treatment of AD.

Despite active research in this area, there is still a need for alternative or improved efficient therapies for neurological disorders and, in particular, neurological disorders which are related to glutamate and/or amyloid beta toxicity. The present invention provides new treatments for such neurological diseases of the central nervous system (CNS) and the peripheral nervous system (PNS).

SUMMARY OF INVENTION

It is an object of the present invention to provide new therapeutic methods and compositions for treating neurological disorders. More particularly, the invention relates to compositions and methods for treating neurological disorders related to glutamate and/or amyloid beta (Aβ) toxicity, based on a combination of baclofen and acamprosate.

The invention stems, inter alia, from the unexpected discovery, by the inventors, that the combination of baclofen and acamprosate provides substantial and unexpected benefit to patients with Alzheimer's disease. Moreover, the inventors have surprisingly discovered that this combination provides substantial and unexpected protection of neuronal cells against various injuries encountered in neurological disorders including glutamate toxicity. Thus, this combination of baclofen and acamprosate constitutes an efficient treatment for patients suffering from, predisposed to, or suspected to suffer from neurological disorders. The inventors have found that combinations of the invention are efficient in counteracting the toxic cellular effects of AB peptide and in correcting the cognitive impairments in relation with such toxicity. The invention further demonstrates that baclofen and acamprosate administration does improve memory functions in aged subjects as well as cognitive functions, in particular by correcting cognition related electro-physiological features in mild AD patients.

An object of this invention therefore relates to compositions comprising a combination of baclofen and acamprosate, for use in the treatment of a neurological disorder, particularly AD and related disorders, Multiple Sclerosis (MS), Amyotrophic Lateral Sclerosis (ALS), Parkinson's disease (PD), neuropathies (for instance neuropathic pain or alcoholic neuropathy), Frontotemporal Dementia (FTD), alcoholism or alcohol withdrawal, Huntington's disease (HD) and spinal cord injury.

The compositions of the invention may contain baclofen and acamprosate as the only active ingredients. Alternatively, the compositions may comprise additional active ingredient(s). In this regard, a further object of this invention relates to a composition comprising a combination of baclofen, acamprosate, and at least one third compound selected from sulfisoxazole, methimazole, prilocaine, dyphylline, quinacrine, carbenoxolone, aminocaproic acid, cabergoline, diethylcarbamazine, cinacalcet, cinnarizine, eplerenone, fenoldopam, leflunomide, levosimendan, sulodexide, terbinafine, zonisamide, etomidate, phenformin, trimetazidine, mexiletine, ifenprodil, moxifloxacin, bromocriptine or torasemide, for use in the treatment of neurological disorders in a subject in need thereof.

As it will be further disclosed in the present application, the compounds in a combinatorial therapy of the invention may be administered simultaneously, separately, sequentially and/or repeatedly to the subject.

The invention also relates to any pharmaceutical composition per se comprising a combination of at least two compounds as defined above.

The compositions of the invention typically further comprise one or several pharmaceutically acceptable excipients or carriers. Also, the compounds as used in the present invention may be in the form of a salt, hydrate, ester, ether, acid, amide, racemate, or isomer. They may also be in the form of sustained-release formulations. Prodrugs or derivatives of the compounds may be used as well.

In a preferred embodiment, a compound is used as such or in the form a salt, hydrate, ester, ether or sustained release form thereof. A particularly preferred salt for use in the present invention is acamprosate calcium.

In another preferred embodiment, a prodrug or derivative is used.

A further object of this invention is a method of preparing a pharmaceutical composition, the method comprising mixing baclofen and acamprosate, in a pharmaceutically acceptable excipient or carrier.

Another object of this invention relates to a method for treating a neurological disorder in a mammalian subject in need thereof, preferably a human subject in need thereof, the method comprising administering to said subject an effective amount of a combination of the invention.

A further object of this invention relates to a method for treating Alzheimer's disease (AD) or a related disorder in a mammalian subject in need thereof, preferably a human subject in need thereof, the method comprising administering to said subject an effective amount of a combination of the invention.

A preferred object of this invention relates to a method for treating a neurological disorder in a mammalian subject in need thereof, preferably a human subject in need thereof, the method comprising simultaneously, separately or sequentially administering to said subject an effective amount of baclofen and acamprosate.

A particular object of this invention relates to a method of treating Frontotemporal Dementia (FTD) in a mammalian subject in need thereof, preferably a human subject in need thereof, the method comprising administering to said subject an effective amount of a combination of the invention.

A more preferred object of this invention relates to a method for treating AD or a related disorder in a mammalian subject in need thereof, preferably a human subject in need thereof, the method comprising simultaneously, separately or sequentially administering to said subject an effective amount of baclofen and acamprosate.

Another particular object of this invention relates to a method of treating Age Associated Memory Impairment (AAMI) in a mammalian subject in need thereof, preferably a human subject in need thereof, the method comprising administering to said subject an effective amount of a combination of the invention.

The invention may be used for treating a neurological disorder in any mammalian subject, preferably in any human subject, at any stage of the disease. As it will be disclosed in the examples, the compositions of the invention are able to ameliorate the pathological condition of said subjects.

DETAILED DESCRIPTION OF THE INVENTION

Figure 1:
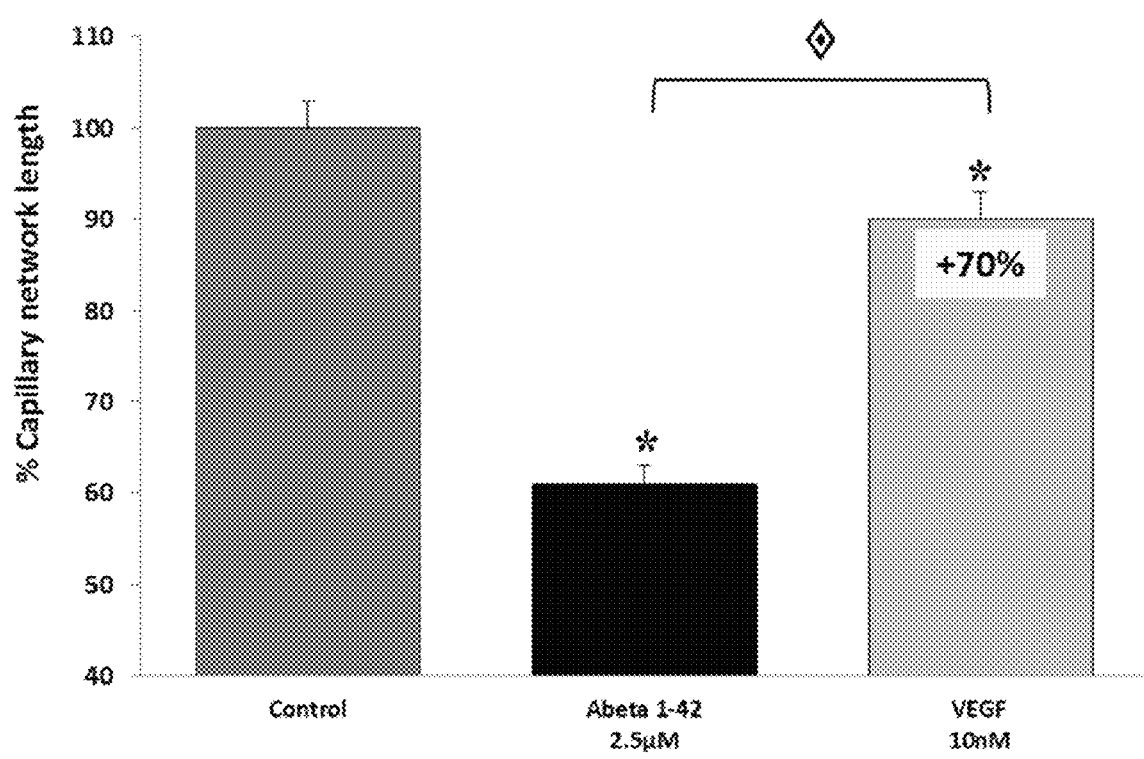
FIG. 1: Validation of the experimental model of human beta-amyloid toxicity on endothelial cells used for drug screening. One hour of VEGF pre-treatment at 10 nM significantly protected the capillary network from this amyloid injury (+70% of capillary network compared to amyloid intoxication).

The present invention provides new methods and compositions for treating neurological disorders. The invention discloses novel drug combinations which allow an effective correction of such diseases and may be used in any mammalian subject.

The invention is suited for treating any neurological disorders, whether central or peripheral, particularly disorders wherein nerve or neuron injuries, β amyloid, BBB breakdown or glutamate excitotoxicity are involved. Specific examples of such disorders include neurodegenerative diseases, neuropathies, spinal cord injury, and substances abuse such as alcoholism.

DEFINITIONS

"Neurodegenerative disorders" refer to diseases, such as Alzheimer's disease (AD) and related disorders, Amyotrophic Lateral Sclerosis (ALS), Multiple Sclerosis (MS), Parkinson's Disease (PD), Huntington's Disease (HD), encompassing a progressive loss of function and death of neurons.

Neuropathies refer to conditions where nerves of the peripheral nervous system are damaged, this includes damages of the peripheral nervous system provoked by genetic factors, inflammatory disease, or by chemical substance including drugs (vincristine, oxaliplatin, ethyl alcohol). The treatment of neuropathies also includes the treatment of neuropathic pain.

The invention is particularly suited for treating AD and related disorders. In the context of this invention, the term "related disorder" includes senile dementia of AD type (SDAT), frontotemporal dementia (FTD), vascular dementia, mild cognitive impairment (MCI) and age-associated memory impairment (AAMI).

As used herein, "treatment" includes the therapy, prevention, prophylaxis, retardation or reduction of symptoms provoked by or of the causes of the above diseases or disorders. The term treatment includes in particular the control of disease progression and associated symptoms. The term treatment particularly includes i) a protection against the toxicity caused by Amyloid Beta, or a reduction or retardation of said toxicity, and/or ii) a protection against glutamate excitotoxicity, or a reduction or retardation of said toxicity, in the treated subjects. The term treatment also designates an improvement of cognitive symptoms or a protection of neuronal cells.

Within the context of this invention, the designation of a specific drug or compound is meant to include not only the specifically named molecule, but also any pharmaceutically acceptable salt, hydrate, derivative, isomer, racemate, conjugate, prodrug or derivative thereof of any chemical purity.

The terms "combination" or "combinatorial treating/therapy" designate a treatment wherein at least baclofen and acamprosate are co-administered to a subject to cause a biological effect. In a combined therapy according to this invention, the at least two drugs may be administered together or separately, at the same time or sequentially. Also, the at least baclofen and acamprosate may be administered through different routes and protocols. As a result, although they may be formulated together, the drugs of a combination may also be formulated separately.

The term "prodrug" as used herein refers to any functional derivatives (or precursors) of a compound of the present invention, which, when administered to a biological system, generates said compound as a result of e.g., spontaneous chemical reaction(s), enzyme catalysed chemical reaction(s), and/or metabolic chemical reaction(s). Prodrugs are usually inactive or less active than the resulting drug and can be used, for example, to improve the physicochemical properties of the drug, to target the drug to a specific tissue, to improve the pharmacokinetic and pharmacodynamic properties of the drug and/or to reduce undesirable side effects. Some of the common functional groups that are amenable to prodrug design include, but are not limited to, carboxylic, hydroxyl, amine, phosphate/phosphonate and carbonyl groups. Prodrugs typically produced via the modification of these groups include, but are not limited to, esters, carbonates, carbamates, amides and phosphates. Specific technical guidance for the selection of suitable prodrugs is general common knowledge [27-31]. Furthermore, the preparation of prodrugs may be performed by conventional methods known by those skilled in the art. Methods which can be used to synthesize other prodrugs are described in numerous reviews on the subject [28,32-38]. For example, arbaclofen placarbil is listed in ChemID plus Advance database (website: chem.sis.nlm.nih.gov/chemidplus/) and arbaclofen placarbil is a well-known prodrug of baclofen [39,40].

The term "derivative" of a compound includes any molecule that is functionally and/or structurally related to said compound, such as an acid, amide, ester, ether, acetylated variant, hydroxylated variant, or an alkylated (C1-C6) variant of such a compound. The term derivative also includes structurally related compound having lost one or more substituent as listed above. For example, homotaurine is a deacetylated derivative of acamprosate. Preferred derivatives of a compound are molecules having a substantial degree of similarity to said compound, as determined by known methods. Similar compounds along with their index of similarity to a parent molecule can be found in numerous databases such as PubChem (http://pubchem.ncbi.nlm.nih.gov/search/) or DrugBank (http://www.drugbank.ca/). In a more preferred embodiment, derivatives should have a Tanimoto similarity index greater than 0.4, preferably greater than 0.5, more preferably greater than 0.6, even more preferably greater than 0.7 with a parent drug. The Tanimoto similarity index is widely used to measure the degree of structural similarity between two molecules. Tanimoto similarity index can be computed by software such as the Small Molecule Subgraph Detector [41,42] available online (http://www.ebi.ac.uk/thornton-srv/software/SMSD/). Preferred derivatives should be both structurally and functionally related to a parent compound, i.e., they should also retain at least part of the activity of the parent drug, more preferably they should have a protective activity against $A\beta$ or glutamate toxicity.

The term "derivative" also includes metabolites of a drug, e.g., a molecule which results from the (biochemical) modification(s) or processing of said drug after administration to an organism, usually through specialized enzymatic systems, and which displays or retains a biological activity of the drug. Metabolites have been disclosed as being responsible for much of the therapeutic action of the parent drug. In a specific embodiment, a "metabolite" as used herein designates a modified or processed drug that retains at least part of the activity of the parent drug, preferably that has a protective activity against $A\beta$ toxicity or glutamate toxicity.

The term "salt" refers to a pharmaceutically acceptable and relatively non-toxic, inorganic or organic salt of a compound of the present invention. Pharmaceutical salt formation consists in pairing an acidic, basic or zwitterionic drug molecule with a counterion to create a salt version of the drug. A wide variety of chemical species can be used in neutralization reaction. Pharmaceutically acceptable salts of the invention thus include those obtained by reacting the main compound, functioning as a base, with an inorganic or organic acid to form a salt, for example, salts of acetic acid, nitric acid, tartric acid, hydrochloric acid, sulfuric acid, phosphoric acid, methane sulfonic acid, camphor sulfonic acid, oxalic acid, maleic acid, succinic acid or citric acid. Pharmaceutically acceptable salts of the invention also include those in which the main compound functions as an acid and is reacted with an appropriate base to form, e.g., sodium, potassium, calcium, magnesium, ammonium, or choline salts. Though most of salts of a given active principle are bioequivalents, some may have, among others, increased solubility or bioavailability properties. Salt selection is now a common standard operation in the process of drug development as taught by H. Stahl and C.G. Wermuth in their handbook [43].

In a preferred embodiment, the designation of a compound is meant to designate the compound per se, as well as any pharmaceutically acceptable salt, hydrate, isomer, racemate, ester or ether thereof.

In a more preferred embodiment, the designation of a compound is meant to designate the compound as specifically designated per se, as well as any pharmaceutically acceptable salt thereof.

In a particular embodiment, a sustained-release formulation of the compound is used.

Compositions and Methods of the Invention

As discussed above, the invention relates to particular drug combinations which have a strong unexpected effect on several biological processes involved in neurological disorders. These drug combinations therefore represent novel approaches for treating neurological disorders, such as Alzheimer's disease and related disorders, multiple sclerosis, amyotrophic lateral sclerosis, Parkinson's disease, Huntington's disease, neuropathies (for instance neuropathic pain or alcoholic neuropathy), alcoholism or alcohol withdrawal, and spinal cord injury. More specifically, the invention discloses compositions, comprising baclofen in combination with acamprosate, which provide a significant effect in vivo on neurological disorders.

Indeed, the invention shows, in the experimental part, that combination therapies comprising baclofen and acamprosate can substantially improve the condition of patients afflicted with neurological disorders. In particular, the inventors have surprisingly discovered that baclofen and acamprosate combinations have a strong, unexpected effect on the length of capillary network, on LDH release in beta-amyloid intoxicated nervous cells as well as on the length of neurite network, and represent new therapeutic approaches of AD. They have also discovered that baclofen-acamprosate combinations are efficient in lowering the $A\beta$ induced oxidative stress, apoptosis, glutamate release and phosphorylated Tau accumulation in neuronal cells.

Also, the examples show that, in a combination therapy of the invention, baclofen may be effective at a dose of 80 nM or less, and that acamprosate may be effective at a dose of 1 nM or less. These results are remarkable and particularly advantageous since, at such low doses, any possible side effects are avoided. Moreover inventors have been able to determine plasmatic and/or brain concentration ranges at which such a combination therapy exerts a simultaneous protective activity against the three aspects of $A\beta$ toxicity in relation with AD pathogenesis, i.e., angiogenesis, neuronal protection and neuronal plasticity. Furthermore, these combinations effectively protect neuronal cells from various afflictions such as glutamate toxicity, oxidative stress and prevent BBB permeabilization or neuronal cells induced apoptosis which are involved in several neurological disorders.

The present invention therefore proposes a novel therapy of neurological disorders, based on baclofen and acamprosate compositions. More particularly, the present invention therefore proposes a novel therapy of Alzheimer's disease and related disorders, multiple sclerosis, amyotrophic lateral sclerosis, Parkinson's disease, Huntington's disease, neuropathies (for instance neuropathic pain or alcoholic neuropathy), alcoholism or alcohol withdrawal, and spinal cord injury, based on baclofen and acamprosate combinations.

In this regard, in a particular embodiment, the invention relates to a composition comprising baclofen and acamprosate.

In a further embodiment, the invention relates to a composition comprising baclofen and acamprosate for use in the treatment of AD, AD related disorders, MS, PD, ALS, HD, neuropathies (for instance neuropathic pain or alcoholic neuropathy), alcoholism or alcohol withdrawal, or spinal cord injury.

In a further embodiment, the invention relates to the use of baclofen and acamprosate for the manufacture of a medicament for the treatment of AD, AD related disorders, MS, PD, ALS, HD, neuropathies (for instance neuropathic pain or alcoholic neuropathy), alcoholism or alcohol withdrawal, or spinal cord injury.

Illustrative CAS numbers for baclofen and acamprosate are provided in Table 1 below. Table 1 cites also, in a non-limitative way, common salts, racemates, prodrugs, metabolites or derivatives for these compounds used in the compositions of the invention.

TABLE 1

| Drug | CAS Numbers | Class or Tanimoto similarity index |
|---|---|---|
| Acamprosate and related compounds | | |
| Acamprosate | 77337-76-9; 77337-73-6 | NA |
| Homotaurine | 3687-18-1 | 0.73 |
| Ethyl Dimethyl Ammonio Propane Sulfonate | / | 0.77 |
| Taurine | 107-35-7 | 0.5 |
| Baclofen and related compounds | | |
| Baclofen | 1134-47-0; 66514-99-6; 69308-37-8; 70206-22-3; 63701-56-4; 63701-55-3 | NA |
| 3-(p-chlorophenyl)-4-hydroxybutyric acid | / | Metabolite |
| Arbaclofen placarbil | 847353-30-4 | Prodrug |

Specific examples of prodrugs of baclofen are given in Hanafi et al. [44], particularly baclofen esters and baclofen ester carbamates, which are of particular interest for CNS targeting. Hence such prodrugs are particularly suitable for compositions of this invention. Arbaclofen placarbil as mentioned before is also a well-known prodrug and may thus be used instead of Baclofen in compositions of the invention. Other prodrugs of baclofen can be found in the following patent applications: WO2010102071, US2009197958, WO2009096985, WO2009061934, WO2008086492, US2009216037, WO2005066122, US2011021571, WO2003077902, WO2010120370.

Useful prodrugs for acamprosate such as pantoic acid ester neopentyl sulfonyl esters, neopentyl sulfonyl esters prodrugs of acamprosate or masked carboxylate neopentyl sulfonyl ester prodrugs of acamprosate are notably listed in WO2009033069, WO2009033061, WO2009033054, WO2009052191, WO2009033079, US 2009/0099253, US 2009/0069419, US 2009/0082464, US 2009/0082440, and US 2009/0076147.

Baclofen and acamprosate combination therapy may be used alone or may be further combined with additional compounds. In this regard, in a particular embodiment, the compositions of the invention may further comprise at least one compound selected from sulfisoxazole, methimazole, prilocaine, dyphylline, quinacrine, carbenoxolone, aminocaproic acid, cabergoline, diethylcarbamazine, cinacalcet, cinnarizine, eplerenone, fenoldopam, leflunomide, levosimendan, sulodexide, terbinafine, zonisamide, etomidate, phenformin, trimetazidine, mexiletine, ifenprodil, moxifloxacin, bromocriptine or torasemide. Illustrative CAS numbers for each of these compounds are provided in Table 2 below:

TABLE 2

| DRUG NAME | CAS NUMBER |
|---|---|
| Aminocaproic Acid | 60-32-2 |
| Bromocriptine | 25614-03-3 |
| Cabergoline | 81409-90-7 |
| Carbenoxolone | 5697-56-3 |
| Cinacalcet | 226256-56-0 |
| Cinnarizine | 298-57-7 |
| Diethylcarbamazine | 90-89-1 |
| Dyphylline | 479-18-5 |
| Eplerenone | 107724-20-9 |
| Etomidate | 33125-97-2 |
| Fenoldopam | 67227-57-0 |
| Ifenprodil | 23210-56-2 or 23210-58-4 |
| Leflunomide | 75706-12-6 |
| Levosimendan | 141505-33-1 |
| Methimazole | 60-56-0 |
| Mexiletine | 5370-01-4 or 31828-71-4 |
| Moxifloxacin | 354812-41-2 |
| Phenformin | 114-86-3 |
| Prilocaine | 721-50-6 or 14289-31-7 or 14289-32-8 |
| Quinacrine | 83-89-6 |
| Sulfisoxazole | 127-69-5 |
| Sulodexide | 57821-29-1 |
| Terbinafine | 91161-71-6 |
| Torasemide | 56211-40-6 or 72810-59-4 |
| Trimetazidine | 5011-34-7 or 13171-25-0 |
| Zonisamide | 68291-97-4 |

In a particular embodiment, the invention relates to the use of this combination for treating AD or a related disorder in a subject in need thereof.

In another particular embodiment, the invention relates to the use of this combination for treating an AD related disorder selected from senile dementia of AD type (SDAT), frontotemporal dementia (FTD), vascular dementia, mild cognitive impairment (MCI) and age-associated memory impairment (AAMI).

A particular object of this invention relates to a method of treating frontotemporal dementia (FTD) in a mammalian subject in need thereof, preferably a human subject in need thereof, the method comprising administering to said subject an effective amount of a combination of the invention.

In a particular embodiment, the invention relates to the use of this combination for treating MS, PD, ALS, HD, neuropathies (for instance neuropathic pain or alcoholic neuropathy), alcoholism or alcohol withdrawal, or spinal cord injury, in a subject in need thereof.

As disclosed in the examples, composition therapies using at least baclofen and acamprosate have a strong unexpected effect on biological processes leading to neuronal injuries. Furthermore, these combinations also showed in vivo a very efficient ability to correct symptoms of neurological diseases. These combinations therefore represent novel approaches for treating neurological disorders, such as AD, MS, ALS, PD, HD, neuropathies (for instance neuropathic pain or alcoholic neuropathy), alcoholism or alcohol withdrawal, and spinal cord injury. These compositions efficiently prevent toxicity of amyloid β (Aβ) peptide or glutamate excitotoxicity on neuronal cells. More particularly, as shown in the experimental section, these compositions are efficient in counteracting, simultaneously, the detrimental effects of intoxication by Aβ oligomers at the synaptic, neuronal and endothelial levels. Such combination of effects is particularly advantageous and leads to a significant improvement of the disease both in several in vivo models for AD and in clinical trials. Indeed, in vivo, these compositions lead to an improvement of several cognitive symptoms as well as to a protection of neuronal cells.

Furthermore the experimental section shows that the above mentioned compositions are also efficient i) in synergistically protecting in vitro neuronal cells from glutamate excitotoxicity, and ii) in conferring clinical benefit in in vivo models for diseases related to glutamate excitotoxicity.

Hence they represent novel and potent methods for treating such disorders.

The compositions of the invention may comprise 2, 3, 4 or 5 distinct drugs, more preferably 2, 3 or 4 distinct drugs for combinatorial treatment of Alzheimer's disease (AD), AD related disorders, MS, PD, ALS, HD, neuropathies (for instance neuropathic pain or alcoholic neuropathy), alcoholism or alcohol withdrawal, or spinal cord injury in a subject in need thereof. In a preferred embodiment, the drugs of the invention are used in combination(s) for combined, separate or sequential administration, in order to provide the most effective effect.

Preferred compositions of the invention, for use in the treatment of a neurological disorder such as Alzheimer's disease (AD), AD related disorders, MS, PD, ALS, HD, neuropathies (for instance neuropathic pain or alcoholic neuropathy), alcoholism or alcohol withdrawal, or spinal cord injury, comprise one of the following drug combinations, for combined, separate or sequential administration:

baclofen and acamprosate,
baclofen and acamprosate and diethylcarbamazine,
baclofen and acamprosate and cinacalcet,
baclofen and acamprosate and sulfisoxazole,
baclofen and acamprosate and torasemide,
baclofen and acamprosate and ifenprodil,
baclofen and acamprosate and mexiletine,
baclofen and acamprosate and eplerenone,
baclofen and acamprosate and levosimendan,
baclofen and acamprosate and terbinafine, or
baclofen and acamprosate and leflunomide.

As disclosed in the experimental section, combinatorial therapies of the invention provide substantial therapeutic and biological effect to improve Alzheimer's disease or related disorders in both animal model and human subjects. They induce a strong neuroprotective effect against Aβ toxicity notably through the inhibition of Aβ induced apoptosis and oxidative stress. They also give positive results in behavioural performances and biochemical assays in rodents. Results show that compositions of the invention in vivo: (i) efficiently correct molecular pathways triggered by Aβ oligomers, and (ii) lead to an improvement of neurophysiological impairments observed in diseased animals as neuron survival or synapse integrity. Results also show that compositions of the invention efficiently restore blood-brain barrier (BBB) and prevent, retard, or lessen apoptosis triggering, which are known to be impaired in several neurological diseases. Combinatorial therapies are also efficient in correcting memory impairment in aged animals. Results from clinical trials in human subjects also show an activity on cognitive performances of AD patients.

Figure 15:
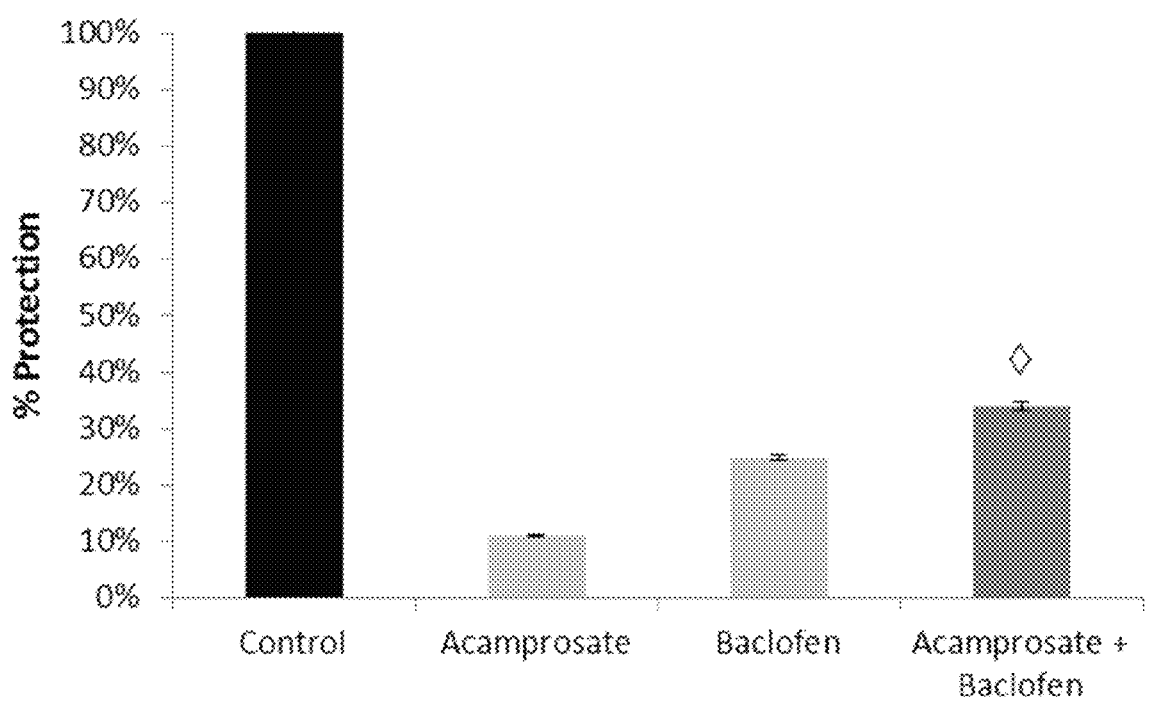
FIG. 15: Effect of baclofen and acamprosate combination therapy against glutamate toxicity on neuronal cortical cells. Glutamate intoxication is significantly prevented by the combination of baclofen (400 nM) and acamprosate (1.6 nM) whereas, at those concentrations, baclofen and acamprosate alone have no significant effect on intoxication. ◇: p<0.001, significantly different from glutamate intoxication; (ANOVA+Dunnett Post-Hoc test).

Moreover, the results presented show also that the above combinations therapies have an important synergistic neuroprotective effect against glutamate excitotoxicity (FIG. 15) a pathway which is implicated in various neurological diseases as AD, MS, PD, ALS, HD, neuropathies (for instance neuropathic pain or alcoholic neuropathy), alcoholism or alcohol withdrawal, or spinal cord injury. These therapies give positive results in in vivo or in vitro models for these diseases.

Furthermore, the particularly high synergistic interaction observed for these two drugs through combinatorial treatment of the invention allows the use of drug concentrations showing no effect when used in single drug treatment. Moreover, as shown in the experimental section, baclofen and acamprosate combination causes an enhanced therapeutic benefit in treating Alzheimer's disease compared to other therapeutic combinations. These compositions efficiently prevent the toxic effects of amyloid β protein or peptide on human cells and in an in vivo model and represent novel and potent methods for treating such disorder.

An object of this invention thus also resides in a composition as defined above for treating a neurological disorder such as AD, AD related disorders, MS, PD, ALS, HD, neuropathies (for instance alcoholic neuropathy or neuropathic pain), alcoholism or alcohol withdrawal, or spinal cord injury.

As indicated previously, in a combination therapy of this invention, the compounds or drugs may be formulated together or separately, and administered together, separately or sequentially.

A further object of this invention resides in the use of a composition as defined above for the manufacture of a medicament for treating a neurological disorder such as Alzheimer's disease (AD), AD related disorders, MS, PD, ALS, HD, neuropathies (for instance neuropathic pain or alcoholic neuropathy), alcoholism or alcohol withdrawal, or spinal cord injury.

The invention further provides a method for treating a neurological disorder such as Alzheimer's disease (AD), AD related disorders, MS, PD, ALS, HD, neuropathies (for instance neuropathic pain or alcoholic neuropathy), alcoholism or alcohol withdrawal, or spinal cord injury, comprising administering to a subject in need thereof an effective amount of a composition as disclosed above.

A further object of the invention is a method of treating a neurological disorder such as Alzheimer's disease (AD), AD related disorders, MS, PD, ALS, HD, neuropathies (for instance neuropathic pain or alcoholic neuropathy), alcoholism or alcohol withdrawal, or spinal cord injury, the method comprising simultaneously, separately or sequentially administering to a subject in need thereof an effective amount of a composition as disclosed above.

In a preferred embodiment, the invention relates to a method of treating a neurological disorder such as Alzheimer's disease (AD), AD related disorders, MS, PD, ALS, HD, neuropathies (for instance neuropathic pain or alcoholic neuropathy), alcoholism or alcohol withdrawal, or spinal cord injury in a subject in need thereof, comprising administering simultaneously, separately or sequentially to the subject an effective amount of baclofen and acamprosate.

The compositions of the invention typically comprise one or several pharmaceutically acceptable carriers or excipients. Also, for use in the present invention, the drugs or compounds are usually mixed with pharmaceutically acceptable excipients or carriers.

In this regard, a further object of this invention is a method of preparing a pharmaceutical composition, the method comprising mixing the above compounds in an appropriate excipient or carrier.

In a particular embodiment, the method comprises mixing baclofen and acamprosate in an appropriate excipient or carrier.

According to preferred embodiments of the invention, as indicated above, the compounds are used as such or in the form of a pharmaceutically acceptable salt, prodrug, derivative, or sustained release formulation thereof.

Although very effective in vitro and in vivo, depending on the subject or specific condition, the combination therapy of the invention may further be used in conjunction, association or combination with additional drugs or treatments beneficial to the treated neurological condition in the subject.

Other therapies used in conjunction with drug(s) or drug(s) combination(s) according to the present invention, may comprise one or more drug(s) that ameliorate symptoms of Alzheimer's disease, an AD related disorder, MS, PD, ALS, HD, neuropathies (for instance neuropathic pain or alcoholic neuropathy), alcoholism or alcohol withdrawal, or spinal cord injury, or drug(s) that could be used for palliative treatment of these disorders. For instance, results show also that the above combinations therapies have an important synergistic neuroprotective effect when combined with donepezil (FIG. 16) or memantine (FIG. 19), thereby allowing the use of low doses of said compounds and avoiding or lessening side effects. Thereby, illustrative therapies which can be used with combinations of the invention are donepezil (CAS: 120014-06-4), galantamine (CAS: 357-70-0), gabapentine (CAS: 478296-72-9; 60142-96-3), rivastigmine (CAS: 123441-03-2) or memantine (CAS: 19982-08-2). The above CAS numbers are only given in an illustrative way, and common salts, enantiomeric form, racemate, prodrugs, metabolites or derivatives for the above compounds should be also considered.

In this regard, in a particular embodiment, the drug(s) or compositions according to the present invention may be further combined with *Ginkgo biloba* extracts. Suitable extracts include, without limitation, *Ginkgo biloba* extracts, improved *Ginkgo biloba* extracts (for example enriched in active ingredients or lessened in contaminant) or any drug containing *Ginkgo biloba* extracts.

In another particular embodiment, the drug(s) or compositions according to the present invention may be further combined with drugs or compounds which are currently under phase III clinical trial for AD. These drugs or compounds include Epigallocatechin-3-gallate, Human neutral insulin, Idalopirdine, Vanutide cridificar, Durin-Leuprolide acetate, Gantenerumab, Latrepirdine hydrochloride, Solanezumab, Masitinib mesylate, Encenicline hydrochloride, Leuco methylthioninium salt, IGIV, Lu-AE-58-054, VP4896, INM-176, R04909832, SK-PCB70M, AC-1204, MK8931.

Furthermore, the inventors have been able to decipher the molecular mechanisms underlying the unexpected efficiency of combinations of the invention. The results show that (i) baclofen exerts a Gaba B agonistic activity which is essential for the neuroprotective activity and that (ii) acamprosate exerts a particular pattern of biological interactions (table 3) that is essential for neuroprotective effect in the context of AD or AD related disorders.

Figure 22:
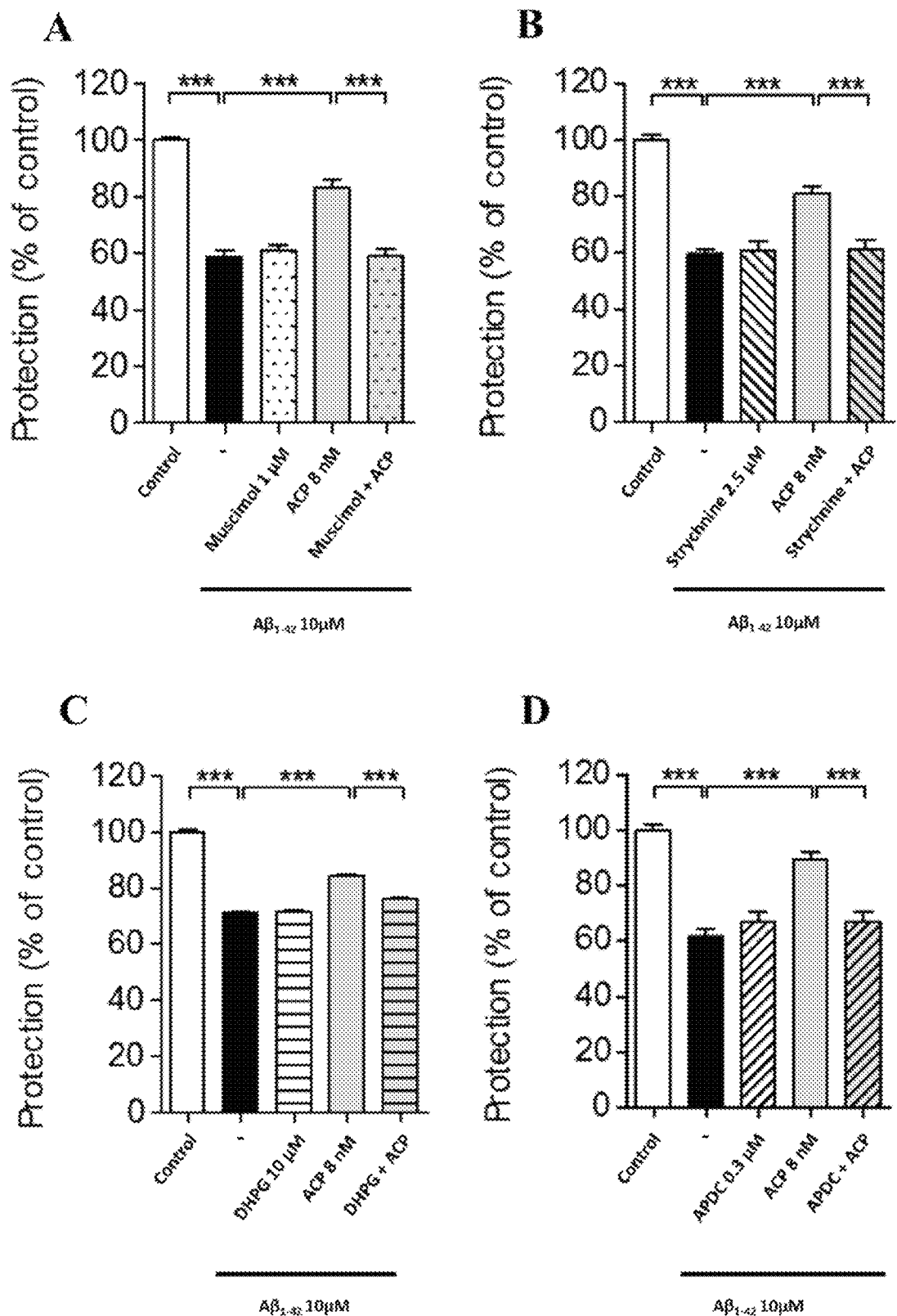
FIGS. 22A-22D: Acamprosate (ACP) acts through GABA$_A$, Glycine and metabotropic glutamatergic receptors signaling. Aβ$_{1-42}$ (10 µM) produces a significant intoxication of cells (-, black bars, up to 40% of death) compared to vehicle-treated neurons (control, white bars). This intoxication is efficiently prevented by acamprosate 8 nM (grey bars, up to 71% of improvement). Muscimol, a GABA$_A$ receptor agonist (A), Strychnine, a Glycine receptor antagonist (B), DHPG, a mGluR1/5 agonist (C) and (2R,4R)-APDC a mGluR2/3 agonist (D) all block ACP protection of rat primary neuronal cells. Values are mean±s.e.m. ***: p<0.001 versus Aβ, or ACP pretreated and Aβ intoxicated cells (ANOVA+Dunnett Post-Hoc test). "Control": non Aβ intoxicated non treated cells; "-": Aβ intoxicated cells. mGluR1/5 and mGluR2/3: metabotropic glutamate group I and II receptors respectively.

As shown in the experimental section, counteracting only one of these mechanisms of action results in an almost total abolition of the neuroprotective effect of acamprosate against Aβ toxicity (FIG. 22). Notably, the inventors show for the first time that, in the context of AD pathogenesis, acamprosate exerts an antagonistic effect on GABA A receptors which is essential to afford neuroprotection against Aβ. Hence, together with the agonistic action of baclofen on GABA B receptors, the concerted action of acamprosate on the four identified receptor families leads to particular efficient therapeutic effect as described in this whole disclosure. This concerted action on several targets when using only one drug make thus acamprosate of particular interest.

Furthermore, based on the knowledge of the pattern of action provided in the present application, it is now possible to design and use alternative combinations of drugs in replacement of e.g., acamprosate. Such alternative combinations should exhibit the same pattern of biological interaction as shown for acamprosate in table 3 and, in particular, they should (i) antagonize GABA A receptors and Group I and II metabotropic receptors, and (ii) lead to an increased activity of glycinic receptors.

Consequently, in a particular embodiment, this invention relates to a combination of baclofen with a drug having an antagonist activity on GABA A receptors, as well as on Group I and II metabotropic receptors, and an agonist activity on glycinic receptors.

In a particular embodiment, the invention relates to a combination of baclofen with a combination of drugs, said combination of drugs having an antagonistic activity toward GABA A receptors and Group I and II metabotropic receptors, as well as an agonistic activity toward glycinic channels. Said combination of drugs used as an alternative to acamprosate can comprise 2, 3, 4, 5 or even 6 drugs in order to mimic the pleiotropic activity of acamprosate. Ideally, some of the drugs used in said composition act on several of the targets identified by the inventors. More preferably some of the drugs used in said composition act on 2, or 3 or 4 of the targets identified by the inventors. Hence, more preferably, the combination of drugs used as an alternative to acamprosate comprises 2, 3 or 4 drugs.

An agonistic or antagonistic activity toward a receptor/channel refers to a direct action on said receptor/channel or to an indirect action leading to the activation or inhibition of the said receptor/channel.

An agonistic or antagonistic activity refers also to a positive or negative allosteric modulation, respectively.

Drugs suitable to elaborate such a combination of drugs are listed in table 4 below with their corresponding CAS number, IUPAC name or related articles, in an illustrative purpose only.

TABLE 3

|  | Gaba A receptors | Glycine receptors | Groupe I metabotropic glutamatergic receptors | Groupe II metabotropic glutamatergic receptors |
|---|---|---|---|---|
| Acamprosate activity * | antagonist | agonist | antagonist | antagonist |

* pattern of activity that has been shown necessary to afford a protective effect against toxicity of Aβ

TABLE 4

| antagonists of group I mGluR | | | |
|---|---|---|---|
| GRM1 | | GRM5 | |
| AIDA | 168560-79-0 | ADX 10059 | 1166398-32-8; 757949-98-7 |
| A-794278 | 869802-57-3 | AZD-2066 | 1403991-95-6; 934282-55-0; 934338-70-2 |
| A-794282 | 869802-44-8 | AZD6538 | Raboisson et al 2012 [45] |
| A-841720 | 869802-58-4 | AZD9272 | 1166398-50-0 |
| A-850002 | 869802-73-3 | Basimglurant | 802906-73-6 |
| Bay-36-7620 | 232605-26-4 | Dipraglurant | 872363-17-2 |
| FTIDC | Suzuki et al 2007 [46] | Fenobam | 57653-26-6; 63540-28-3 |

TABLE 4-continued

| | | | |
|---|---|---|---|
| JNJ-16259685 | 409345-29-5 | GRN529 | 1253291-12-1 |
| LY-367385 | 198419-91-9 | LY-344545 | 201851-20-9 |
| RO0711401 | 714971-87-6 | Mavoglurant | 543906-09-8 |
| YM-202074 | 299900-83-7 | MPEP | 219911-35-0 |
| YM-230888 | Kohara et al 2007 [47] | MRZ-8676 | Dekundy et al 2011 [48] |
| YM-298198 | 748758-45-4 | MTEP | 329205-68-7; 1186195-60-7 |
| | | Rufinamide | 106308-44-5 |
| | | SIB-1757 | 31993-01-8 |
| | | SIB-1893 | 7370-21-0 |

Antagonists of group II m GluR (GRM2 and 3)

| | |
|---|---|
| BCI-632 | 569686-87-9 |
| BCI-1038 | (N/A) Prodrug of B632 |
| BCI-1206 | (N/A) Prodrug of B632 |
| BCI-1283 | (N/A) Prodrug of B632 |
| BCI-838 | (1R,2R,3R,5R,6R)-2-Amino-3-[(3,4-dichlorobenzyl)oxy]-6-fluoro-6-[(heptyloxy)carbonyl]bicyclo[3.1.0]hexane-2-carboxylic acid |
| RG-1578 | 911115-16-7 |
| RO4491533 | 579482-31-8 |
| LY-341495 | 201943-63-7 |
| APICA | 170847-18-4 |
| EGLU | 170984-72-2 |

Antagonists of Gaba A receptors

| | |
|---|---|
| $\alpha_5$IA | 215874-86-5 |
| beta-Cce | 74214-62-3 |
| beta-Ccm | 69954-48-9 |
| beta-Cct | 93835-05-3 |
| bicuculline | 485-49-4; 56083-00-2 |
| BTS-72-664 | (R)-7-[1-(4-chlorophenoxy)]ethyl]-1,2,4-triazolo(1,5-alpha)pyrimidine |
| cicutoxin | 505-75-9 |
| clarithromycin | 81103-11-9 |
| DMCM | 82499-00-1 |
| FG71-42 | 78538-74-6 |
| FGIN-1-27 | 142720-24-9 |
| FGIN-1-44 | 2-hexyl-indole-3-acetamide-N-benzene-tricarboxylic acid |
| flumazenil | 78755-81-4 |
| gabazine | 104104-50-9 |
| L-655708 | Ethyl (S)-11,12,13,13a-Tetrahydro-7-methoxy-9-oxo-9H-imidazo[1,5-a]pyrrolo[2,1-c][1,4]benzodiazepine-1-carboxylate |
| lorediplon | 917393-39-6 |
| MK0777 | 252977-51-8 |
| oenanthotoxin | 20311-78-8 |
| pentetrazol | 54-95-5 |
| picrotoxin | 124-87-8 |
| pitrazepin | 90685-01-1 |
| PWZ-029 | 8-chloro-3-(methoxymethyl)-5-methyl-4H-imidazo[1,5-a] [1,4]benzodiazepin-6-one |
| R04882224 | 3,10-dichloro-9H-benzo[f]imidazo[1,5-a][1,2,4]triazolo[1,5-d][1,4]diazepine |
| RO15-3505 | ethyl 7-chloro-5-methyl-6-oxo-5,6-dihydro-4H-imidazo[1,5-a][1,4]benzodiazepine-3-carboxylate |
| Ro15-4513 | ethyl-8-azido-5,6-dihydro-5-methyl-6-oxo-4H-imidazo[1,4]-benzodiazepine-3-carboxylate |
| RO-4938581 | 3-bromo-10-(difluoromethyl)-9H-benzo[f]imidazo[1,5-a][1,2,4]triazolo[1,5-d][1,4]diazepine |
| RU-5135 | 78774-26-2 |
| RY-023 | (tert-butyl-8-(trimethylsilyl) acetylene-5,6-dihydro-5-methyl-6-oxo-4H-imidazo [1,5a] [1,4] benzodiazepine-3-carboxylate |
| RY-024 | t-butyl-8-ehtynyl-(5,6-dihydro-5-methyl-6-oxo-4H-imidazo (1,5-a)[1,4]benzodiazepine-3-carboxylate |
| RY-024 | t-butyl-8-ehtynyl-(5,6-dihydro-5-methyl-6-oxo-4H-imidazo (1,5-a)[1,4]benzodiazepine-3-carboxylate |
| RY-80 | ethyl 8-ethynyl-5-methyl-6-oxo-4H-imidazo[1,5-a][1,4]benzodiazepine-3-carboxylate |
| S8510 | [2-(3-isoxazolyl)-3,6,7,9-tetrahydroimidazo [4,5-d] pyrano [4,3-b] pyridine monophosphate monohydrate] |
| sarmazenil | 78771-13-8 |
| SR-42641 | 105537-78-8 |
| SR-95103 | 96440-63-0 |
| thiocolchicoside | 602-41-5 |
| thujone | 1125-12-8; 546-80-5; 471-15-8; 33766-30-2 |
| TP003 | 628690-75-5 |
| US-1010 | 516-55-2 |
| ZK-93423 | 89592-45-0 |

TABLE 4-continued

Agonists of Glycinic channels

| | |
|---|---|
| anandamide | 94421-68-8 |
| cycloserine | 68-41-7 |
| dimethylglycine | 1118-68-9 |
| dronabinol | 1972-08-3 |
| enflurane | 13838-16-9 |
| glycine | 56-40-6 |
| Halothane | 151-67-7 |
| HU 210 | 112830-95-2 |
| hypotaurine | 300-84-5 |
| isoflurane | 26675-46-7 |
| milacemide | 76990-56-2 |
| sarcosine | 203-538-6 |
| serine | 302-84-1; 56-45-1; 312-84-5 |
| sevoflurane | 28523-86-6 |
| taurine | 107-35-7 |
| trimethylglycine | 107-43-7; 17146-86-0 |
| alanine | 302-72-7; 56-41-7; 338-69-2 |
| β alanine | 107-95-9 |
| WIN 55212-2 | 131543-23-2 |
| arachidonyl-glycerol | 53847-30-6 |

In a particular embodiment, said combination of drugs used as an alternative to acamprosate comprises at least one compound selected from $\alpha_5$IA, beta-Cce, beta-Ccm, beta-Cct, bicuculline, BTS-72-664, cicutoxin, clarithromycin, DMCM, FG71-42, FGIN-1-27, FGIN-1-44, flumazenil, gabazine, L-655708, lorediplon, MK0777, oenanthotoxin, pentetrazol, picrotoxin, pitrazepin, PWZ-029, R04882224, RO15-3505, Ro15-4513, RO-4938581, RU-5135, RY-023, RY-024, RY-024, RY-80, S8510, sarmazenil, SR-42641, SR-95103, thiocolchicoside, thujone, TP003, US-1010, or ZK-93423, which are known as (direct or indirect) antagonists or inverse agonists of the GABA A receptors.

In a preferred embodiment, said combination of drugs used as an alternative to acamprosate comprises thiocolchicoside.

In another particular embodiment, antagonists or inverse agonists of the GABA A receptors of use can be, but are not limited to, one those described in WO2011/153377, WO2012/059482, EP2457569, WO2011/024115 which are herein incorporated by reference.

In an embodiment, antagonists of the Group I metabotropic receptors that can be used in a combination of drugs used as an alternative to acamprosate may be, but are not limited to, one of those disclosed in WO2004014370A2, WO2004014881A2, WO2004014902A2, WO2005080356A1, WO2005080363A1, WO2005080386A1, WO2006014185A1, WO2007021574A1, WO2007021575A2, WO2007130825A2, WO2009051556A1, WO2009054785A1, WO2009054786A1, WO2009054789A1, WO2009054790A1, WO2009054791A1, WO2009054792A1, WO2009054793A1, WO2009054794A1, WO2010123451A1, WO02068417A2, WO2005066155A1, WO2004000316A1, WO2005080379A1, WO2005080397A2, WO2007040982A1, WO2010019100A1, WO2007130820A2, WO2007130821A2, WO2007130822A2, WO2007130823A2, WO2007130824A2, WO2008041075A1, WO2009054787A1, WO9926927A2, WO2004069813A1, WO2012127393 A1, WO2003047581A1, WO2008128968 which are incorporated herein by reference.

Further antagonists of the Group I metabotropic receptors that can be used are disclosed in WO2012108831A1 and are incorporated herein by reference.

Yet further antagonists of the Group I metabotropic receptors that can be used are disclosed in WO2012127393A1 are incorporated herein by reference.

Other antagonists of the Group I metabotropic receptors that can be used are disclosed in WO2010048095A2 are incorporated herein by reference.

Antagonists of the Group I metabotropic receptors have been the focus of numerous research programs in drug discovery which are summarized by Jaeschke et al (2007)[50], Carroll (2008)[51] and Emmitte (2013)[52]. All the antagonists of the Group I metabotropic receptors disclosed in these reviews can be considered are incorporated herein by reference to be used in a combination of drugs used as an alternative to acamprosate.

In a particular embodiment, said combination of drugs used as an alternative to acamprosate comprises at least one compound having an antagonistic activity for mGluR1 metabotropic receptors and/or at least one compound having an antagonistic activity for mGluR5 metabotropic.

In a particular embodiment, said combination of drugs used as an alternative to acamprosate comprises at least one compound selected from AIDA, A-794278, A-794282, A-841720, A-850002, Bay-36-7620, FTIDC, JNJ-16259685, LY-367385, R00711401, YM-202074, YM-230888, YM-298198, ADX 10059, AZD-2066, AZD6538, AZD9272, basimglurant, dipraglurant, fenobam, GRN529, LY-344545, mavoglurant, MPEP, MRZ-8676, MTEP, rufinamide, SIB-1757, SIB-1893 which are known as (direct or indirect) antagonists of the Group I metabotropic receptors.

In a preferred embodiment, said combination of drugs used as an alternative to acamprosate comprises rufinamide.

In another preferred embodiment said combination of drugs used as an alternative to acamprosate comprises a compound selected from AIDA, A-794278, A-794282, A-841720, A-850002, Bay-36-7620, FTIDC, JNJ-16259685, LY-367385, R00711401, YM-202074, YM-230888, YM-298198 and a compound selected from ADX 10059, AZD-2066, AZD6538, AZD9272, basimglurant, dipraglurant, fenobam, GRN529, LY-344545, mavoglurant, MPEP, MRZ-8676, MTEP, rufinamide, SIB-1757, and SIB-1893.

In a particular embodiment combination of drugs used as an alternative to acamprosate comprises a compound acting as an antagonist of both mGluR1 and mGluR5 receptors.

In an embodiment, combination of drugs used as an alternative to acamprosate comprises a drug that acts as an antagonist or negative allosteric modulator of mGluR2 or mGluR3 (group II) metabotropic glutamate receptors.

In another embodiment, combination of drugs used as an alternative to acamprosate comprises a drug that acts as an antagonist or negative allosteric modulator of mGluR2 and mGluR3 (group II) metabotropic glutamate receptors.

Antagonists of group II metabotropic glutamate receptors comprises, but are not limited to, EGLU, APICA, LY-341495, BCI-632 or its prodrugs BCI-1038, BCI-1206, BCI-1283, BCI-838, or one of the 2-amino-bicyclo[3.1.0]hexane-2,6-dicarboxylic ester derivatives disclosed in WO2005000791, US2012028982, US2012004232, US2010298561, US2009306408, US2007021394, or 5H-thiazolo (3,2-a) pyrimidine derivatives disclosed in U.S. Pat. No. 5,958,931 which are incorporated herein by reference.

Negative allosteric modulators of the Group II metabotropic receptors that can be used in a combination of drugs used as an alternative to acamprosate comprise, but are not limited to, DT-2228 as disclosed in Froestl et al (2012) [53] and incorporated herein by reference, RG-1578, R04432717, R04491533, dihydrobenzo[1,4]diazepin-2-one derivatives disclosed in Hempstapat et al 2007 [54] and incorporated herein by reference, compounds described in WO 2014/064028, WO 01/29011, WO 01/29012, WO 02/083652, WO 02/083665, WO 02/098864, WO 03/066623, WO 2005/014002, WO 2005/040171, WO2005/123738, WO 2006/084634, WO 2006/099972, WO 2007/039439, WO 2007/110337 and WO 2008/119689 and incorporated herein by reference.

In another embodiment, combination of drugs used as an alternative to acamprosate comprises a drug that acts as agonists or positive allosteric modulators of the glycinic channels.

In a particular embodiment, said combination of drugs comprises anandamide, cycloserine, dimethylglycine, dronabinol, enflurane, glycine, halothane, HU 210, hypotaurine, isoflurane, milacemide, sarcosine, serine, sevoflurane, taurine, trimethylglycine, D and/or L alanine, or β alanine which are known as agonists or positive allosteric modulators of the glycinic channels.

Other agonists or positive allosteric modulators of the glycinic channels that can be used in said combination of drug comprise propofol derivatives described in WO 2010/067069 and which are incorporated herein by reference. Agonists or positive allosteric modulators of the glycinic channels comprise also, but are not limited to, tropines and nortropines which are described in Maksay et al. (2007) [55] are also herein incorporated by reference as well as those listed in Yevenes & Zeilhofer [56].

Therapy according to the invention may be provided at home, the doctor's office, a clinic, a hospital's outpatient department, or a hospital, so that the doctor can observe the therapy's effects closely and make any adjustments that are needed.

The duration of the therapy depends on the stage of the disease being treated, age and condition of the patient, and how the patient responds to the treatment. The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recovery from any as yet unforeseen side-effects. The drugs may also be formulated together such that one administration delivers all drugs.

The administration of each drug of the combination may be by any suitable means that results in a concentration of the drug that, combined with the other component, is able to ameliorate the patient condition or efficiently treat the disease or disorder.

While it is possible for the drugs the combination to be administered as the pure chemical it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the combination of the present invention.

The drug may be contained, in any appropriate amount, in any suitable carrier substance. The drug may be present in an amount of up to 99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the composition of the invention in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Drugs may be mixed together in the tablet, or may be partitioned. For example, a first drug is contained on the inside of the tablet, and a second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamnine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Alternative Routes

Although less preferred and less convenient, other administration routes, and therefore other formulations, may be contemplated. In this regard, for rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Therapeutically effective amounts of the drugs in a combination of this invention include, e.g., amounts that are effective for reducing Alzheimer's disease symptoms, halting or slowing the progression of the disease once it has become clinically manifest, or prevention or reduction of the risk of developing the disease.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

Administration can be one to several times daily for several days to several years, and may even be for the life of the patient. Chronic or at least periodically repeated long-term administration is indicated in most cases.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

The amount of each drug in a preferred unit dosage composition depends upon several factors including the administration method, the body weight and the age of the patient, the stage of the disease, the risk of potential side effects considering the general health status of the person to be treated. Additionally, pharmacogenomic (the effect of genotype on the pharmacokinetic, pharmacodynamic or efficacy profile of a therapeutic) information about a particular patient may affect the dosage used.

Except when responding to especially impairing cases, where higher dosages may be required, the preferred dosage of each drug in the combination will usually lie within the range of doses not above the dosage usually prescribed for long-term maintenance treatment or proven to be safe in phase 3 clinical studies.

One remarkable advantage of the invention is that each compound may be used at low doses in a combination therapy, while producing, in combination, a substantial clinical benefit to the patient. The combination therapy may indeed be effective at doses where the compounds have individually low or no effect. Accordingly, a particular advantage of the invention lies in the ability to use sub-optimal doses of each compound, i.e., doses which are lower than therapeutic doses usually prescribed, preferably ½ of therapeutic doses, more preferably ⅓, ¼, ⅕, or even more preferably ⅒ of therapeutic doses. In particular examples, doses as low as 1/20, 1/30, 1/50, 1/100, or even lower, of therapeutic doses are used.

At such sub-therapeutic dosages, the compounds would exhibit no side effect, while the combination(s) according to the invention are fully effective in treating Alzheimer's disease or AD related diseases.

A preferred dosage corresponds to amounts from 1% up to 50% of those usually prescribed for long-term maintenance treatment.

The most preferred dosage may correspond to amounts from 1% up to 10% of those usually prescribed for long-term maintenance treatment.

Specific examples of dosages of drugs for use in the invention are provided below:

Acamprosate between 0.1 and 1000 mg per day, preferably less than 400 mg per day, more preferably less than 200 mg per day, even more preferably 100 mg per day or less, furthermore preferably between 0.5 mg and 100 mg per day, typically 0.8 mg per day, 2 mg per day, 20 mg per day, 40 mg per day, or 80 mg per day, such dosages being particularly suitable for oral administration, Baclofen between 0.01 to 150 mg per day, preferably less than 100 mg per day, more preferably less than 50 mg per day, most preferably between 5 and 40 mg per day, even more preferably less than 35 mg per day, typically 12 mg per day, 24 mg per day, 30 mg per day, such dosages being particularly suitable for oral administration, Aminocaproic acid orally from about 0.1 g to 2.4 g per day,
bromocriptine orally from about 0.01 to 10 mg per day,
diethylcarbamazine orally from about 0.03 to 400 mg per day,
cabergoline orally from about 1 to 10 μg per day,
cinacalcet orally from about 0.3 to 36 mg per day,
cinnarizine orally from about 0.6 to 23 mg per day,
dyphylline orally from about 9 to 320 mg per day,
eplerenone orally from about 0.25 to 10 mg per day,
ifenprodil orally from about 0.4 to 6 mg per day,
leflunomide orally from about 0.1 to 10 mg per day,
levosimendan orally from about 0.04 to 0.8 mg per day,
mexiletine orally from about 6 to 120 mg per day,
moxifloxacin orally from about 4 to 40 mg per day,
phenformin orally from about 0.25 to 15 mg per day,
quinacrine orally from about 1 to 30 mg per day,
sulfisoxazole orally from about 20 to 800 mg per day,
sulodexide orally from about 0.05 to 40 mg per day,
terbinafine orally from about 2.5 to 25 mg per day,
torasemide orally from about 0.05 to 4 mg per day,
trimetazidine orally from about 0.4 to 6 mg per day,
zonisamide orally from about 0.5 to 50 mg per day,
administered in one, two, or three doses daily.

When the composition comprises, as active ingredient, only baclofen and acamprosate, these two compounds may be used in different ratios, e.g., at a weight ratio acamprosate/baclofen comprised between from 0.05 to 1000 (W:W), preferably between 0.05 to 100 (W:W), more preferably between 0.05 to 50 (W:W).

As already mentioned, the above compounds in the therapies of the invention can be used as specifically designated per se, as well as any pharmaceutically acceptable salt, enantiomer, racemate, prodrugs, metabolites or derivatives thereof.

In a particularly preferred embodiment, combinatorial therapies of the invention comprise administering between 0.4 mg and 50 mg of acamprosate and 6 mg to 15 mg baclofen, twice daily.

In an embodiment, combinatorial therapies of the invention comprise administering 0.4 mg acamprosate and 6 mg baclofen, twice daily.

In a preferred embodiment, combinatorial therapies of the invention comprise administering 1 mg acamprosate and 15 mg baclofen, twice daily.

In yet another preferred embodiment, combinatorial therapies of the invention comprise administering 10 mg acamprosate and 6 mg baclofen, twice daily.

In another preferred embodiment, combinatorial therapies of the invention comprise administering 20 mg acamprosate and 12 mg baclofen, twice daily.

In still another embodiment, combinatorial therapies of the invention comprise administering 40 mg acamprosate and 12 mg baclofen, twice daily.

In another particular embodiment, besides comprising administering one of the above baclofen-acamprosate regimen, therapies of the invention also comprise administering donepezil or memantine either at their usual dose and regimen (i.e. as an add-on therapy) or even at a lower dose, from 1% up to 50% of those usually prescribed for the treatment of AD.

In an even more particular embodiment, combinatorial therapies of the invention further comprise administering 0.6 mg donepezil twice daily.

Consequently, in a particularly preferred embodiment, combinatorial therapies of the invention comprise administering between 0.4 mg and 50 mg of acamprosate, 6 mg to 15 mg baclofen, and 0.6 mg donepezil, twice daily.

In an embodiment, combinatorial therapies the invention comprise administering 0.4 mg acamprosate, 6 mg baclofen, and 0.6 mg donepezil, twice daily.

In a preferred embodiment, combinatorial therapies of the invention comprise administering 1 mg acamprosate, 15 mg baclofen, 0.6 mg donepezil, twice daily.

In yet another preferred embodiment, combinatorial therapies of the invention comprise administering 20 mg acamprosate, 12 mg baclofen, and 0.6 mg donepezil, twice daily.

In a particularly preferred embodiment, combinatorial therapies of the invention comprise administering 40 mg acamprosate, 12 mg baclofen, and 0.6 mg donepezil twice daily.

As previously stated, the compounds in a combinatorial therapy of the invention may be administered simultaneously, separately, sequentially and/or repeatedly to the subject. Particularly, the above dosing regimen can be orally simultaneously administered using suitable tablets. Also, a particular object of this invention relates to a tablet comprising acamprosate and baclofen, suitable for the dosing regimen of a dose of acamprosate between 0.4 to 50 mg and a dose of baclofen between 6 to 15 mg, to be administered twice daily.

A further particular object of this invention relates to a tablet comprising acamprosate and baclofen, suitable for the dosing regimen of 0.4 mg acamprosate and 6 mg baclofen, twice daily.

Another particular object of this invention relates to a tablet comprising acamprosate and baclofen, suitable for the dosing regimen of 1 mg acamprosate and 15 mg baclofen, twice daily.

Another particular object of this invention relates to a tablet comprising acamprosate and baclofen, suitable for the dosing regimen of 20 mg acamprosate and 12 mg baclofen, to be administered twice daily.

A particular object of this invention relates to a tablet comprising acamprosate and baclofen, suitable for the dosing regimen of 40 mg acamprosate and 12 mg baclofen, to be administered twice daily.

An even more particular object of this invention relates to a tablet comprising baclofen, acamprosate and donepezil, said tablet being suitable for any of the above mentioned dosages of baclofen and acamprosate and also for the dosing regimen of 0.6 mg donepezil, twice daily.

A more particular object of the invention is a scored tablet suitable for the administration of any of the above dosing regimen, said tablet being cleavable in 2, 3 and/or 4 part as a function of the dose to be administered at each taking.

As mentioned above, a single unit dosage form containing the combinations of the invention is most preferred. Alternatively, where a separate administration would be considered more proper, combinations of the invention can be provided under the form of a unit dosage package. Such unit dosage package being configured to hold a first unit dosage comprising acamprosate and a second unit dosage comprising baclofen. In a particular embodiment unit dosages are tablets. In another particular embodiment the first unit dosage comprises between 0.4 to 50 mg of acamprosate and the second unit dosage comprises between 6 to 15 mg baclofen.

In another embodiment the first unit dosage is suitable for the dosing regimen of 0.4 mg acamprosate, twice daily.

In another embodiment the first unit dosage is suitable for the dosing regimen of 1 mg acamprosate, twice daily.

In another embodiment the first unit dosage is suitable for the dosing regimen of 20 mg acamprosate, twice daily.

In another embodiment the first unit dosage is suitable for the dosing regimen of 40 mg acamprosate, twice daily.

In an embodiment the first unit dosage is suitable for the dosing regimen of 1 mg acamprosate, twice daily.

In another embodiment the second unit dosage is suitable for the dosing regimen of 6 mg baclofen, twice daily.

In another embodiment the second unit dosage is suitable for the dosing regimen of 12 mg baclofen, twice daily.

In another embodiment the second unit dosage is suitable for the dosing regimen of 15 mg baclofen, twice daily.

In another particular embodiment, the above mentioned unit dosage package comprises a third unit dosage comprising donepezil. In a more particular embodiment this third unit dosage is suitable for the dosing regimen of 0.6 mg donepezil, twice daily. In a particular embodiment said unit dosage package contains a number of unit dosages suitable for 1, 2, 3, 4, 5, 6, 7 days of treatment or even more, preferably several week-treatment.

It will be understood that the amount of the drug actually administered will be determined by a physician, in the light of the relevant circumstances including the condition to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

The care and husbandry of animals as well as the experimentations are performed according to the guidelines of the Committee for Research and Ethical Issue of the I.A.S.P. (1983).

I. Treatment of Diseases Related to Aβ Toxicity

In this series of experiments, candidate combinations have been tested for their ability to prevent or reduce the toxic effects of human $A\beta_{1-42}$. $A\beta_{1-42}$ is the full length peptide that constitutes aggregates found in biopsies from human patients afflicted with AD. The effect is determined on various cell types, to further document the activity of the combinations in in vitro models which illustrate different physiological features of AD. In vivo studies are also performed in a mouse model for AD confirming this protective effect by evaluating the effect of the combinations on i) the cognitive performance of animals and ii) on molecular hallmarks (apoptosis induction, oxidative stress induction, inflammation pathway induction) of AD. Clinical results show that baclofen and acamprosate based compositions are actually efficient in improving cognitive performances as well as in correcting electrophysiological disturbances observed in patients diagnosed with mild AD.

A. Baclofen-Acamprosate Combination Therapies Prevent Toxicity of Human $A\beta_{1-42}$ In Vitro 1. Effect on the Toxicity of Human Aβ1-42 Peptide on Human Brain Microvascular Endothelial Cells (HBMEC).

HBMEC Culture Conditions

HBMEC cultures were used to study the protection afforded by candidate compound(s) on $A\beta_{1-42}$ toxicity.

HBMEC (ScienCell Ref: 1000, frozen at passage 10) were rapidly thawed in a water bath at +37° C. The supernatant was immediately put in 9 ml Dulbecco's modified Eagle's medium (DMEM; Pan Biotech ref: P04-03600) containing 10% of fetal calf serum (FCS; GIBCO ref 10270-106). Cell suspension was centrifuged at 180×g for 10 min at +4° C. and the pellets were suspended in CSC serum-free medium (CSC serum free, Cell System, Ref: SF-4Z0-500-R, Batch 51407-4) with 1.6% of Serum free RocketFuel (Cell System, Ref: SF-4Z0-500-R, Batch 54102), 2% of Penicillin 10.000 U/ml and Streptomycin 10 mg/ml (PS; Pan Biotech ref: P06-07100 batch 133080808) and were seeded at the density of 20 000 cells per well in 96 well-plates (matrigel layer biocoat angiogenesis system, BD, Ref 354150, Batch A8662) in a final volume of 100 μl. On matrigel support, endothelial cerebral cells spontaneously started the process of capillary network morphogenesis [57].

Three separate cultures were performed per condition, 6 wells per condition.

Test Compounds and Human $A\beta_{1-42}$ Treatment

Briefly, $A\beta_{1-42}$ peptide (Bachem, ref: H1368 batch 1010533) was reconstituted in define culture medium at 20 μM (mother solution) and was slowly shacked at +37 C for 3 days in dark. The control medium was prepared in the same conditions.

After 3 days, human amyloid peptide was used on HBMEC at 2.5 μM diluted in control medium (optimal incubation time). The $A\beta_{1-42}$ peptide was added 2 hours after HBMEC seeding on matrigel for 18 hours incubation.

One hour after HBMEC seeding on matrigel, test compounds and VEGF-165 were solved in culture medium (+0.1% DMSO) and then pre-incubated with HBMEC for 1 hour before the $A\beta_{1-42}$ application (in a final volume per culture well of 100 µl). One hour after test compounds or VEGF incubation (two hours after cell seeding on matrigel), 100 µl of $A\beta_{1-42}$ peptide was added to a final concentration of 2.5 µM diluted in control medium in presence of test compounds or VEGF (in a 200 µl total volume/well), in order to avoid further drug dilutions.

Organization of Cultures Plates

VEGF-165 known to be a pro-angiogenic isoform of VEGF-A, was used for all experiments in this study as reference compound. VEGF-165 is one of the most abundant VEGF isoforms involved in angiogenesis. VEGF was used as reference test compound at 10 nM (FIG. 1).

The following conditions were assessed:
Negative Control: medium alone+0.1% DMSO
Intoxication: amyloid-$\beta_{1-42}$ (2.5 µM) for 18 h
Positive control: VEGF-165 (10 nM) (1 reference compound/culture) 1 h before the $A\beta_{1-42}$ (2.5 µM) addition for a 18 h incubation time.
Test compounds: Test compound(s) 1 h before the $A\beta_{1-42}$ (2.5 µM) addition for a 18 h incubation time.

Capillary Network Quantification

Per well, 2 pictures with 4× lens were taken using InCell Analyzer™ 1000 (GE Healthcare) in light transmission. All images were taken in the same conditions. Analysis of the angiogenesis networks was done using Developer software (GE Healthcare). The total length of capillary network was assessed.

Data Processing

Data were expressed in percentage of control conditions (no intoxication, no amyloid=100%) in order to express the amyloid injury. All values were expressed as mean+/−SEM (s.e.mean) of the 3 cultures (n=6 wells per condition). Statistical analyses were done on the different conditions (ONE-WAY ANOVA followed by the Dunnett's test when it was allowed, Statview software version 5.0).

Results

Figure 2:
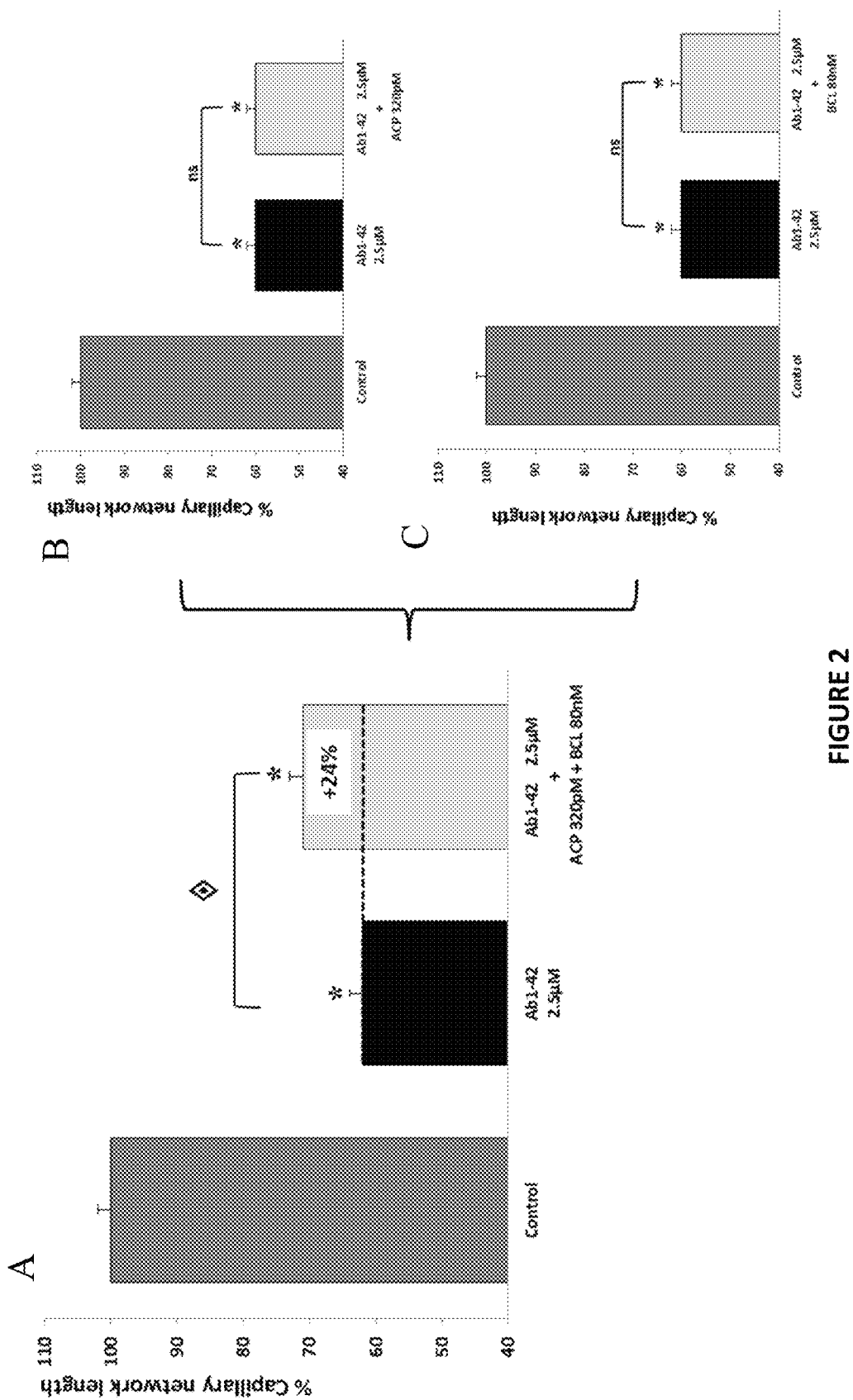
FIGS. 2A-2C: Effect of baclofen (BCL) and acamprosate (ACP) combination therapy on the total length of capillary network in beta-amyloid intoxicated HBMEC cultures. The human amyloid peptide ($A\beta_{1-42}$ 2.5 µM) produces a significant intoxication, above 40%, compared to vehicle-treated cells. This intoxication is significantly prevented by the combination of acamprosate and baclofen (A) whereas, at those concentrations, acamprosate (B) and baclofen (C) alone have no significant effect on intoxication. ◊: $p<0.05$, significantly different from $A\beta_{1-42}$ intoxication; *: $p<0.05$, significantly different from vehicle; "ns" no significant effect (ANOVA+Dunnett Post-Hoc test).

Baclofen-acamprosate combination gives a significant protective effect against toxicity of human $A\beta_{1-42}$ peptide in HBMEC model (a reduction of 24% of $A\beta_{1-42}$ peptide injury is observed), as shown in FIG. 2. The results clearly show that the intoxication by human amyloid peptide ($A\beta_{1-42}$ 2.5 µM) is significantly prevented by the drug combination whereas, at those concentrations, the drugs alone have no significant effect on intoxication in the experimental conditions described above.

Figure 3:
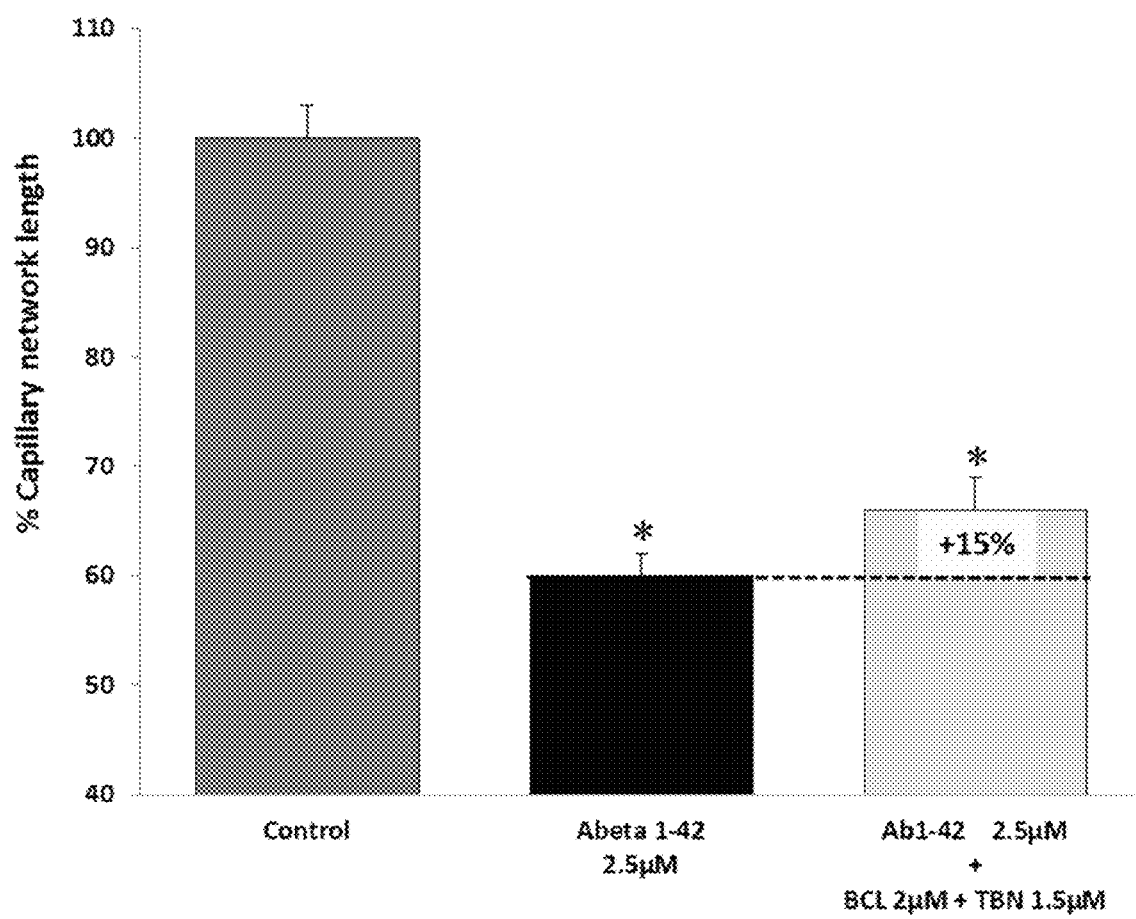
FIG. 3: Effect of baclofen (BCL) and terbinafine (TBN) combination therapy on the total length of capillary network in beta-amyloid intoxicated HBMEC cultures. The human amyloid peptide ($A\beta_{1-42}$ 2.5 µM) produces a significant intoxication, above 40%, compared to vehicle-treated cells. This intoxication is prevented by the combination of terbinafine and baclofen. *: $p<0.05$: significantly different from control (no intoxication).

Conversely, combination of baclofen and terbinafine (which is presented here only for the sake of comparison) affords a weaker protection (a reduction of 15% of $A\beta_{1-42}$ peptide injury is observed) against $A\beta_{1-42}$ (FIG. 3).

Thus, although these two combinations allow a protection against $A\beta_{1-42}$, the combination baclofen-acamprosate stands out clearly. Indeed, these drugs at concentrations having no effect alone allow significant protection of human HBMEC against $A\beta_{1-42}$ when used in combination. Furthermore, the baclofen-acamprosate combination is more effective than the baclofen-terbinafine combination. Such an effect of baclofen and acamprosate represents a remarkable improvement by 60% in comparison to e.g., the effect of the combination of baclofen-terbinafine.

Moreover, concentration of baclofen used in the baclofen-acamprosate combination is much lower than the concentration of baclofen used in the baclofen-terbinafine combination (25-fold reduction).

2. Effect on the Toxicity of Human Aβ1-42 Peptide on Primary Cortical Neuron Cells.

a) Baclofen-Acamprosate Combination has a Neuroprotective Effect

Culture of Primary Cortical Neurons

Rat cortical neurons were cultured as described by Singer et al. [58]. Briefly pregnant female rats of 15 days gestation were killed by cervical dislocation (Rats Wistar) and the foetuses were removed from the uterus. The cortex was removed and placed in ice-cold medium of Leibovitz (L15) containing 2% of Penicillin 10.000 U/ml and Streptomycin 10 mg/ml and 1% of bovine serum albumin (BSA). Cortices were dissociated by trypsin for 20 min at 37° C. (0.05%). The reaction was stopped by the addition of Dulbecco's modified Eagle's medium (DMEM) containing DNase1 grade II and 10% of foetal calf serum (FCS). Cells were then mechanically dissociated by 3 serial passages through a 10 ml pipette and centrifuged at 515×g for 10 min at +4° C. The supernatant was discarded and the pellet of cells was re-suspended in a defined culture medium consisting of Neurobasal supplemented with B27 (2%), L-glutamine (0.2 mM), 2% of PS solution and 10 ng/ml of BDNF. Viable cells were counted in a Neubauer cytometer using the trypan blue exclusion test. The cells were seeded at a density of 30 000 cells/well in 96 well-plates (wells were pre-coated with poly-L-lysine (10 µg/ml)) and were cultured at +37° C. in a humidified air (95%)/CO2 (5%) atmosphere.

Three independent cultures will be performed per condition, 6 wells per condition.

Test Compounds and Human Amyloid-β1-42 Treatment

Briefly, $A\beta_{1-42}$ peptide was reconstituted in define culture medium at 40 µM (mother solution) and was slowly shaken at +37° C. for 3 days in dark. The control medium was prepared in the same conditions.

After 3 days, the solution was used on primary cortical neurons as follows.

After 10 days of neuron culture, test compounds were solved in culture medium (+0.1% DMSO) and then pre-incubated with neurons for one hour before the $A\beta_{1-42}$ application (in a final volume per culture well of 100 µl). One hour after test compound(s) incubation, 100 µl of $A\beta_{1-42}$ peptide was added to a final concentration of 10 µM diluted in presence of drug(s), in order to avoid further test compound(s) dilutions. Cortical neurons were intoxicated for 24 h. Three separate cultures were performed per condition, 6 wells per condition.

BDNF (50 ng/ml) and Estradiol-β (150 nM) were used as positive control and reference compounds respectively. Three separate cultures were performed per condition, 12 wells per condition.

Organization of Cultures Plates

Figure 4:
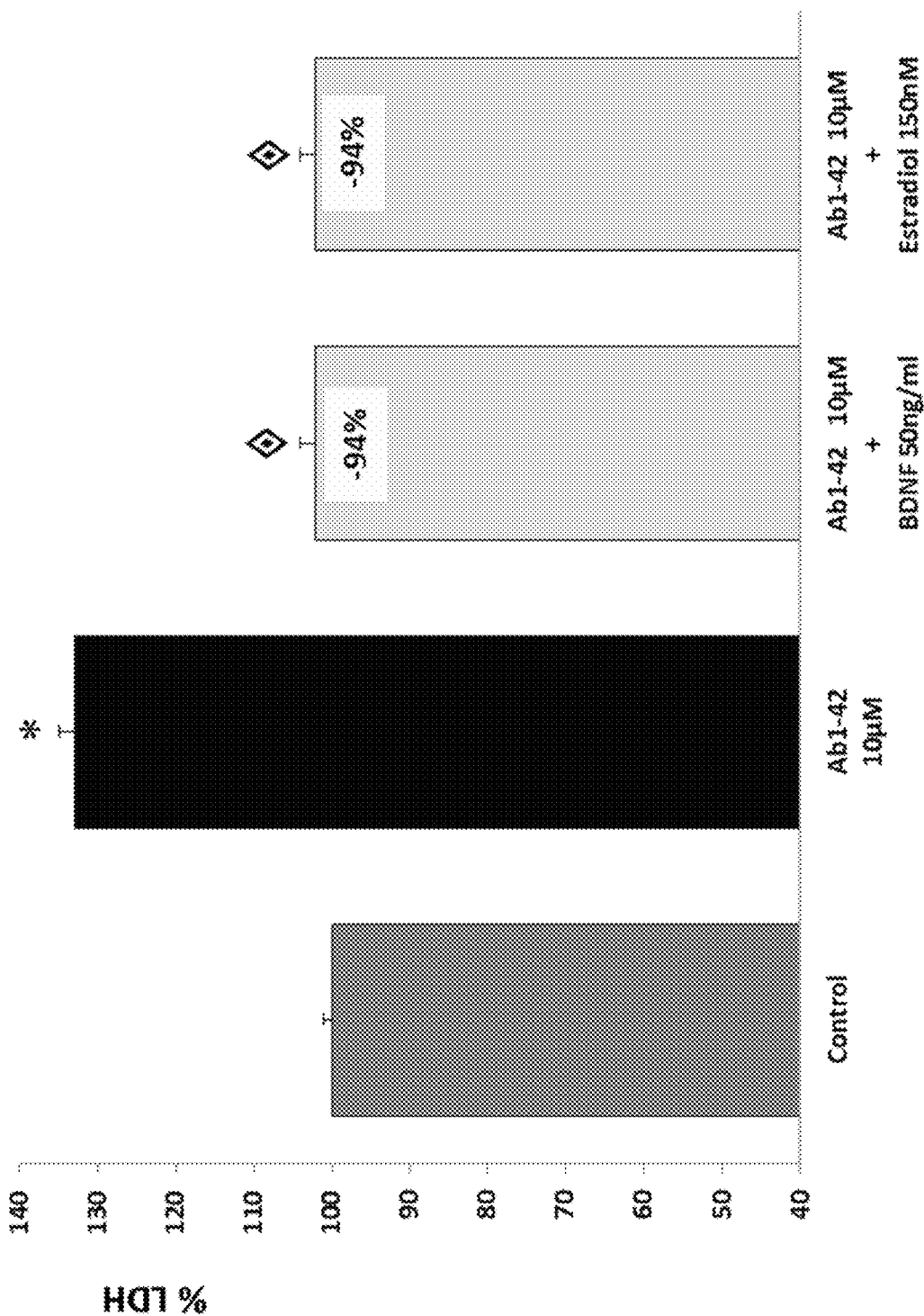
FIG. 4: Validation of the experimental model of human beta amyloid toxicity on neuronal cells used for drug screening. One hour of Estradiol (150 nM) or BDNF (50 ng/mL) pre-treatment significantly protected the neurons from this amyloid injury (−94%), which is considered as a positive control for neuroprotection. *: $p<0.05$, significantly different from control (no intoxication); ◊: $p<0.05$, significantly different from $A\beta_{1-42}$ intoxication.

Estradiol-β at 150 nM was used as a positive control (FIG. 4).

Estradiol-β was solved in culture medium and pre-incubated for 1 h before the amyloid-$\beta_{1-42}$ application.

The following conditions were assessed:
CONTROL PLAQUE: 12 wells/condition
 Negative Control: medium alone+0.1% DMSO,
 Intoxication: amyloid-$\beta_{1-42}$ (10 µM) for 24 h,
 Reference compound: Estradiol (150 nM) 1 h.
DRUG PLATE: 6 wells/condition
 Negative Control: medium alone+0.1% DMSO,
 Intoxication: amyloid-$\beta_{1-42}$ (10 µM) for 24 h,
 Test compound(s): test compound(s)–1 h followed by amyloid-$\beta_{1-42}$ (10 µM) for 24 h.

Figure 5:
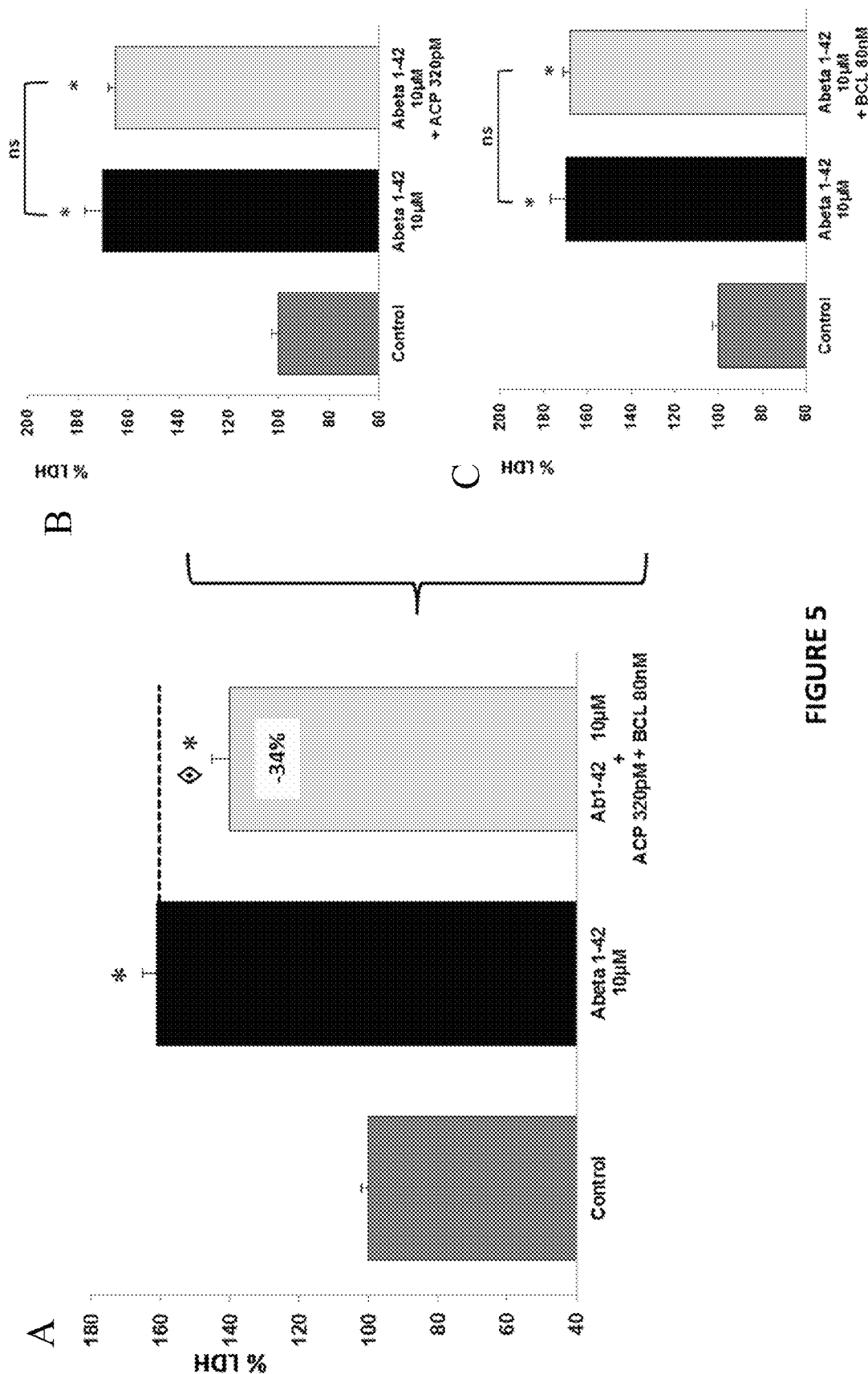
FIGS. 5A-5C: Effect of acamprosate (ACP) and baclofen (BCL) combination therapy on LDH release in human $A\beta_{1-42}$ toxicity on rat primary cortical cells. The human amyloid peptide ($A\beta_{1-42}$ 10 µM) produces a significant intoxication compared to vehicle-treated neurons. This intoxication is significantly prevented by the combination of acamprosate and baclofen (A) whereas, at those concentrations, acamprosate (B) and baclofen (C) alone have no significant effect on intoxication. ◊: $p<0.05$, significantly different from $A\beta_{1-42}$ intoxication; *: $p<0.05$, significantly different from vehicle; "ns" no significant effect. (ANOVA+Dunnett Post-Hoc test).

Lactate Dehydrogenase (LDH) Activity Assay 24 hours after intoxication, the supernatant was taken off and analyzed with Cytotoxicity Detection Kit (LDH, Roche Applied Science, ref: 11644793001, batch: 11800300). This colorimetric assay for the quantification of cell toxicity is based on the measurement of lactate dehydrogenase activity released from the cytosol of dying cells into the supernatant.
Data Processing Data were expressed in percentage of control conditions (no intoxication, no amyloid=100%) in order to express the amyloid injury. All values were expressed as mean+/−SEM (s.e.mean) of the 3 cultures (n=6 wells per condition). Statistical analyses were done on the different conditions (one-way ANOVA followed by the Dunnett's test when it was allowed, Statview software version 5.0).
Results The combination of baclofen and acamprosate induces a significant protective effect against the toxicity of human $A\beta_{1-42}$ peptide (improvement of 34% of cell survival) in primary cortical neuron cells as shown in FIG. 5. The results clearly show that the intoxication by human amyloid peptide ($A\beta_{1-42}$ 10 µM) is significantly prevented by the combination, whereas at those concentrations, baclofen or acamprosate, alone, have no significant effect on intoxication.

Figure 6:
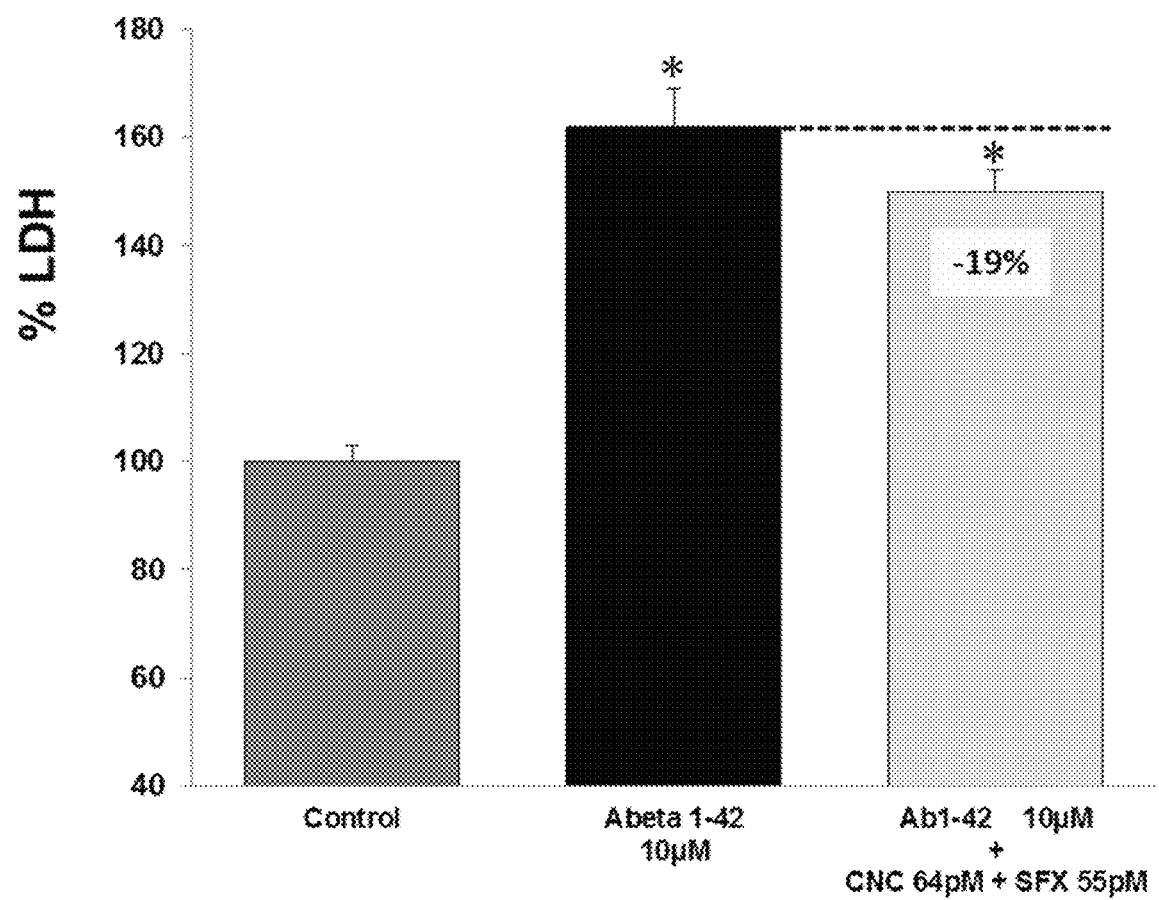
FIG. 6: Effect of cinacalcet (CNC) and sulfisoxazole (SFX) combination therapy on LDH release in human $A\beta_{1-42}$ toxicity on rat primary cortical cells. The human amyloid peptide ($A\beta_{1-42}$ 10 µM) produces a significant intoxication compared to vehicle-treated neurons. This intoxication is prevented by the combination of cinacalcet and sulfisoxazole. *: $p<0.05$, significantly different from vehicle (ANOVA+Dunnett Post-Hoc test).

Conversely, although active in this model, the combination of sulfisoxazole and cinacalcet affords a weaker protection against $A\beta_{1-42}$ (19%, FIG. 6).

Thus, while those two combinations allow a protection against $A\beta_{1-42}$, the combination baclofen—acamprosate stands out clearly. Indeed, at concentrations having no effect alone, the drugs cause a significant protection of primary cortical neuron cells against $A\beta_{1-42}$ when used in combination. Furthermore, the baclofen-acamprosate combination is much more effective than the sulfisoxazole-cinacalcet combination. Such an effect of baclofen and acamprosate represents a remarkable improvement by 60% in comparison to e.g., the effect of the combination of sulfisoxazole and cinacalcet.

Taken together these results show an unexpected and remarkable positive effect of baclofen-acamprosate combinations in several in vitro models of Alzheimer's disease. The effect observed is highly superior to that provoked by other baclofen-based combination therapies (e.g., baclofen-terbinafine), or other active combination therapies (sulfisoxazole-cinacalcet).

Figure 17:
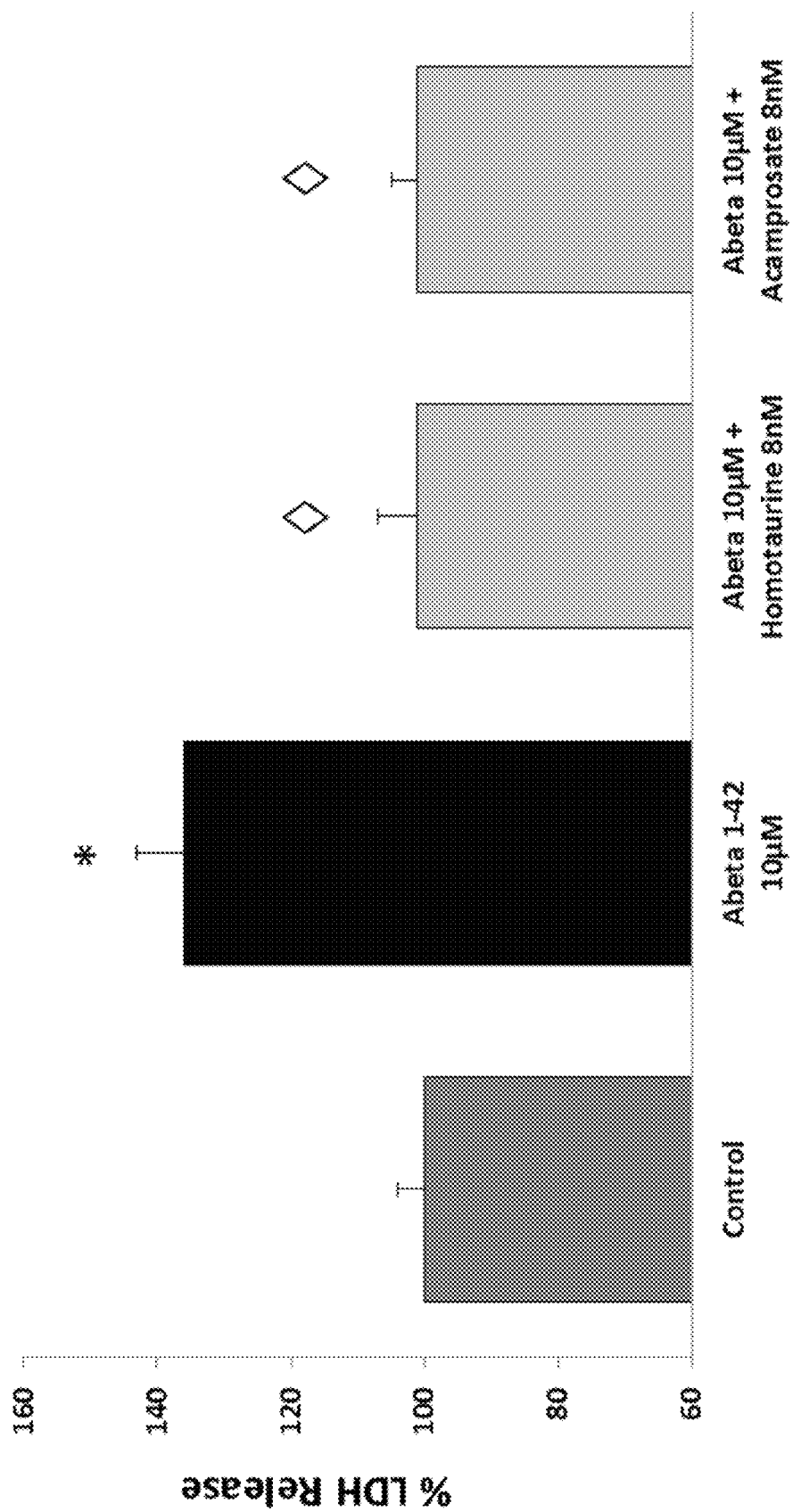
FIG. 17: Comparison of protective effect of acamprosate and its derivative homotaurine pre-treatment in human Aβ$_{1-42}$ toxicity assays on rat primary cortical cells. Aβ$_{1-42}$ produces a significant intoxication compared to vehicle-treated neurons. The intoxication is equally significantly prevented by homotaurine and acamprosate (99%, 8 nM). ◇: p<0.0001: significantly different from Aβ$_{1-42}$ intoxication (ANOVA+Dunnett Post-Hoc test).

A comparison of acamprosate and homotaurine protection activity on cortical cells has been done (FIG. 17). Those results show that the derivative of acamprosate, called homotaurine, allows an effective protection against $A\beta_{1-42}$. In the context of this invention, baclofen or acamprosate can thus be substituted by their derivatives, provided that those derivatives are efficient in assay described herein.

b) Cellular Pathways Triggered in Neurons by Aβ1-42 Oligomers are Reversed Upon Baclofen-Acamprosate Treatment Mitochondrial dysfunction is thought to play a critical role in AD by producing two major cellular consequences: oxidative stress and cell death by apoptosis. The effect of baclofen-acamprosate treatment on oxidative stress and apoptosis generated by Aβ oligomers has been assessed by measuring the oxidation of methionine residues (methionine sulfoxide, MetO) and by measuring the release of mitochondrial cytochrome C (Cyto C, as a marker of early apoptosis) into the cytoplasm of intoxicated neuronal cells. The effect on Aβ induced apoptosis was further confirmed by measuring the level of caspase 3, a marker of late apoptosis.

Figure 21:
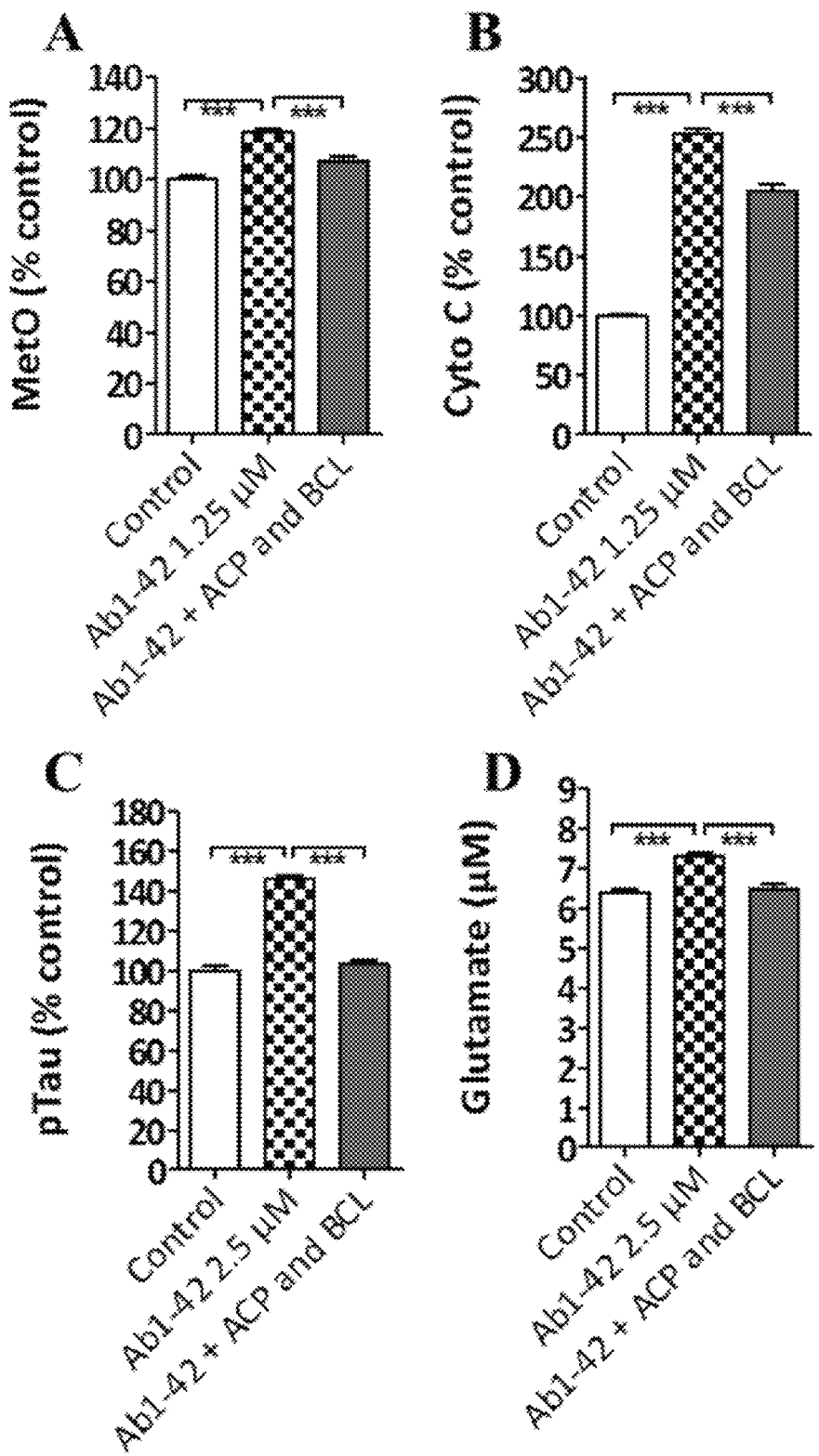
FIGS. 21A-21D: Baclofen-acamprosate combination reduces Aβ$_{1-42}$-induced changes within neurones in vitro. (A) Aβ$_{1-42}$ intoxication induces oxidative stress as shown by the increase of 18% of MetO residues within the cells cultured in presence of Aβ$_{1-42}$ compared to control. Baclofen (0.32 nM) and acamprosate (80 nM) treatment significantly lowers Aβ$_{1-42}$ induced oxidative stress as reported by a drop of 60% of MetO residues in treated, intoxicated, cells. (B) Aβ$_{1-42}$ intoxication results in the triggering of apoptotic events as the increase of cytoplasmic cytochrome C (Cyto C) released from mitochondria (above 150% of control). Baclofen and acamprosate combination significantly reduces of more than 30% the release of mitochondrial Cyto C of intoxicated cells. (C) Aβ$_{1-42}$ intoxication results in an increase of 46% of phosphorylated Tau protein (pTau$^{Ser212/Thr214}$) within the cells, compared to control, non-intoxicated cells. Quantity of phosphorylated Tau protein in Aβ$_{1-42}$ intoxicated neurons is significantly reduced by more than 90% upon treatment with baclofen and acamprosate. (D) baclofen-acamprosate combination diminishes by more than 90% the release of glutamate in the culture medium of Aβ$_{1-42}$-intoxicated cells. Values are mean±s.e.m. ***: p<0.001 versus Aβ (ANOVA+Dunnett Post-Hoc test).

Other hallmarks of AD are i) the accumulation of hyperphosphorylated Tau proteins (pTau) resulting in the formation of neurofibrillary tangles and ii) excitotoxicity due to an excess of glutamate. The effect of baclofen-acamprosate treatment on Tau phosphorylation within Aβ intoxicated neuronal cells and on glutamate accumulation in culture medium was assessed (FIG. 21).

Culture of Primary Cortical Neurons, $A\beta_{1-42}$ Oligomer Formation and Cell Intoxication Cell culture, formation of $A\beta_{1-42}$ oligomer and cell intoxication were mainly performed as above. Variable intoxication times and Aβ concentrations were used depending on the experiment and are summarized in table 3 below.

TABLE 3

| Assay | Days of culture | Seeding density (cells/well) | $A\beta_{1-42}$ Concentration | Intoxication time (h) |
|---|---|---|---|---|
| MetO | 11 | 15,000 | 1.25 µM | 4 |
| Cyto c | 11 | 30,000 | 1.25 µM | 4 |
| Caspase 3 | 11 | 30,000 | 10 µM | 24 |
| Tau phosphorylation | 11 | 30,000 | 2.5 µM | 16 |
| Glutamate release | 13 | 30,000 | 2.5 µM | 4 |

Methionine Sulfoxide (MetO), Cytochrome c (Cyto c), Caspase 3, and Phosphorylated Tau (pTau) Assays:

After $A\beta_{1-42}$ intoxication, cells were fixed, permeabilized, and non-specific sites were blocked with a solution of phosphate buffered saline (PBS; PanBiotech) containing 0.1% of saponin (Sigma) and 1% FCS. Then, cells were incubated with one of the assay specific primary antibodies (Rabbit polyclonal anti MetO, 1/100, Euromedex, France; Rabbit polyclonal anti Cyto c, 1/100, Abcam; Rabbit polyclonal anti Caspase 3, 1/500, Sigma; Mouse monoclonal anti PHF-Tau, clone AT100, 1/100, Thermo Scientific) and with MAP2 primary antibody (Mouse monoclonal anti MAP2, 1/400, Sigma Aldrich or Chicken polyclonal anti MAP2, 1/400, Abcam), which are revealed with the fitting secondary antibodies (Alexa Fluor 488 goat anti mouse IgG; Alexa Fluor 568 goat anti rabbit IgG; Alexa Fluor 568 goat anti chicken IgG, all the three from Invitrogen and used at the 1/400 dilution).

Nuclei were counter-stained with Hoechst (Sigma). For MetO and Cyto c on the one hand, and pTau on the other hand, 20 and 10 pictures with 20× and 40× magnifications respectively were taken per well using the InCell Analyzer™ 1000 (GE Healthcare, France).

Analysis was done using Developer software (GE Healthcare) assessing the overlap between MAP2 on one side, and MetO, Cyto c, Caspase 3 or pTau staining on the other side. Results were expressed as the number of overlapping stained cells per field and reported as a percentage of vehicle treated control.

Glutamate Release Assays:

After 4 h of Aβ1-42 intoxication, cell media supernatants were analysed with Amplex Red Glutamic Acid assay kit (Invitrogen) according to the manufacturer's instructions.
Results Results presented in FIG. 21 show that baclofen-acamprosate combination corrects the major hallmarks of AD. Indeed treatment with baclofen-acamprosate combination leads to a protection against oxidative stress, as demonstrated by a significantly lower content in methionine sulfoxide residues (MetO) in Aβ intoxicated cells treated with baclofen-acamprosate when compared to non-treated intoxicated cells (FIG. 21 A). A marked reduction of the release of mitochondrial cytochrome C is also noticed in baclofen-acamprosate treated Aβ intoxicated cells thereby showing that the combination is efficient in protecting the neuronal cells from Aβ induced apoptosis. (FIG. 21 B). Such effect was confirmed by the observation of a significant lowering of Caspase 3 upon baclofen-acamprosate treatment (not shown). Treatment with baclofen-acamprosate also significantly prevents Tau hyperphosphorylation in $A\beta_{1-42}$-treated neurons (FIG. 21 C), as well as glutamate accumulation in culture medium (FIG. 21 D), a feature mirroring excitotoxicity due to excess of glutamate in AD.

Baclofen-acamprosate combination is thus efficient in counteracting oxidative stress, apoptosis, hyper phosphorylated Tau accumulation, and glutamate excitotoxicity induced in neuronal cells by Aβ oligomers. These surprising properties can, at least in part, account for the observed neuroprotective properties of the composition and for the actual correction of the disease. Such properties are of a particular interest for the treatment of AD and related disorders, but also in the treatment of other neurological disorders which share some of these features with AD. For instance, the control of the events leading to the accumulation of pTau by the administration of baclofen-acamprosate combination is particularly relevant when considering the treatment of Tau pathologies as frontotemporal dementia.

c) Protection Against the Toxicity of $A\beta_{1-42}$ in a Neurite Growth and Synapse Functionality Model.

Culture of Primary Cortical Neurons, $A\beta_{1-42}$ Oligomer Formation and Cell Intoxication Rat cortical neurons were cultured as described by Singer et al. [58]. Briefly pregnant female rats of 15 days gestation were killed by cervical dislocation (Rats Wistar) and the foetuses were removed from the uterus. The cortex was removed and placed in ice-cold medium of Leibovitz (L15) containing 2% of Penicillin 10.000 U/ml and Streptomycin 10 mg/ml and 1% of bovine serum albumin (BSA). Cortices were dissociated by trypsin for 20 min at 37° C. (0.05%). The reaction was stopped by the addition of Dulbecco's modified Eagle's medium (DMEM) containing DNase1 grade II and 10% of foetal calf serum (FCS). Cells were then mechanically dissociated by 3 serial passages through a 10 ml pipette and centrifuged at 515×g for 10 min at +4° C. The supernatant was discarded and the pellet of cells was re-suspended in a defined culture medium consisting of Neurobasal supplemented with B27 (2%), L-glutamine (0.2 mM), 2% of PS solution and 10 ng/ml of BDNF. Viable cells were counted in a Neubauer cytometer using the trypan blue exclusion test. The cells were seeded at a density of 30 000 cells/well in 96 well-plates (wells were pre-coated with poly-L-lysine (10 µg/ml)) and were cultured at +37° C. in a humidified air (95%)/CO2 (5%) atmosphere.

After 10 days of culture, cells are incubated with drugs. After 1 hour, cells are intoxicated by 2.5 µM of beta-amyloid (1-42; Bachem) in defined medium without BDNF but together with drugs. Cortical neurons are intoxicated for 24 hours. BDNF (10 ng/ml) is used as a positive (neuroprotective) control. Three independent cultures were performed per condition, 6 wells per condition.

Neurites Length and Synapse Quantitation

After 24 h of intoxication, the supernatant is taken off and the cortical neurons are fixed by a cold solution of ethanol (95%) and acetic acid (5%) for 5 min. After permeabilization with 0.1% of saponin, cells are blocked for 2 h with PBS containing 1% foetal calf serum. Then, cells are incubated with monoclonal antibody anti microtubule-associated-protein 2 (MAP-2; Sigma) or with anti synaptophysin (SYN, 55798, Sigma) together with anti PSD95 (P246, Sigma) antibodies in order to quantify synapses. These antibodies stain specifically cell bodies and neurites of neurons (MAP2) or pre and post synaptic elements (SYN and PSD95, respectively).

These antibodies are revealed with Alexa Fluor 488 goat anti-mouse IgG (Molecular probe). Nuclei of neurons were labeled by a fluorescent marker (Hoechst solution, SIGMA).

Per well, 10 pictures are taken using InCell Analyzer™ 1000 (GE Healthcare) with 20× magnification. All pictures are taken in the same conditions. Analysis of the neurite network is done using Developer software (GE Healthcare) in order to assess the total length of neurite network.

Results

Figure 7:
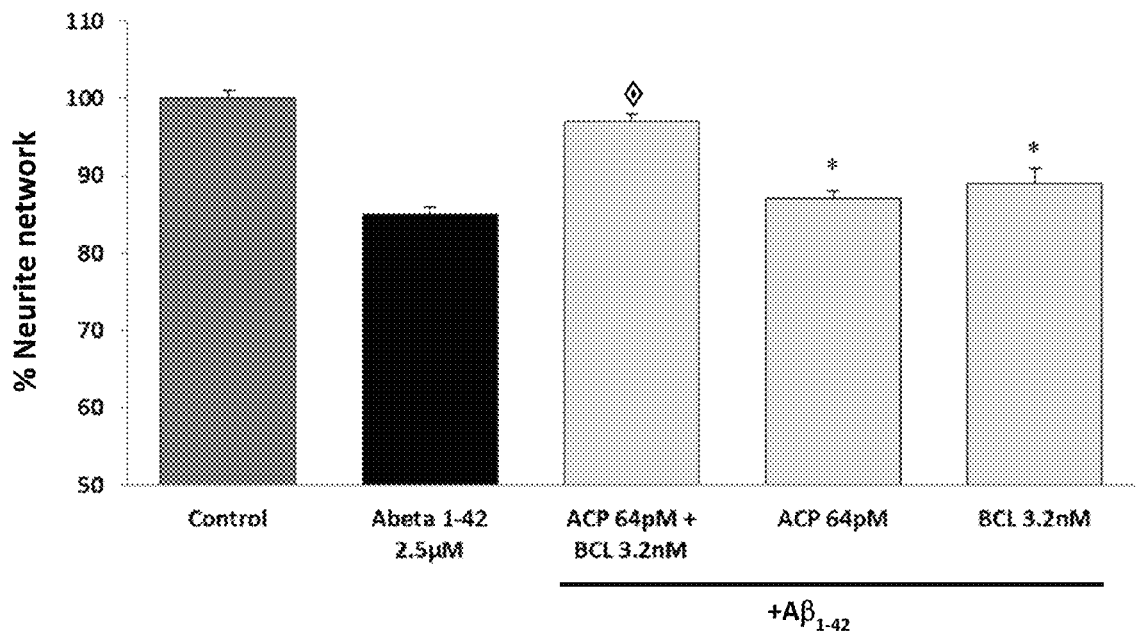
FIG. 7: Effect of acamprosate (ACP) and baclofen (BCL) combination therapy on the total length of neurite network in beta-amyloid intoxicated cortical neurons. The human amyloid peptide ($A\beta_{1-42}$ 2.5 µM) produces a significant intoxication, above 15%, compared to vehicle-treated cells. This intoxication is significantly prevented by the combination of acamprosate and baclofen whereas, at those concentrations, acamprosate and baclofen alone have no significant effect on intoxication. ◊: $p<0.05$, significantly different from $A\beta_{1-42}$ intoxication; *: $p<0.05$, significantly different from vehicle (ANOVA+Dunnett Post-Hoc test).

The combination of baclofen and acamprosate induces a significant protective effect against the toxicity of human $A\beta_{1-42}$ peptide (improvement of 80% of neurites network) in primary cortical neuron cells as shown in FIG. 7. The results clearly show that the intoxication by human amyloid peptide ($A\beta_{1-42}$ 2.5 µM) is significantly prevented by the combination, whereas at those concentrations, baclofen or acamprosate, alone, have no significant effect on intoxication.

Furthermore, the total length of neurite network in primary cortical neuron cells treated with this combination is no more significantly different from control cells. Hence, this combination allows an effective protection of cortical neuron cells against the toxicity of human $A\beta_{1-42}$ peptide but also a neurite growth comparable to a sane cortical neuron cell.

d) Protection of Synapses of Hippocampal Neurons Against the Toxicity of $A\beta_{1-42}$ Oligomer Formation and Cell Intoxication.

Culture of Primary Hippocampal Neurons, $A\beta_{1-42}$ Oligomer Formation and Cell Intoxication Hippocampus brain area is a key player in the building processes of memory; also, hippocampus atrophy is one the most accurate evidence used in the diagnostic of AD. Aβ is known to have a synaptotoxic activity which underlies the early cognitive decline in AD. Ability of combinations of the invention to protect hippocampal neuronal plasticity through protection of synapses from $A\beta_{1-42}$ toxicity have then be evaluated Rat hippocampal neurons were cultured as described by Harrison (1990)[59]. Pregnant females (Wistar, Janvier) at 17 days of gestation were killed by cervical dislocation. Fetuses were collected and immediately placed in ice-cold Leibovitz (L15; Panbiotech) containing 2% of Penicillin 10.000 U/ml and Streptomycin 10 mg/ml (PS; Panbiotech) and 1% of bovine serum albumin (BSA; Panbiotech). Hippocampi were dissociated by trypsin (0.05%, Panbiotech) for 20 min at 37° C. The reaction had been stopped by the addition of Dulbecco's modified Eagle's medium (DMEM; Panbiotech) containing DNAase I grade II (0.5 mg/ml; Panbiotech) and 10% of foetal calf serum (FCS; Invitrogen). Cells were then mechanically dissociated by 3 passages through a 10 ml pipette. Cells were centrifuged at 515 g for 10 min at +4° C. The supernatant was discarded and pellet of cells was re-suspended in a defined culture medium consisting of Neurobasal (Invitrogen) supplemented with B27 (2%; Invitrogen), L-glutamine (2 mM; Panbiotech), 2% of PS solution and 10 ng/ml of Brain-derived neurotrophic factor (BDNF, Panbiotech). Viable cells were counted in a Neubauer cytometer, using the trypan blue exclusion test, then seeded at a density of 20,000 per well in a 96 well-plates pre-coated with poly-L-Lysine (Greiner) and cultured at 37° C. in an air (95%)-CO2 (5%) incubator. The medium was changed every 2 days.

After 18 days of culture, cells were incubated with R/S baclofen and acamprosate combination (80 nM and 0.32 nM respectively). After 2 days of culture, hippocampal neurons were intoxicated with $A\beta_{1-42}$ human peptide (Bachem) at 0.3 µM during 48 hours in presence of the drug combination.

BDNF (50 ng/ml) has been used as positive control and reference compound.

Three separate cultures were performed per condition, 6 wells per condition.

PSD95 and Synaptophysin Immunostaining, Synaptic Loss Quantification.

After 48 hours of intoxication, cells were permeabilized and non-specific sites were blocked with a solution of PBS containing 0.1% of saponin and 1% of FCS for 15 min and then were incubated with mouse monoclonal primary antibody against Post Synaptic Density 95 kDa (PSD95, Abcam) and with rabbit polyclonal primary antibody against Synaptophysin (Sigma) overnight at 4° C. These antibodies were revealed with Alexa Fluor 488 goat anti-mouse (Molecular probe) and Alexa Fluor 568 goat anti-rabbit (Molecular probe) for 1 hour. Nuclei of cells were labelled by a fluorescent marker (Hoechst solution, SIGMA). The total area of PSD95, Synaptophysin and the co-localisation were evaluated. Results were expressed in $\mu m^2$ per field. For each well of culture, 40 pictures per well were taken using InCell Analyzer™ 2000 (GE Healthcare) with 60× magnification. Colocalization of the two labelings correspond to intact synapses. The area was automatically evaluated with Developer system analysis (GE Healthcare). PSD95 and synaptophysin total surface overlap was quantified (in $\mu m^2$) and computed for each condition.

Data were expressed in percentage of control conditions (no intoxication, no $A\beta_{1-42}$=100%) in order to express the amyloid injury. All values were expressed as mean+/−SEM (s.e.mean). Statistical analyses were done on the different conditions (ANOVA followed by Dunnett's test or t-test).

Results

Figure 20:
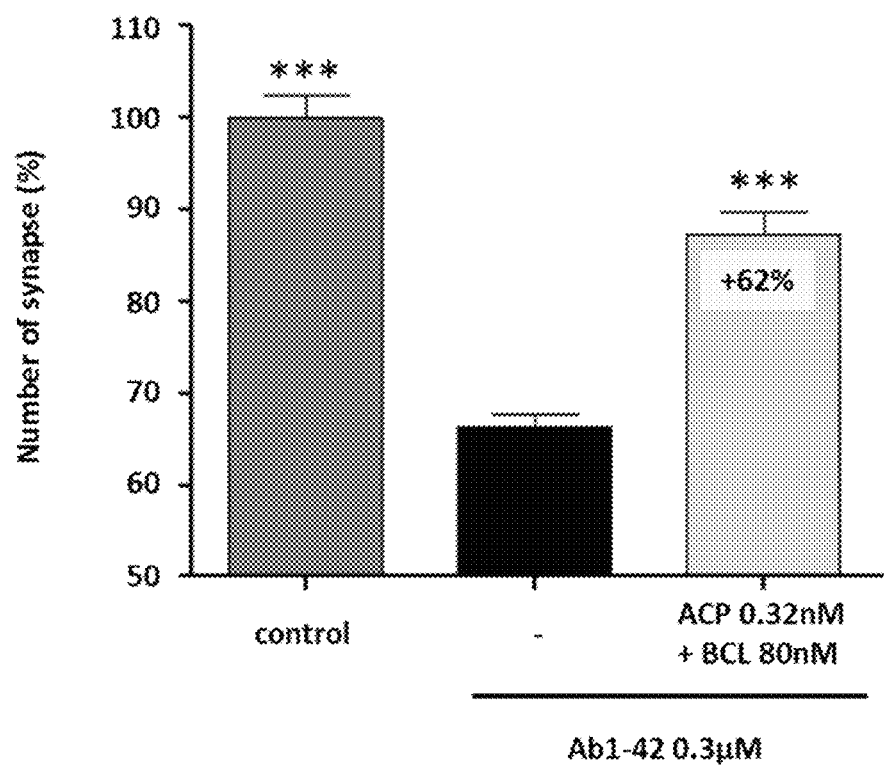
FIG. 20: Baclofen (BCL)-acamprosate (ACP) combination protects synapse integrity from Aβ$_{1-42}$ toxicity. Aβ$_{1-42}$ (0.3 µM) intoxication induces a loss in synaptic junctions between hippocampal neurons (almost 34%), as determined by quantification of colocalization of PSD93 and synaptophysin proteins (black bar). This effect is significantly reversed upon treatment with BCL and ACP combination (80 nM and 0.32 nM respectively) by up to 62% (light grey bar). ***: p<0.001, significantly different from Aβ intoxicated cells.

Results show that $A\beta_{1-42}$ (0.3 μM) intoxication induces a significant lowering of PSD95 and synaptophysin colocalization surface (almost 34%, FIG. 20, black bar) when compared to non-intoxicated cells cultures. Incubation with baclofen-acamprosate (80 nM and 0.32 nM respectively) combination is found to significantly reverse $A\beta_{1-42}$ oligomer toxicity toward synapse junctions: a 62% increase in colocalization area is observed when compared to non-treated cells (FIG. 20, light grey bar). Hence baclofen-acamprosate combination is efficient in maintaining synaptic junctions between hippocampal cells even in the presence of Aβ oligomers.

Baclofen-acamprosate therapy is thus efficient in maintaining synapse function in the presence of Aβ oligomers; together with the neuritis growth protection as mentioned above, this therapy can be thus considered as of particular interest for protecting synaptic plasticity and cellular networking which is impaired in AD.

e) Molecular Targets Important for Baclofen-Acamprosate Mechanism of Action in Neuroprotection Against Aβ Toxicity.

Culture of Primary Cortical Neurons, Ligands Cell Intoxication

Culture of rat primary cortical cells, $A\beta_{1-42}$ peptide preparation and cell intoxication were performed as stated in I.A.2.a). Non-toxic concentrations of CGP54626 (10 μM, GABABR antagonist, Tocris Biosciences), muscimol (1 μM, $GABA_4R$ agonist, Sigma Aldrich), Strychnine (2.5 μM, Glycine receptor antagonist, Tocris Biosciences), (S)-3,5-dihydroxyphenylglycine (DHPG, mGluR1/5 agonist 10 μM, Tocris Biosciences) and (2R,4R)-amino-2,4-pyrrolidinedicarboxylic acid (APDC, mGluR2/3 agonist, 0.3 μM, Sigma Aldrich) were dissolved in 0.1% DMSO (except for DHPG dissolved in water) and added 2 h (except for DHPG, 1 h) before ACP (8 nM) or BCL (400 nM) to 11 days rat primary neuronal cell cultures.

BDNF at 50 ng/ml was used as a positive control.

Cell Survival Evaluation

After 24 hours incubation with $A\beta_{1-42}$ peptide, cortical neurons were fixed by a cold solution of alcohol/acetic acid during 5 minutes. Then, cells were permeabilized and non-specific sites were blocked with a solution of PBS containing 0.1% of saponin (Sigma) and 1% of fetal calf serum for 15 min. Cells were then incubated with mouse monoclonal primary Microtubule-associated protein 2 antibody (MAP-2, Sigma) for 2 hours in the same solution at the dilution of 1/400. An incubation of 1 hour with Alexa Fluor 488 goat anti-mouse (Molecular probe) at 1/400 as a secondary antibody was thereafter performed. Nuclei of cells were labelled by a fluorescent marker (Hoechst solution, Sigma).

The total neuronal survival was evaluated by numbering MAP-2 positive neuronal cell bodies. Ten pictures per well of culture were taken using InCell Analyzer™ 2000 (GE Healthcare) with 20× magnification. The number of neurons was automatically evaluated with Developer system analysis (GE Healthcare).

Data are expressed in percentage of control conditions (no intoxication, no amyloid=100%) in order to express the amyloid injury. All values are expressed as mean+/−SEM (s.e.mean). An ANOVA followed by Dunnett's test was done on each condition.

Results

Data gathered in these experiments show that CGP54626, an orthosteric antagonist of $GABA_B$ receptors, blocks, at non toxic doses, the neuroprotective effect of baclofen (not shown), which confirms the importance of $GABA_B$ receptor activation for the neuroprotective action of baclofen within baclofen-acamprosate combination. In addition, muscimol, an agonist of $GABA_A$ receptors, was found to block the neuroprotective effect of acamprosate (FIG. 22 A), which demonstrates the role of the antagonistic activity of acamprosate on $GABA_A$ receptors for the protection of neuronal cultures against $A\beta_{1-42}$ cytotoxicity. An agonistic effect on ionotropic glycine receptors is also found necessary for neuroprotection since strychnine, an antagonist of inhibitory glycine-gated channels, reverses the neuroprotective effect of the acamprosate (FIG. 22 B). Preincubation with DHPG and APDC, agonists of group I and II metabotropic glutamate receptors respectively, results in the abolition of neuroprotection normally afforded by acamprosate, which demonstrates the importance of the antagonistic effect of acamprosate on these molecular targets for its neuroprotective effect (FIGS. 22 C and D).

From the above, it can be deduced that the particularly effective neuroprotective effect reported for the baclofen-acamprosate combination is the result of a concerted action on, at least, the above 5 molecular targets. Acamprosate is moreover of particularly interest because of its simultaneous actions on at least $GABA_A$ receptors, ionotropic glycine receptors as well as receptors of group I and II metabotropic glutamate receptors which, as demonstrated above, play an essential role in the neuroprotection against Aβ peptide.

3. Concentration Ranges of Baclofen-Acamprosate Combination Affording a Protection in the Three Main Features of Aβ Peptides Toxicity.

As mentioned in the set of the above experiments inventors have found that baclofen and acamprosate combination is efficient in counteracting events triggered by the oligomers of Aβ at the synaptic, at the neuronal and at the endothelial levels.

Figure 23:
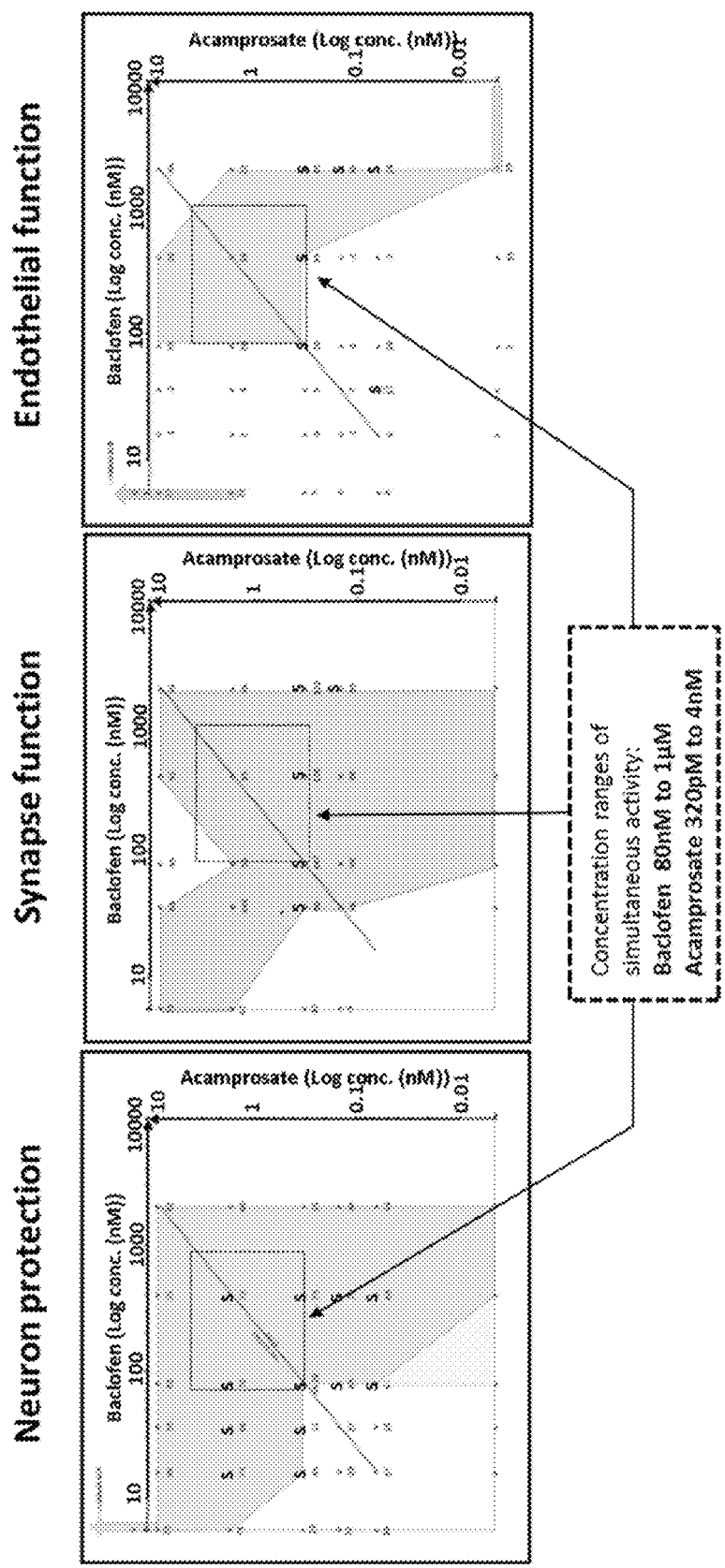
FIG. 23: Simultaneous activity on three main features of AD within given concentration ranges, i.e., baclofen: from 80 nM to 1 µM and acamprosate: from 320 pM to 4 nM. Baclofen-acamprosate combination has been found neuroprotective and improving, at the same time, synapse function (neuron plasticity) and endothelial cells function (angiogenesis). S: drug concentrations at which the combination exerts a synergistic effect in the corresponding in vitro models.

Inventors have been able to determine ranges of concentrations of baclofen and acamprosate that allow an effective protection, at the same time, of neurons, synapse function and endothelial function (FIG. 23). Such a range, for the one a simultaneous activity has been determined for these three features, is found to be from 80 nM to 1 μM for baclofen and from 320 pM to 4 nM for acamprosate.

A particularly enhanced efficacy of the treatment can then be expected within these ranges of concentrations due to the conjunction of effects that is obtained. It can be thus considered that reaching these ranges of plasmatic concentrations of baclofen and acamprosate in the brain is of particular interest.

4. Examples of Synergistic Combinations

Inventors have further found that the baclofen-acamprosate combination is active and shows a marked synergistic effect according methods commonly recognized among pharmacology community [60-62] in at least one of the above in vitro models for AD (Table 4) in the tested concentrations. This ensures a particular clinical benefit. At certain concentrations, the combination provides a synergistic protection in all three models, which is even more particularly advantageous.

TABLE 4

| ACP/BCL (concentration, M) | Combination activity | | |
|---|---|---|---|
| | Angiogenesis | Neuroprotectic | Neuritis network |
| $1.44\ 10^{-10}/2.00\ 10^{-06}$ | Synergy | ¥ | Synergy |
| $1.44\ 10^{-10}/3.60\ 10^{-08}$ | Synergy | Synergy | Synergy |
| $1.44\ 10^{-10}/4.00\ 10^{-07}$ | ǂ | Synergy | Synergy |
| $1.44\ 10^{-10}/8.00\ 10^{-08}$ | Synergy | Synergy | Synergy |
| $3.20\ 10^{-10}/2.00\ 10^{-06}$ | Synergy | ¥ | Synergy |
| $3.20\ 10^{-10}/3.60\ 10^{-08}$ | Synergy | Synergy | Synergy |
| $3.20\ 10^{-10}/4.00\ 10^{-07}$ | Synergy | Synergy | Synergy |
| $3.20\ 10^{-10}/8.00\ 10^{-08}$ | Synergy | Synergy | Synergy |
| $1.60\ 10^{-09}/1.60\ 10^{-08}$ | ǂ | Synergy | NA |
| $1.60\ 10^{-09}/3.60\ 10^{-08}$ | ǂ | Synergy | Synergy |
| $1.60\ 10^{-09}/4.00\ 10^{-07}$ | Synergy | Synergy | Synergy |
| $1.60\ 10^{-09}/8.00\ 10^{-08}$ | Synergy | Synergy | Synergy |
| $6.40\ 10^{-11}/1.60\ 10^{-08}$ | Synergy | Synergy | NA |
| $6.40\ 10^{-11}/2.00\ 10^{-06}$ | Synergy | ¥ | NA |
| $6.40\ 10^{-11}/3.60\ 10^{-08}$ | Synergy | Synergy | NA |
| $6.40\ 10^{-11}/4.00\ 10^{-07}$ | ǂ | Synergy | NA |
| $6.40\ 10^{-11}/8.00\ 10^{-08}$ | Synergy | Synergy | NA |
| $6.40\ 10^{-11}/3.20\ 10^{-09}$ | NA | NA | Synergy |
| $8.00\ 10^{-09}/3.60\ 10^{-08}$ | ǂ | ¥ | Synergy |

Synergy is determined according Loewe or Bliss methods [60-62]

ǂ: no effect;
¥: no synergy;
NA: not available

B. Baclofen-Acamprosate Combination Therapies Prevent Toxicity of Human Aβ in In Vivo Models 1. Intracerebroventricular Administration of $A\beta_{25-35}$ in Swiss Mice.

Animals

Male Swiss mice, 6 weeks old, are used throughout the study. Animals are housed in plastic cages, with free access to laboratory chow and water, except during behavioural experiments, and kept in a regulated environment, under a 12 h light/dark cycle (light on at 8:00 a.m.). Experiments are carried out in a soundproof and air-regulated experimental room, to which mice have been habituated at least 30 min before each experiment.

Combinatory treatment and administration of $A\beta_{25-35}$

Drug(s) is/are daily administered by gavage (per os). The $A\beta_{25-35}$ peptide and scrambled $A\beta_{25-35}$ peptide (control) have been dissolved in sterile bidistilled water, and stored at −20° C. until use. The β-amyloid peptides are then administered intracerebroventricularly (i.c.v.). In brief, each mouse is anaesthetized lightly with ether, and a gauge stainless-steel needle is inserted unilaterally 1 mm to the right of the midline point equidistant from each eye, at an equal distance between the eyes and the ears and perpendicular to the plane of the skull. Peptides or vehicle are delivered gradually within approximately 3 s. Mice exhibit normal behaviour within 1 min after injection. The administration site is checked by injecting Indian ink in preliminary experiments. Neither insertion of the needle, nor injection of the vehicle have a significant influence on survival, behavioral responses or cognitive functions.

On Day −1, i.e. 24 h before the $A\beta_{25-35}$ peptide injection, baclofen, acamprosate, combination thereof or the vehicle solution are administered twice per os by gavage at 8:00 am and 6:00 pm.

On Day 0 (at 10:00 am), mice are injected i.c.v. with $A\beta_{25-35}$ peptide or scrambled $A\beta_{25-35}$ peptide (control) in a final volume of 3 μl (3 mM).

Between Day 0 and Day 7, baclofen, acamprosate, combination thereof or the vehicle solution are administered per os by gavage twice daily (at 8:00 am and 6:00 pm). A dose designated as bid (bis in die) means that said dose is administered twice daily. Drugs are solubilized in water and freshly prepared just before each gavage administration. One animal group receives donepezil (reference compound, 1 mg/kg/day) in a single injection intraperitoneally (at 8:00 am).

On Day 7, all animals are tested for the spontaneous alternation performance in the Y-maze test, an index of spatial working memory.

On Days 7 and 8, the contextual long-term memory of the animals is assessed using the step-down type passive avoidance procedure.

On Day 8, animals are sacrificed. Their brain is dissected and kept at −80° C. for further analysis.

When baclofen-acamprosate combination is tested in a combination with reference compounds for AD (for instance, currently approved treatments for AD are donepezil, galantamine, rivastigmine or memantine) said reference compounds are administered intraperitoneally, between Day 0 and Day 7, at 8:00 am.

a) Combinations Enhance Behavioral and Cognitive Performances of Intoxicated Animals Spontaneous Alternation Performances-Y Maze Test On Day 7, all animals are tested for spontaneous alternation performance in the Y-maze, an index of spatial working memory. The Y-maze is made of grey polyvinylchloride. Each arm is 40 cm long, 13 cm high, 3 cm wide at the bottom, 10 cm wide at the top, and converging at an equal angle. Each mouse is placed at the end of one arm and allowed to move freely through the maze during an 8 min session. The series of arm entries, including possible returns into the same arm, are checked visually. An alternation is defined as entries into all three arms on consecutive occasions. The number of maximum alternations is therefore the total number of arm entries minus two and the percentage of alternation is calculated as (actual alternations/maximum alternations)×100. Parameters include the percentage of alternation (memory index) and total number of arm entries (exploration index). Animals that show an extreme behavior (Alternation percentage <25% or >85% or number of arm entries <10) are discarded. Usually, it accounts for 0-5% of the animals. This test incidentally serves to analyze at the behavioral level the impact and the amnesic effect induced in mice by the $A\beta_{25-35}$ injection.

Passive Avoidance Test

The apparatus is a two-compartment (15×20×15 cm high) box with one illuminated with white polyvinylchloride walls and the other darkened with black polyvinylchloride walls and a grid floor. A guillotine door separates each compartment. A 60 W lamp positioned 40 cm above the apparatus lights up the white compartment during the experiment.

Scrambled footshocks (0.3 mA for 3 s) could be delivered to the grid floor using a shock generator scrambler (Lafayette Instruments, Lafayette, USA). The guillotine door is initially closed during the training session. Each mouse is placed into the white compartment. After 5 s, the door raises. When the mouse enters the darkened compartment and places all its paws on the grid floor, the door closes and the footshock is delivered for 3 s. The step-through latency, that is, the latency spent to enter the darkened compartment, and the number of vocalizations is recorded. The retention test is carried out 24 h after training Each mouse is placed again into the white compartment. After 5 s the doors is raised, the step-through latency and the escape latency, i.e. the time spent to return into the white compartment, are recorded up to 300 s.

Results

Positive results are observed in behavioural performances and biochemical assays performed 7 days after $A\beta_{25-35}$ peptide i.c.v. injection.

Figure 8:
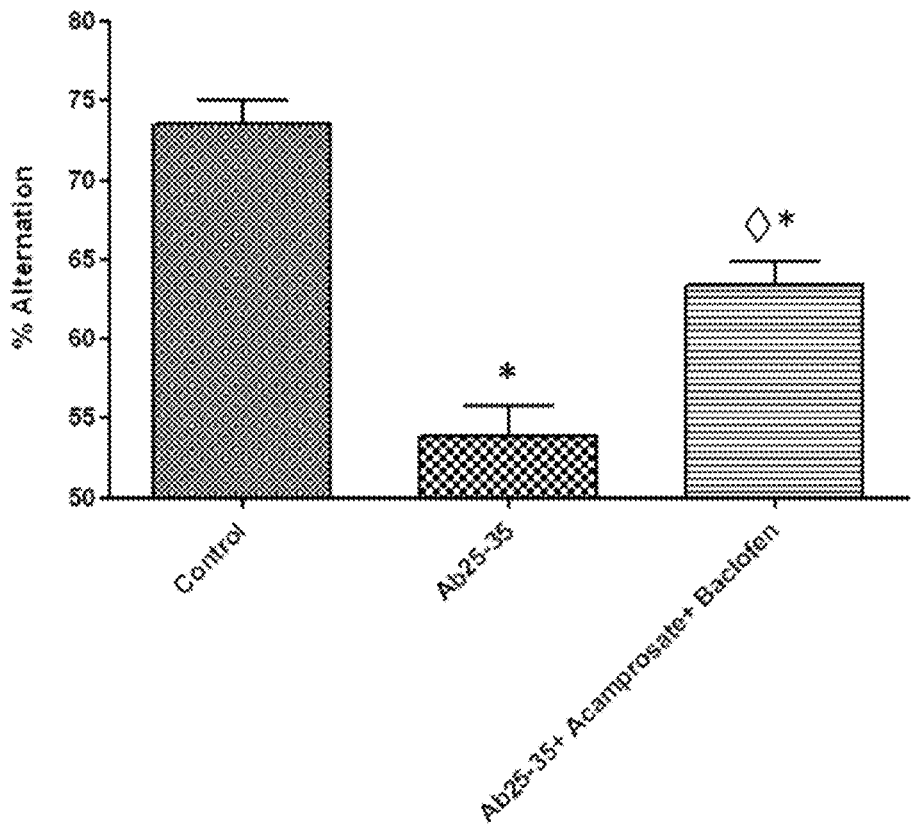
FIG. 8: Effect of acamprosate and baclofen combination therapy on behaviour as defined by Y-maze test. The amyloid peptide produces a significant decrease in cognition as measured by percentage of alternation (53.8% versus 73.5%). This deleterious effect is significantly prevented (48.2% of protection) by the combination of acamprosate (0.2 mg/kg bid) and baclofen (3 mg/kg bid). ◊: $p<0.05$, significantly different from $A\beta_{25-35}$ intoxication; *: $p<0.05$, significantly different from control (ANOVA+Dunnett Post-Hoc test).
Figure 9:
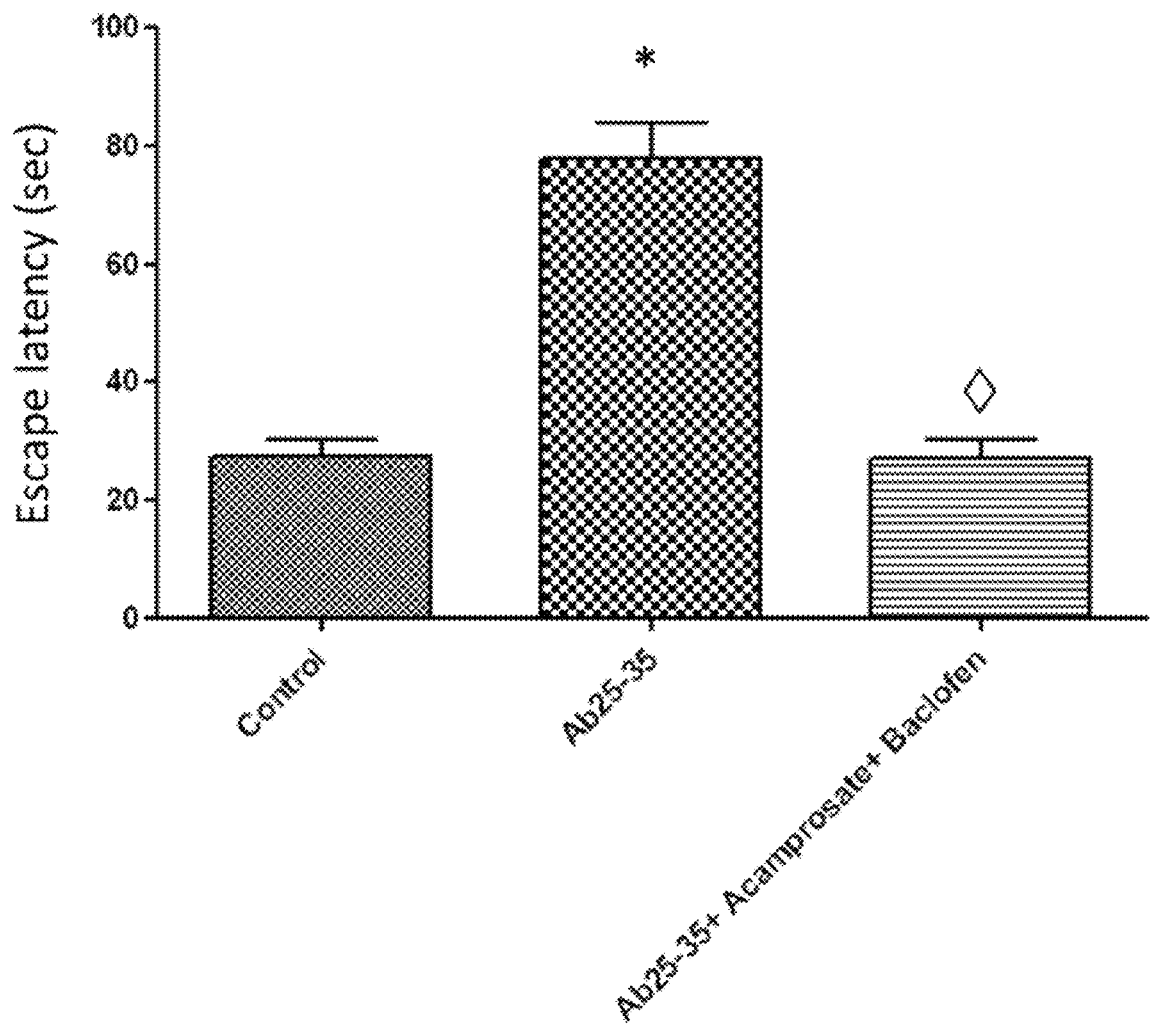
FIG. 9: Effect of acamprosate and baclofen combination therapy on memory as defined by passive avoidance (escape latency). The amyloid peptide produces a significant decrease in memory performances as measured by escape latency compared to control. This deleterious effect is significantly prevented (complete protection) by the combination of acamprosate (0.2 mg/kg bid) and baclofen (3 mg/kg bid). ◊: $p<0.05$, significantly different from $A\beta_{25-35}$ intoxication; *: $p<0.05$, significantly different from control (ANOVA+Dunnett Post-Hoc test).
Figure 10:
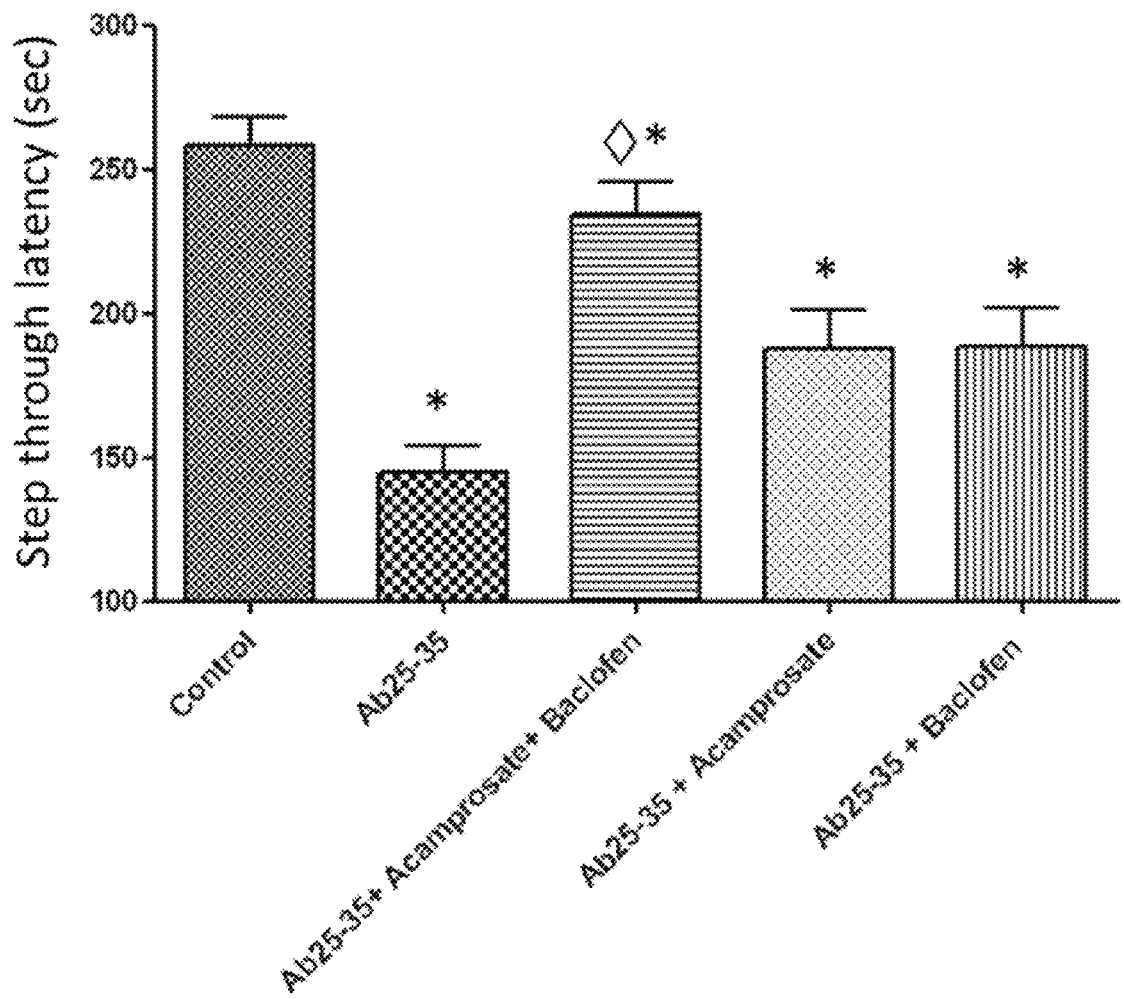
FIG. 10: Effect of acamprosate and baclofen combination therapy on memory as defined by passive avoidance (step-through latency). The amyloid peptide produces a significant decrease in memory performances as measured by step-through latency, above 44%, compared to control. This deleterious effect is significantly prevented (78.8% of protection effect) by the combination of acamprosate (0.2 mg/kg bid) and baclofen (3 mg/kg bid) whereas, at those concentrations, acamprosate and baclofen alone have a lower effect on intoxication. ◊: $p<0.05$, significantly different from $A\beta_{25-35}$ intoxication; *: $p<0.05$, significantly different from control (ANOVA+Dunnett Post-Hoc test).
Figure 11:
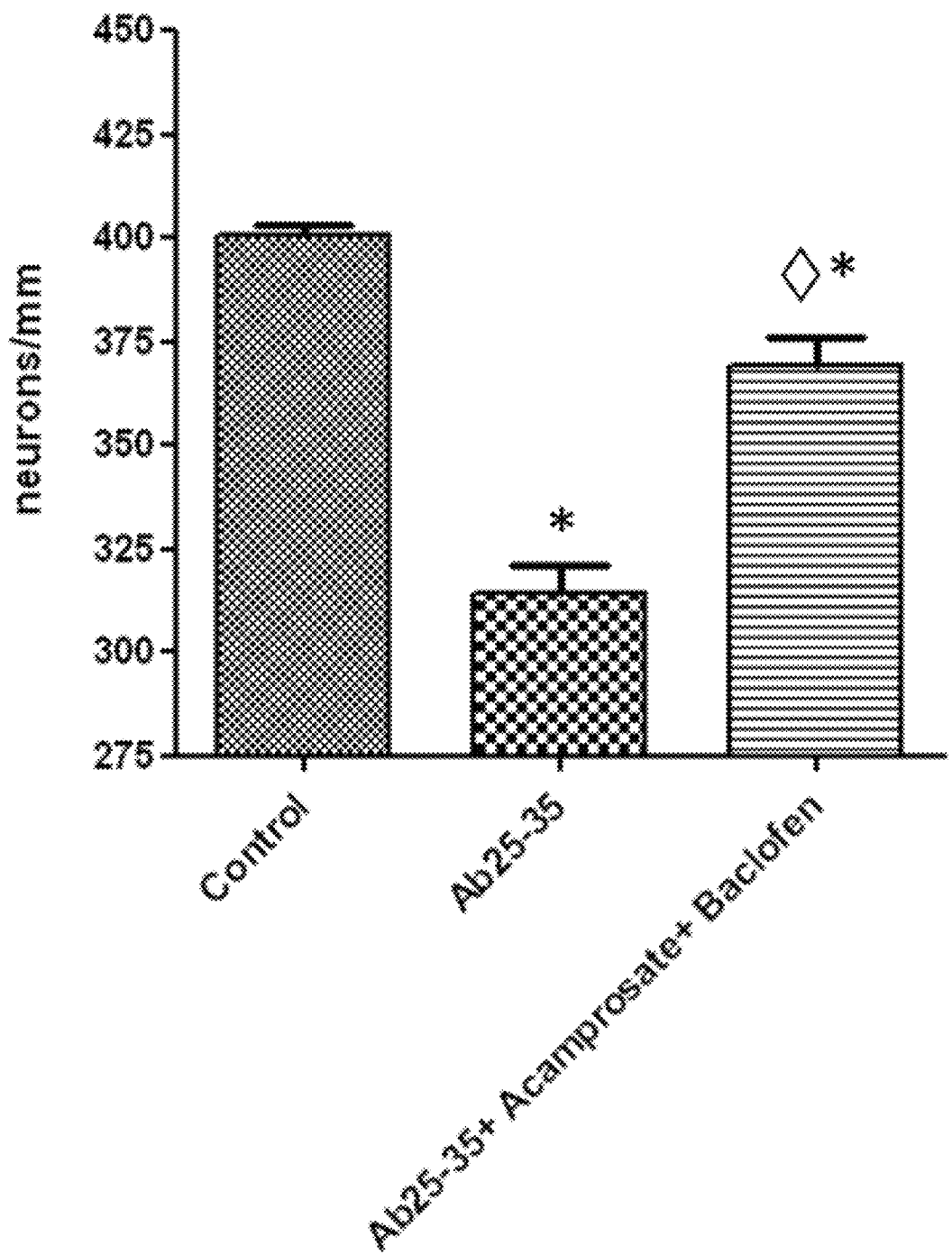
FIG. 11: Effect of acamprosate and baclofen combination therapy on neuron's density in hippocampus. The amyloid peptide produces a significant decrease of neuronal density as measured by the number of neurons per millimeter in hippocampus, above 21%, compared to control. This neuronal injury is significantly prevented (63.2% of injured neurons are protected) by the combination of acamprosate (0.2 mg/kg bid) and baclofen (3 mg/kg bid). ◊: $p<0.05$, significantly different from $A\beta_{25-35}$ intoxication; *: $p<0.05$, significantly different from control (ANOVA+Dunnett Post-Hoc test).

The combination of baclofen and acamprosate induces a significant protective effect on behavioral and cognitive performances of intoxicated animals as shown in FIGS. 8, 9 & 10.

In FIG. 8, with only 53.8% of alternation, intoxicated mice exhibit a strongly impaired spatial working memory compared to control. With an improvement of more than 48% of their percentage of alternation compared to intoxicated control, the impairment is significantly prevented in mice treated with baclofen and acamprosate.

Similarly, FIGS. 9 & 10 show that intoxicated animals exhibit impaired behavioral and cognitive performances according to their score in escape latency and step-through latency respectively. In both tests, the combination of baclofen and acamprosate allows a significant correction of the impairment. The escape latency of mice treated with this combination is no more significantly different from control mice (FIG. 9) and step through latency (FIG. 10) is significantly increased by combinations of the invention with an enhanced effect of the combination compared to drugs alone.

Memory impairment is the early feature of Alzheimer's disease and these results clearly show that the toxic effect of amyloid peptide on behavioral and cognitive performances (including memory) is significantly prevented by the combinations of the invention.

Figure 16:
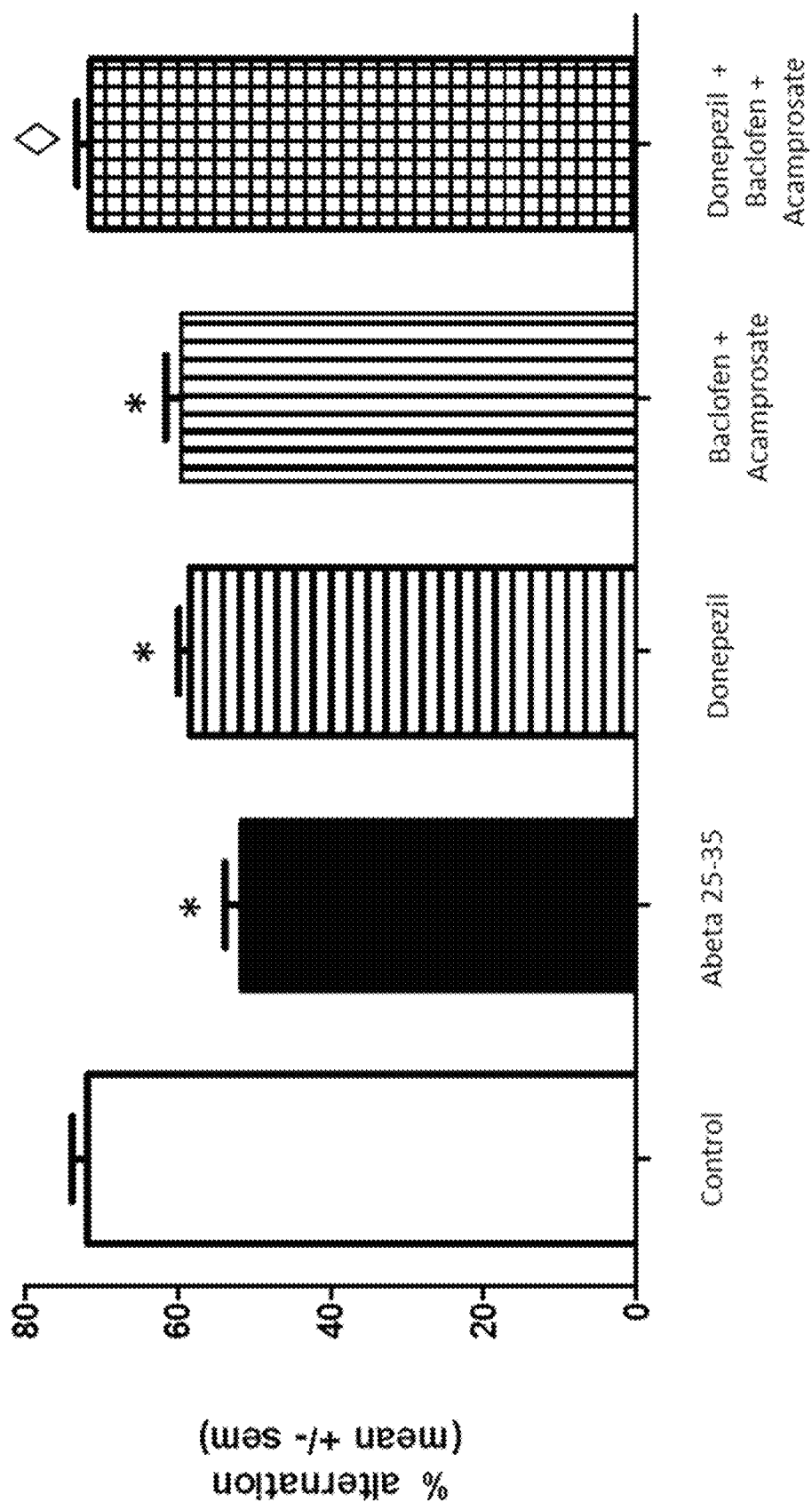
FIG. 16: Effect of donepezil, acamprosate and baclofen combination therapy on behaviour and cognitive performances as defined by Y-maze test. The amyloid peptide produces a significant decrease in cognition as measured by percentage of alternation (51.5% versus 71.8%). This deleterious effect is significantly prevented (98% of protection) by the combination of donepezil (0.25 mg/kg/day), acamprosate (32 µg/kg bid) and baclofen (480 µg/kg bid), whereas at those concentrations drugs alone have no significant effect. ◇: p<0.01, significantly different from Aβ$_{25-35}$ intoxication; *: p<0.01, significantly different from control (ANOVA+Dunnett Post-Hoc test).

Furthermore, the FIG. 16 shows that extremely low dose of baclofen (480 µg/kg bid), acamprosate (32 µg/kg bid) and donepezil (0.25 mg/kg/day) can be combined to allow a complete protection of behavioral and cognitive performances of mice as measured by Y-maze test. Whereas donepezil, at this concentration, has no significant effect (32% protection) on spatial working memory, its use in conjunction with the baclofen and acamprosate combination allows a complete protection (98%) of intoxicated mice's cognitive performances. The combination index of donepezil in combination with baclofen-acamprosate is 0.687 which determines a marked synergy between the compounds (as determined by the method of Loewe [60,61]). The human equivalent dose of donepezil used in this combination is more than 4 times lower than the lowest and almost 20 times lower than the highest dose currently used in human for AD treatment.

Figure 19:
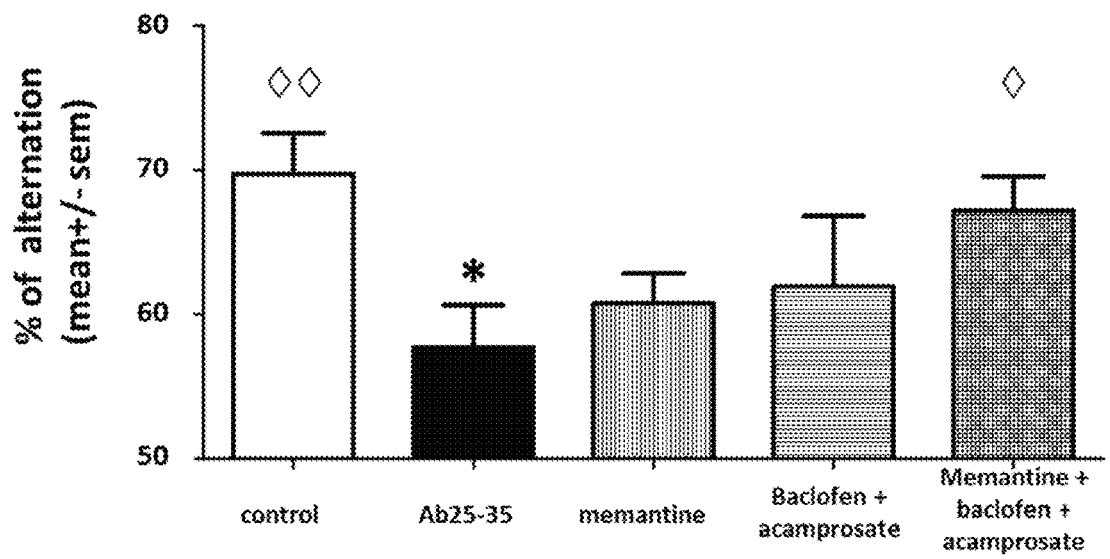
FIG. 19: Effect of memantine, acamprosate and baclofen combination therapy on behaviour and cognitive performances as defined by Y-maze test. The amyloid peptide produces a significant decrease in cognition as measured by percentage of alternation (57.7% versus 69.7%). This deleterious effect is significantly prevented (79.2% of protection) by the combination of memantine (0.5 mg/kg/day), acamprosate (32 µg/kg bid) and baclofen (480 µg/kg bid), whereas at those concentrations drugs alone have no significant effect. ◇ ◇: p<0.01, ◇: p<0.05, significantly different from Aβ$_{25-35}$ intoxication; *: p<0.05, significantly different from control (ANOVA+Dunnett Post-Hoc test).

An improvement is also observed in the performances in Y maze test when combining baclofen (480 µg/kg bid), acamprosate (32 µg/kg bid) and memantine (0.5 mg/kg/day), as shown in FIG. 19. At the concentrations used neither baclofen-acamprosate combination nor memantine has a significant effect. Noteworthy, the dose of memantine used in these experiments is more than 7 times lower than the human equivalent dose corresponding to the maintenance treatment. Moreover the combination of baclofen-acamprosate with memantine is synergistic, displaying a combinatory index of 0.784 (as determined by the method of Loewe [60,61]).

Combinations of the invention can thus be further combined with other therapies for AD in order to potentiate their action, and to lower their potential side effects by using lower doses for these drugs.

b) Combinations Improve Neurophysiological Concern of Neurological Diseases

Combination therapies are tested in an in vivo model of Aβ intoxication. Their effects on several parameters which are affected in neurological diseases are assessed:

Caspases 3 and 9 expression level, considered as an indicator of apoptosis,
Lipid peroxidation, considered as a marker for oxidative stress level,
GFAP expression assay, considered as a marker of the level of brain inflammation,
Brain Blood Barrier integrity,
Overall synapse integrity (synaptophysin ELISA),
Quantification of viable neurons in the *Cornus Ammonis* area1 (CA1) of hippocampus.

Brain Blood Barrier Integrity

Experimental design about animal intoxication by Aβ is the same as previously stated.

The potential protective effect of the combination therapies on the blood brain barrier (BBB) integrity is analyzed in mice injected intracerebroventricularly (i.c.v.) with oligomeric amyloid-β25-35 peptide ($A\beta_{25-35}$) or scrambled $A\beta_{25-35}$ control peptide (Sc.Aβ), 7 days after injection.

On day 7 after the $A\beta_{25-35}$ injection, animals are tested to determine the BBB integrity by using the EB (Evans Blue) method. EB dye is known to bind to serum albumin after peripheral injection and has been used as a tracer for serum albumin. EB dye (2% in saline, 4 ml/kg) is injected intraperitoneal (i.p.) 3 h prior to the transcardiac perfusion. Mice are then anesthetized with i.p. 200 µl of pre-mix ketamine 80 mg/kg, xylazine 10 mg/kg, the chest is opened. Mice are perfused transcardially with 250 ml of saline for approximately 15 min until the fluid from the right atrium becomes colourless. After decapitation, the brain is removed and dissected out into three regions: cerebral cortex (left+right), hippocampus (left+right), diencephalon. Then, each brain region is weighed for quantitative measurement of EB-albumin extravasation.

Samples are homogenized in phosphate-buffered saline solution and mixed by vortexing after addition of 60% trichloroacetic acid to precipitate the protein. Samples are cooled at 4° C., and then centrifuged 30 min at 10,000 g, 4° C. The supernatant is measured at 610 nm for absorbance of EB using a spectrophotometer.

EB is quantified both as:
µg/mg of brain tissue by using a standard curve, obtained by known concentration of EB-albumin.
µg/mg of protein.

Overall Synapse Integrity (Synaptophysin ELISA)

Synaptophysin has been chosen as a marker of synapse integrity and is assayed using a commercial ELISA kit (USCN, Ref. E90425Mu). Samples are prepared from hippocampus tissues and homogenized in an extraction buffer specific to as described by manufacturer and reference literature.

Tissues are rinsed in ice-cold PBS (0.02 mol/l, pH 7.0-7.2) to remove excess blood thoroughly and weighed before nitrogen freezing and −80° C. storage. Tissues are cut into small pieces and homogenized in 1 ml ice-cold phosphate buffer saline (PBS) solution with a glass homogenizer. The resulting suspension is sonicated with an ultrasonic cell disrupter or subjected to two freeze-thawing cycles to further break the cell membranes. Then, homogenates are centrifugated for 5 min at 5,000 g and the supernatant is assayed immediately.

All samples are assayed in triplicates.

Quantification of proteins is performed with the Pierce BCA (bicinchoninic acid) protein assay kit (Pierce, Ref 23227) to evaluate extraction performance and allow normalization.

The total protein concentrations are then calculated from standard curve dilutions and serve to normalize ELISA results.

Quantification of Viable Neurons in the CA1

On Day 8, each mouse is anesthetized with 200 µl i.p. of a pre-mix of ketamine 80 mg/kg and xylazine 10 mg/kg and transcardially perfused with 100 ml of saline solution followed by 100 ml of 4% paraformaldehyde. The brains are removed and kept for 24 h post-fixation in 4% paraformaldehyde solution at 4° C. After post-fixation, brains are washed in a phosphate buffer saline (PBS) solution, then cerebellum is removed and the brains are cut in coronal sections (20 µm thickness) using a vibratom (Leica VT1000S, Leica, Wetzlar, Germany). Serial sections are placed on 24-well plate with PBS. They are then selected to include the hippocampal formation and 9 sections are placed in gelatin-coated glass-strip (one slide per animal for cresyl violet). All slides are dried at room temperature for 48 h to avoid unsticking. The slides are stored at room temperature until cresyl violet staining Sections are stained with 0.2% cresyl violet reagent (Sigma-Aldrich), then dehydrated with graded ethanol, treated with toluene, and are mounted with Mountex medium (BDH Laboratory Supplies, Poole, Dorset, UK).

After mounting, slides are kept at RT for 24 h drying. Examination of the CA1 area are performed using a light microscope (Dialux 22, Leitz), with slices digitalized through a CCD camera (Sony XC-77CE, Sony, Paris, France) with the NIH Image® v1.63 software (NIH). CA1 measurement and pyramidal cells counts are processed using ImageJ® (NIH). Data are expressed as mean of nine slices of CA1 pyramidal cells per millimeter for each group (left and right hippocampus CA1 counting) [63].

Oxidative Stress Assay

Mice are sacrificed by decapitation and both hippocampi are rapidly removed, weighted and kept in liquid nitrogen until assayed. After thawing, hippocampi are homogenized in cold methanol (1/10 w/v), centrifuged at 1,000 g during 5 min and the supernatant placed in eppendorf tube. The reaction volume of each homogenate are added to FeSO4 1 mM, H2SO4 0.25 M, xylenol orange 1 mM and incubated for 30 min at room temperature. After reading the absorbance at 580 nm (A580 1), 10 µl of cumene hydroperoxyde 1 mM (CHP) is added to the sample and incubated for 30 min at room temperature, to determine the maximal oxidation level. The absorbance is measured at 580 nm (A580 2). The level of lipid peroxidation is determined as CHP equivalents (CHPE) according to: CHPE=A580 1/A580 2×[CHP] and expressed as CHP equivalents per weight of tissue and as percentage of control group data.

Caspase Pathway Induction Assay and GFAP Expression Assay

Mice are sacrificed by decapitation and both hippocampi are rapidly removed, rinsed in ice-cold PBS (0.02 mol/l, pH 7.0-7.2) to remove excess blood thoroughly weighted and kept in liquid nitrogen until assayed. Tissues are cut into small pieces and homogenized in 1 ml ice-cold PBS with a glass homogenizer. The resulting suspension is sonicated with ultrasonic cell disrupter or subjected to two freeze-thawing cycles to further break the cell membranes. Then, homogenates are centrifugated at 5,000 g during 5 min and the supernatant is assayed immediately.

Experiments are conducted with commercial assay: Caspase-3 (USCN-E90626Mu), Caspase-9 (USCN-E90627Mu), GFAP (USCN-E90068).

Quantification of proteins is performed with the Pierce BCA (bicinchoninic acid) protein assay kit (Pierce, Ref 23227) to evaluate extraction performance and allow normalization.

Results

The combination of baclofen and acamprosate induces a significant protective effect on neurophysiological functions of intoxicated animals as shown in FIGS. 11, 12, 13 and 14.

Figure 13:
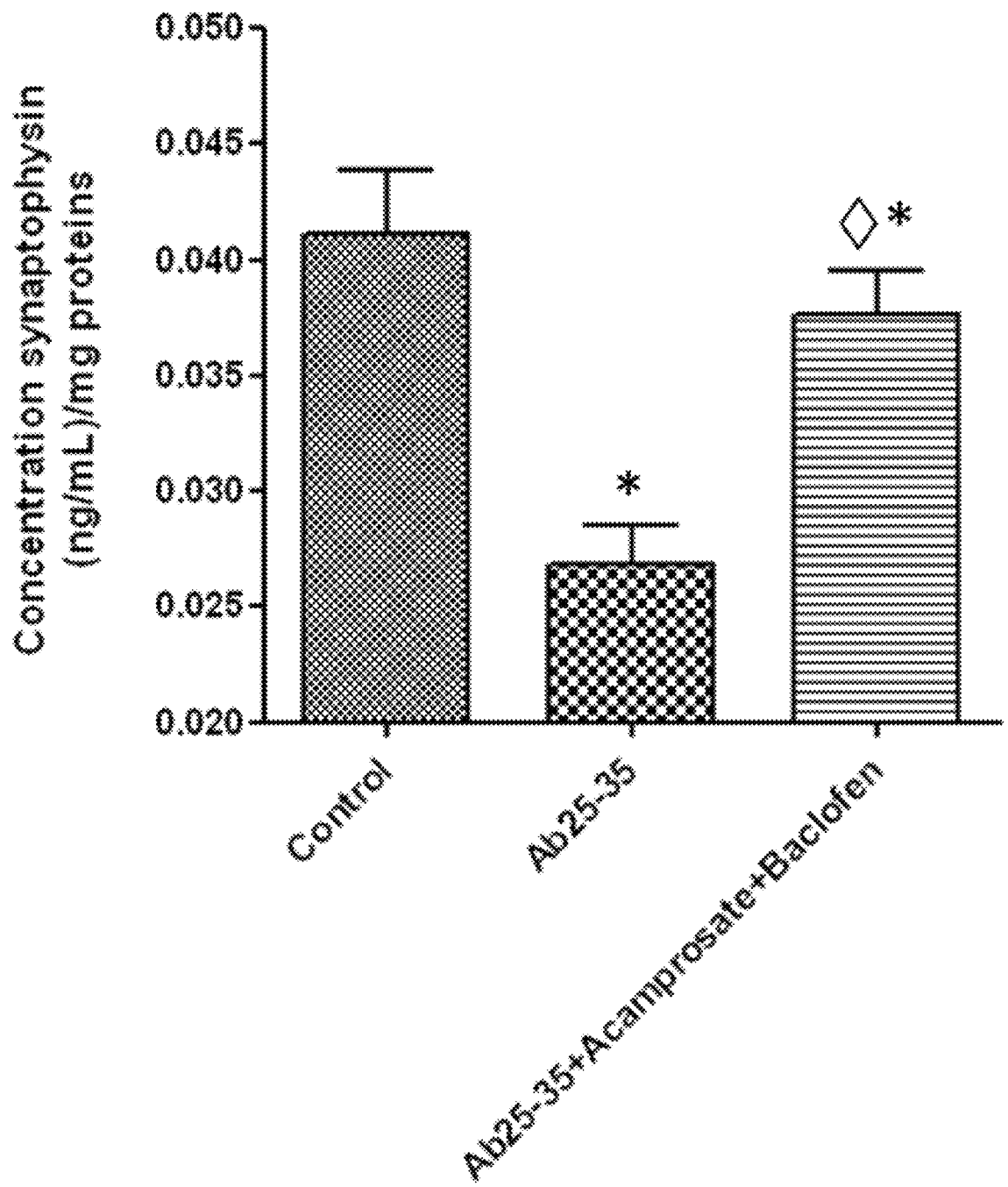
FIG. 13: Effect of acamprosate and baclofen combination therapy on the synaptic density as reflected by the synaptophysin concentration. The amyloid peptide affects the synapse function inducing a significant decrease of the synaptophysin concentration in brain, above 34%, compared to control. Those damages on the synaptic density are significantly prevented (76%) by the combination of acamprosate (0.2 mg/kg bid) and baclofen (3 mg/kg bid). ◊: $p<0.05$, significantly different from $A\beta_{25-35}$ intoxication; *: $p<0.05$, significantly different from control (ANOVA+Dunnett Post-Hoc test).

With a protection of more than 60% compared to non-treated intoxicated animals, the combination is effective for the protection of neurons (FIG. 11) and synaptic density (FIG. 13).

Figure 12:
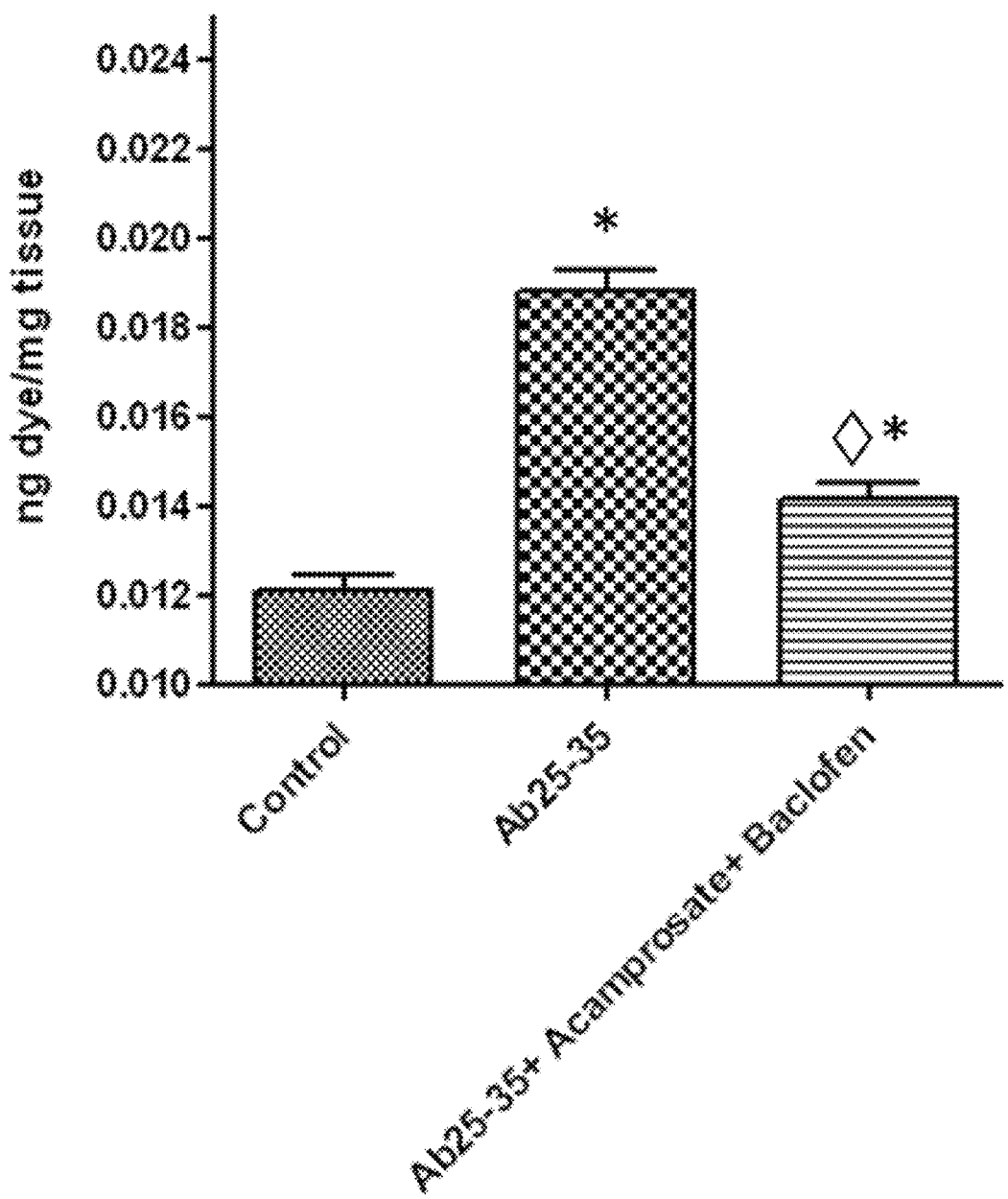
FIG. 12: Effect of acamprosate and baclofen combination therapy on the blood brain barrier (BBB) integrity. The amyloid peptide affect the blood brain barrier inducing a significant increase of its permeability, above 51%, compared to control. Those damages on the blood brain barrier are significantly prevented (66.6% of the integrity restored) by the combination of acamprosate (0.2 mg/kg bid) and baclofen (3 mg/kg bid). ◊: $p<0.05$, significantly different from A◊$_{25-35}$ intoxication; *: $p<0.05$, significantly different from control (ANOVA+Dunnett Post-Hoc test).

Similarly, FIG. 12 shows that the combination of baclofen and acamprosate protects the BBB integrity (76%) compared with non-treated intoxicated animals.

Figure 14:
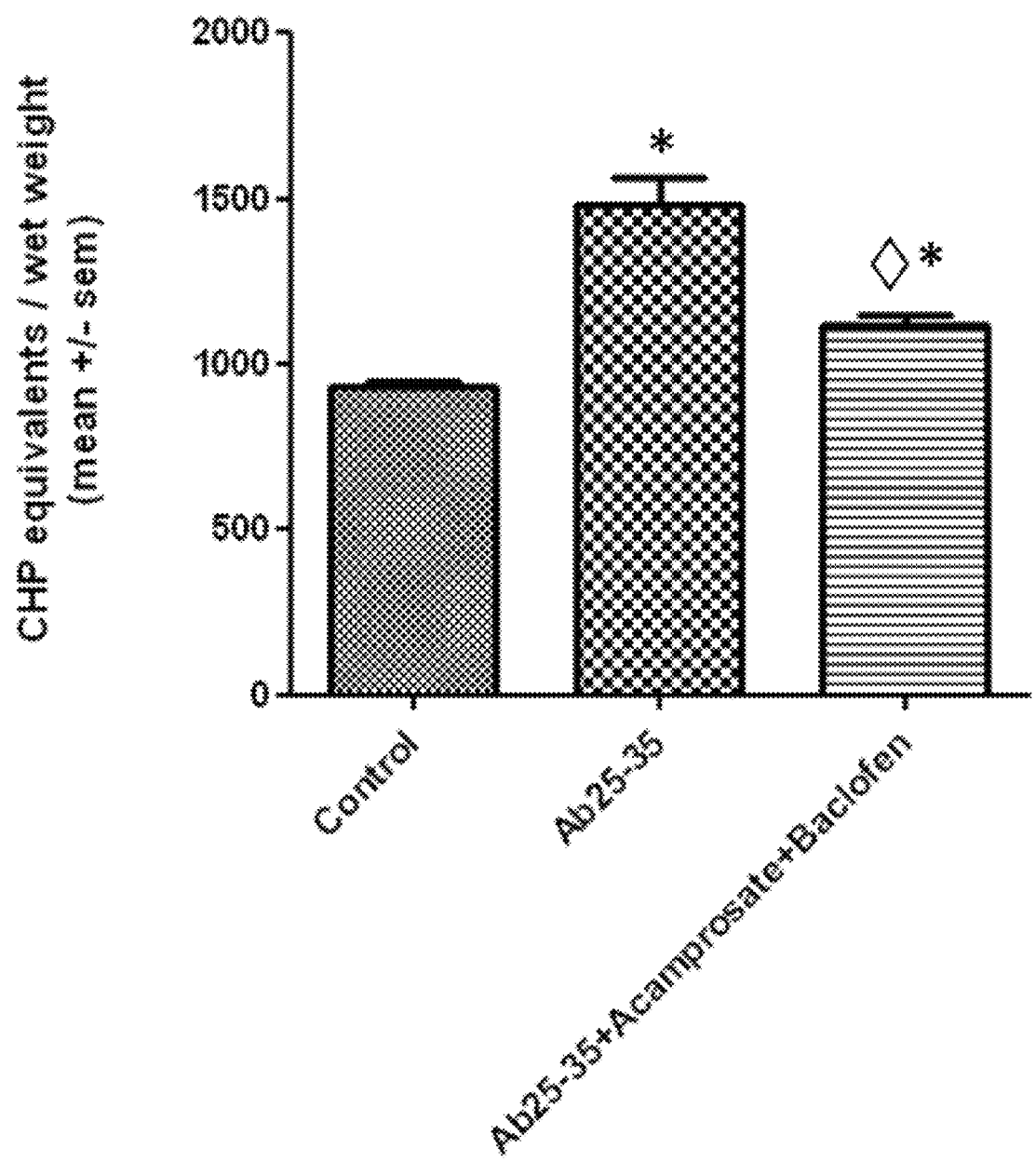
FIG. 14: Protective effect of acamprosate and baclofen combination therapy on the oxidative stress in hippocampus. The amyloid peptide induces a significant increase of oxidative stress in hippocampus as measured by lipid peroxydation, above 59%, compared to control. This oxidative stress is significantly prevented (65.9%) by the combination of acamprosate (0.2 mg/kg bid) and baclofen (3 mg/kg bid). ◇: p<0.05, significantly different from Aβ$_{25-35}$ intoxication; *: p<0.05, significantly different from control (ANOVA+Dunnett Post-Hoc test).

Finally, this combination therapy is efficient in reducing the overall oxidative stress induced by Aβ in brain of treated animals when compared with the non-treated intoxicated animals (FIG. 14).

2. hAPPSL Transgenic Mice

Efficiency of baclofen-acamprosate combination has been tested in another murine model for AD. Mouse line overexpressing the 751 amino acid form of human APP (hAPP) with London (V717I) and Swedish (KM670/671NL) mutations (hAPP$_{SL}$) under the control of the murine Thy-1 promoter has been chosen. In this model, significant deficits in spatial memory and learning in the water maze task and in habituation in the hole-board task are noticed as soon as 6 months of age. This cognitive decline is due to dysfunction of synaptic transmission and mimics some aspects of the early phases of human AD.

Animals

Experiments were conducted on male subjects. Animals were bred at QPS (Austria), and C57BL6 age and gender matched transgenic littermates served as controls. Animals were housed in plastic cages with free access to food and water, except during behavioural experiments, and kept in a regulated environment (23±1° C., 50-60% humidity) under a 12 h light/dark cycle.

Drugs Treatment

Drug combination (acamprosate 0.2 mg/kg and baclofen 3 mg/kg) or the vehicle solution are administered per os by gavage twice daily (at 8:00 am and 6:00 pm) in a volume of 5 ml/kg. Treatment with baclofen-acamprosate combination was started at 8 months of age (i.e. when the disease is well established) and lasted 4 weeks until the end of functional tests. All behavioral tests were performed 2 h after treatment.

Morris Water Maze (MWM) Acquisition Task

Mice were tested for acquisition and working memory. Briefly, swimming was recorded using a Videotrack software (Viewpoint, Champagne-au-Mont-d'Or, France), with trajectories being analysed as latencies and distances. The software divides the pool into four quadrants. Training (Acquisition) consisted in 4 swims per day for 4 days. The latency, expressed as mean±s.e.m., was calculated for each training day. A probe test was performed 24 h after the last swim (retention phase). The platform was removed and each animal was allowed a free 60 s swim. The time spent in each quadrant was then determined. After the training test, animals were tested for spatial working memory. Working memory was specifically assayed by changing the platform location everyday (four swims per day during 2 days) and by using a training inter trial time of 2 min. The swimming times to find platform of first (swim1), second (swim2), third (swim3) and fourth trial (swim4) of Day 2 were calculated and averaged.

Statistical Analyses

A mixed ANOVA with Dunnett's test, including fixed effect terms for treatment, time and the treatment by time interaction, and a random effect term for animals was applied. Treatment effect was assessed each time point and for combined time points (global effect). Tests were conducted at a 5% significance level.

Results

Figure 24:
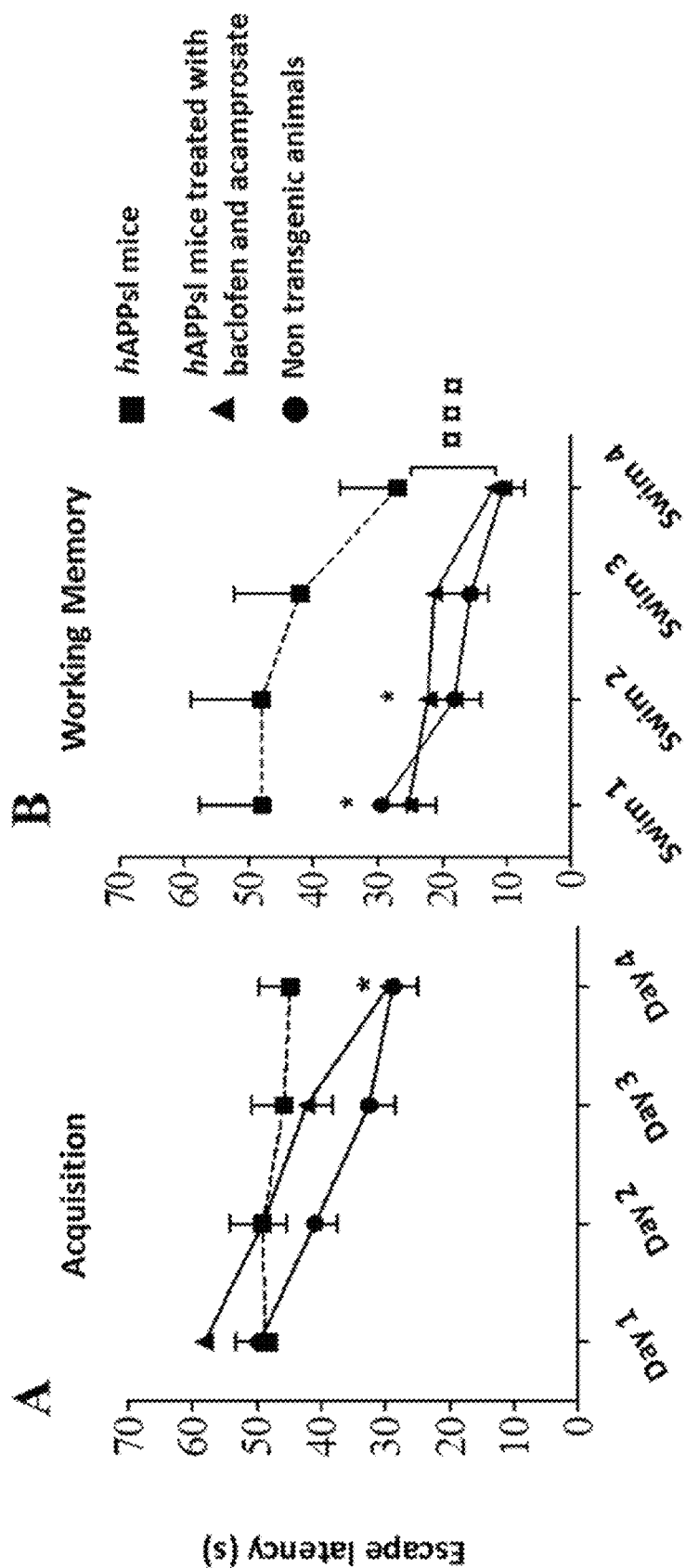
FIGS. 24A-24B: A one month treatment with baclofen-acamprosate combination (acamprosate 0.2 mg/kg bid and baclofen 3 mg/kg bid) is effective in improving cognition in hAPP$_{SL}$ mice of 8 months, when compared to non-treated transgenic mice both during the acquisition phase or the test phase. (A) On day 4 the latency observed for treated transgenic mice is significantly different from that exhibited by non-treated transgenic mice. (B) Escape latency for swim 1 and swim 2 in treated transgenic mice is significantly different from non-treated transgenic mice. Globally performances of all treated transgenic mice are better than those of non-treated transgenic mice and similar to those of non-transgenic animals. Values are mean±s.e.m. *: p<0.05, treated transgenic animals are different from non-treated transgenic animals (ANOVA+Dunnett Post-Hoc test); °°°: p<0.001, Performances of baclofen-acamprosate-treated animals are globally significantly different from performances of non-treated transgenic animals (ANOVA+Dunnett Post-Hoc test).

At the age of 8 months, when $hAPP_{SL}$ transgenic mice cognition was already impaired and diseased installed, a one month treatment with baclofen-acamprosate combination is found to substantially improve cognitive deficits as it has been assessed in MWM acquisition and working memory tests (FIGS. 24 A) and B) respectively).

Thus notwithstanding the extensive in vitro results, the results obtained in two different in vivo models confirm the efficacy of the combination in counteracting the toxicity of Aβ and its behavioural effects as well as its effects on brain physiology.

Several neurological functions, impaired in numerous neurological disorders, including neurodegenerative disorders such as Alzheimer's disease and related disorders have been protected and symptoms retarded or reduced by the combination baclofen-acamprosate.

C. Baclofen-Acamprosate Combination Therapies have Positive Effects in Human Subjects The particular efficiency of the compositions of the invention in different in vitro and animal models for AD, together with the possibility of acting not only on a single but on a group of phenomena described as being at the origin of the disease have prompted the inventors to test it in aged people, in a model of chemically induced amnesia that is commonly used in clinical trials for AD, and also in people suffering from mild AD. More particularly, baclofen-acamprosate combination efficacy in improving memory or memory related mental functions and in improving electrophysiological features underlying working memory has been assessed through clinical trials.

The studies were conducted in compliance with the following study protocols and in accordance with Good Clinical Practice (GCP) as required by the European Medicines Agency ICH-E6 (R1) guideline recommendations and the French law n° 2004-806, Aug. 9, 2004 relative to public health law.

1. Improvement in Memory and Related Functions in Humans Subjected to Chemically Induced Cognitive Impairment.

AD patients show the signs of diminished cholinergic synaptic activity, with diminished levels of acetylcholine. The pharmacological model of this phenomenon consists in treating the subjects with scopolamine, a blocker of muscarinic receptors. This drug thereby induces a transitory and reversible cognitive impairment upon administration [64]; it is therefore currently used as a pharmacologic model for induced dementia.

Experimental Design

Twenty-one healthy male volunteers aged from 20 to 40 years were enrolled in the study which is a randomized, 2-way cross-over, double blind, placebo-controlled study. The study had two distinct periods P1 and P2, each consisting in 40 hours hospitalization and being spaced from each other by 7 days as a wash out period. During these both periods, baclofen-acamprosate combination is administered orally, drugs being administered concomitantly. Results were compared to those of placebo treatment. A dose designated as bid (bis in die) means that said dose is administered twice daily.

During P1, subjects were administered according the following treatment:
 at Day 1: baclofen (6 mg) and acamprosate (0.4 mg) mix, or placebo, orally, in a sub-acute administration, bid
 at Day 2 (test day), H3 just before scopolamine injection: single dose of baclofen (6 mg) and acamprosate (0.4 mg) mix or placebo, orally.
 at Day 2, H3: a sub-cutaneous injection of 0.5 mg of scopolamine.

According to the same above dosage schedule, subjects who had received baclofen-acamprosate treatment in P1 received placebo during P2, while those administered with placebo in P1 were treated with baclofen-acamprosate mix in P2.

Cognitive Test

Effects on impaired cognition were explored by measuring the following features in the Cognitive Groton Maze Learning Task (GMLT) test:
 the efficiency of performance: mps
 the total number of errors: ter
 the duration of task: dur.

GMLT test was performed for each treatment period on Day 1 (2 training sessions), and on Day 2 (test day) H0, H2.5, H4, H5.5, H7 and H9 and on Day 3 H24.

Data Analyses

The data from GMLT test were pooled together in a "composite" GMLT score. Comparison between treatment groups for the two periods was performed on change from baseline value by using a mixed Analysis of Covariance (ANCOVA) model with SAS® Mixed procedure (http://www.sas.com), including fixed effect terms for period treatment, time and the treatment by time interaction, a random effect term for subject and the baseline value as covariate. Treatment effect was assessed for combined time points (global effect) and for each time point.

Results: Baclofen-acamprosate combination improves the cognitive deficit induced by scopolamine.

For each of the periods P1 and P2, similar data were obtained for each of mps, ter and dur components of the GMLT test. The resulting "composite" GMLT score is presented in FIG. 25.

Figure 25:
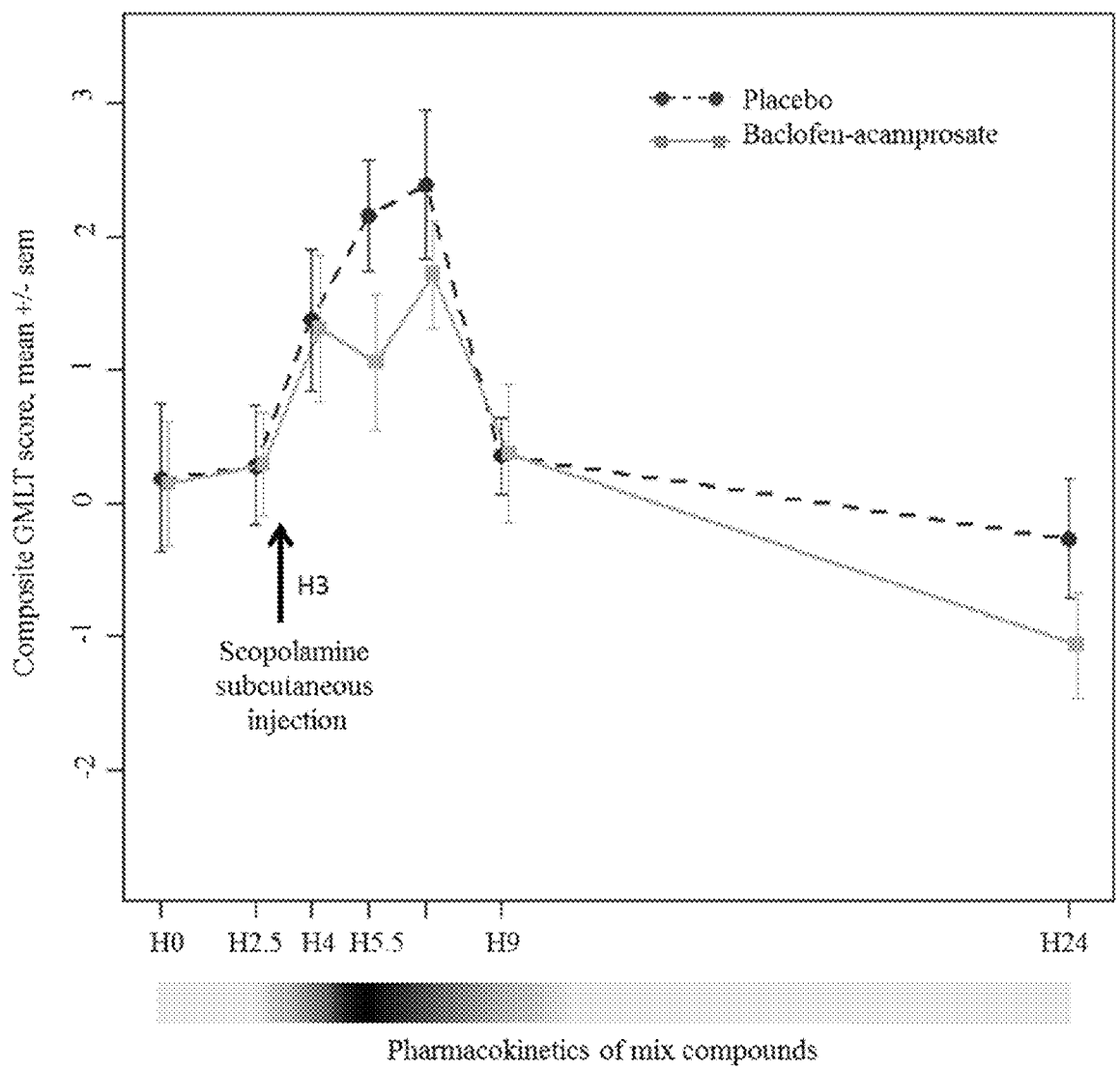
FIG. 25: Baclofen-acamprosate combination efficiently reduces scopolamine induced cognitive impairments in human. Raw data score in Groton Maze Learning Test (GMLT) are plotted along vertical scale. An increase in the score corresponds to an impairment of performances in GMLT. Scopolamine (administered at H3) induces a rapid decrease in cognitive performances in placebo-treated subjects (circles, dotted line) which lasts for approximately 6 hours (H9) after scopolamine injection. Baclofen-acamprosate mix (squares, grey/solid line) is efficient over this period in reducing deleterious effects of scopolamine on the cognitive performances. A significant improvement of cognitive scores is observed in the time window corresponding to the higher plasmatic concentrations of baclofen and acamprosate (shaded bar below the horizontal scale, dark: higher plasmatic concentrations, light: lower plasmatic concentrations).

Scopolamine is known to act as early as 30 min after its administration, its effect lasting for approximately 6 hours. Its Tmax is known to be of about 3 hours [64]. These data correspond to the transient collapse of performances in the GMLT test observed in placebo-treated subjects (FIG. 25, circles, dotted line).

An improvement of cognitive performances was observed for baclofen-acamprosate treated subjects (FIG. 25 squares, grey line) compared to placebo dosed subjects. This improvement is particularly significant in the time period around H5.5 that corresponds to the Tmax of baclofen-acamprosate (FIG. 25, darkest area in the pharmacokinetic scale of mix compounds).

Hence, baclofen-acamprosate combination is efficient in counteracting scopolamine induced cognitive impairment. Hence besides being considered as of interest in the cases of provoked amnesia, combinations of the invention can also be considered as of particular interest in reversing memory impairment related to conditions implying a diminished cholinergic synaptic activity. Baclofen-acamprosate combinations are thus of particular interest for the treatment of AD and related diseases.

2. Baclofen-Acamprosate is Effective in Mild AD Patients.

Another part of the studies performed on human subjects consists in a three months clinical study that is currently performed on patients diagnosed with mild AD with the aim of exploring the effect of baclofen-acamprosate combinations on cognitive and behavioural impairments related to the disease. This study is a 12-week, prospective pilot single-blind and placebo sequential controlled, multi-center trial which assesses the effects of different doses of the baclofen-acamprosate combination. It's a 'challenge/de-challenge/re-challenge' (CDR) type study, which means that baclofen-acamprosate combination is administered on a given time period, then withdrawn, and then re-administered. During the withdraw (de-challenge) phase, the medication is allowed to wash out of the organism. Then, an improvement of the disease's symptoms during challenge and re-challenge phases together with no improvement or a worsening in the de-challenge phase would be considered as a signature of the efficiency of the combination. This study is conducted in an open way and was single blind for the patient and the neurophysiologist assessor. Preliminary results obtained for 29 patients are presented herein.

Experimental Design

Cognitive and behavioural impairments of the subjects are measured by psychometric assessments during visits to a neurophysiologist set at the beginning and the end of each the 3 phases of the CDR study:

Visit 1 (V1) holds on the beginning of challenge phase which lasts 4 weeks and at the end of which performances of subjects are evaluated during the visit 2 (V2); then the de-challenge phase of 4 weeks runs and ends with the visit 3 (V3), after which the re-challenge phase lasts 4 weeks more, to be ended by the last evaluation of the subjects by the neurophysiologist during visit 4 (V4). At each of the visit V1-V4, ADAS cog tests (Alzheimer's Disease Assessment Scale-cognitive subscale) are performed to evaluate the changes in cognition performances of the subjects.

In this study, three doses, administered twice daily (once in the morning and once in the evening), of the mix baclofen-acamprosate are tested:

Dose 1: 0.4 mg acamprosate and 6 mg baclofen, given concomitantly

Dose 2: 1 mg acamprosate and 15 mg baclofen, given concomitantly

Dose 3: 20 mg acamprosate and 12 mg baclofen, given concomitantly.

Subject Recruitment 29 patients diagnosed as suffering from mild AD i.e. displaying a Mini Mental State Examination (MMSE) score between 20 and 26 were enrolled in the study (clinical characteristics of the cohort, table 5) for the testing of doses 1 and 2.

TABLE 5

|  | n = 29 patients |
| --- | --- |
| Age +/− sem | 71.8 +/− 1.33 years |
| Gender | 13 Females |
|  | 16 Males |
| MMSE +/− sem | 23.4 +/− 0.389 |
| ADAS Cog. at V1 +/− sem | 11.9 +/− 0.661 | sem: standard error of the mean;
MMSE: Mini Mental State Examination;
ADAS cog: Alzheimer's Disease Assessment Scale-cognitive subscale Depending on the subjects, the screening/recruitment sessions held from 1 to 2 weeks before V1.

At V1, the 29 patients were randomized into two groups:

15 patients in the group 1 receiving the dose 1.

14 patients in the group 2 receiving the dose 2.

ADAS cog score assessed at V1 is taken as the baseline to evaluate changes in performances of the subjects assessed during the subsequent visits V2, V3 and V4.

Each patient is its own control for the 3 successive sequences of the CDR study.

The effect of the mix is assessed on the changes of ADAS cog score at the end of each period in comparison with the previous visit and the treatment periods are compared to the placebo period.

The mean changes from baseline to the end of the first 4 week active treatment period and the mean change observed between each visit are assessed.

The change of each endpoint is measured between each visit:

from baseline (V1) to the end of the first 4-Week active treatment period (V2), from V2 to the end of the 4-Week placebo period (V3), from V3 to the end of the second 4-Week active treatment period (V4), from V1 to V4.

Differences between V1 and V2 or V1 and V4 are statistically tested using a one-tailed paired test of Student at a 10% significance level.

Dosing of Plasmatic Concentrations of Baclofen and Acamprosate

To evaluate the overall exposure of the patients to the drugs, baclofen and acamprosate plasmatic concentration has been measured at the end of the study (V4), in the morning just before drug administration (at an empty stomach, assumed to be the lowest drug concentration) and two hours after the dosing, which roughly corresponds to the Tmax of the drugs (assumed to be the highest concentration). Actual plasmatic concentration of the drugs to which the patient is exposed thus oscillates during the treatment between these lowest and highest drug concentrations.

The plasmatic concentration of a given drug can be determined using any method well known by biopharmacists. Briefly an LC-MS/MS analysis has been performed on samples with the material detailed in table 6, but any equivalent material can be used.

TABLE 6

|  | acamprosate quantification | baclofen quantification |
| --- | --- | --- |
| Chromatograph | Shimadzu LC-20AD liquid chromatography system SIL-20AC-HT autosampler | Shimadzu LC-20AB liquid chromatography system SIL-20AC autosampler |
| Matrix | C18 stationary phase | Phenyl-hexyl stationary phase |
| Mass spectrometer | API5500 (AB-Sciex) | A TSQ Quantum Ultra mass (Thermo Electron Corporation) |
| Electrospray Ionisation mode | Negative | Positive |
| Reference standard | Acamprosate calcium | Baclofen |
| Internal standard | Acamprosate-D12 calcium trihydrate | Baclofen-D4 |

Watson® LIMS 7.2 (Thermo Electron, Philadelphia, Pa.) software was used for regression, calculation, and statistical calculations.

Analyst 1.5.2 (AB-Sciex) and LCQuan 2.5 (Thermo Electron Corporation) software for LC-MS/MS instrument control, data acquisition and integration. Any other software can be used as a function of the mass spectrometer to be used.

Samples are human plasma samples collected during the clinical trial. Blank plasma samples used to prepare calibration.

For acamprosate quantification, sampling volume was 100 μl and proteins have been precipitated, and for baclofen, sampling volume was 200 μl and sample was submitted to solid phase extraction.

Mini Mental State Examination (MMSE) Score

The MMSE is widely used to assess the cognitive functions and the mnesic abilities [65] in the frame of the diagnosis of AD and of the assessment of the severity of the disease. The test comprises a series of 30 questions addressing 5 different areas (orientation, registration, attention calculation, recall, and language) with the final score being graded out of 30 points. A final score below or equal to 26 points corresponds to a dementia diagnosis. Normal scores ranges from 30 to 26, whereas a score between 26 and 20 indicates mild dementia, a score between 19 and 10 indicates moderate dementia, and a score below 10 is considered as indicating severe dementia. A variation of 2 points of the score is usually considered as clinically relevant.

ADAS Cog Score

ADAS cognitive subscale deals with memory, language, construction and praxis orientation and is commonly considered as a standard for the evaluation of mild to moderate AD patients in the clinical trials. It consists of 11 tasks which measure the disturbances of memory, language, praxis, attention and other cognitive abilities which are often referred to as the core symptoms of AD. It generally shows good test-retest and inter-rater reliability and performs satisfactorily against more detailed measures of cognitive function.

Score range varies from 0 to 70. The more mistakes made, the higher is the score. A normal score is defined as a score lower than 10. A 70-point score is a sign of severe dementia [66].

a) Combination Therapies Improve Cognitive Performances of Mild AD Patients.

Results presented herein were obtained from an intermediate analysis of the ADAS cog data for the 24 first subjects that have completed the study who were treated by doses 1 or 2.

Figure 26:
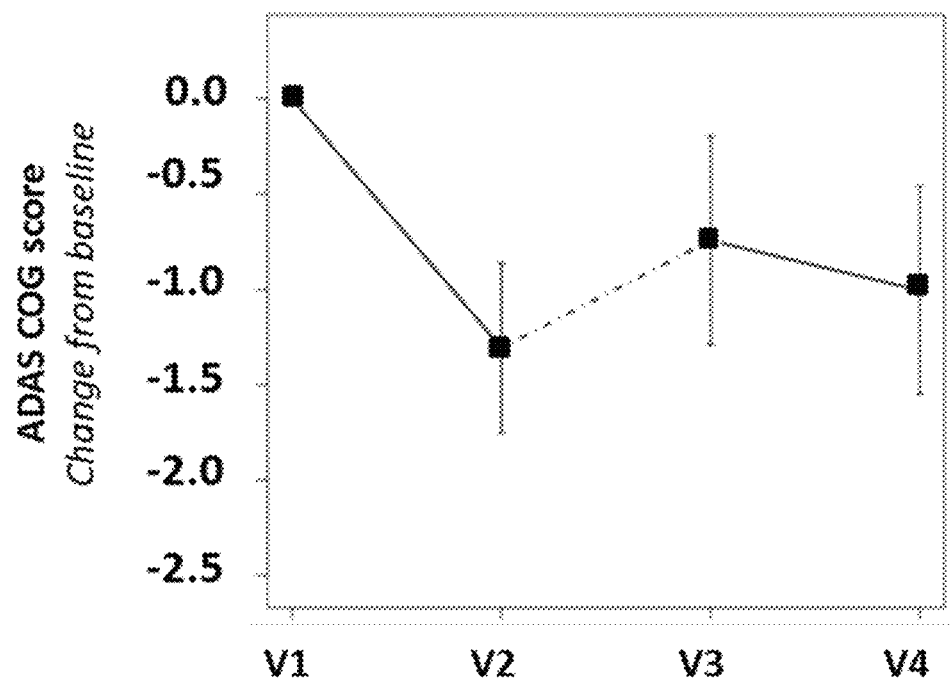
FIG. 26: ADAS-cog (Alzheimer's Disease Assessment Scale Cognitive Subscale) score evolution (change from baseline) during single blind Challenge-De-challenge-Re-challenge (CDR) clinical trial on 24 mild AD subjects. ADAS-cog score is evaluated at the beginning and the end of each period during visits to the neurophysiologist (V). The efficiency of baclofen-acamprosate mix is supported by the clear succession of improvement, worsening and improvement phases in correlation with the challenge (plain line), de-challenge phase (dotted line) and re-challenge phases (plain line). Data are obtained from the gathering of the whole data from dose 1 and dose 2 administered patients. Cognition is significantly improved considering the whole duration of the study (V1 versus V4 score comparison, $p<0.05$); a significant improvement is also noticed at the end of the challenge phase (V1 versus V2 score comparison, $p<0.01$).

As shown in FIG. 26, the evolution of performances in the ADAS cog tests all along the study shows a clear correlation with the CDR design of the study, either when considering the whole set of patients (i.e. whatever the dosage, FIG. 26), or considering separately patients treated with dose 1 or dose 2 (not shown). It appears clearly that the treatment with baclofen-acamprosate during the challenge and re-challenge phases results in an improvement of subject's cognitive performances at the end of both phases when compared to those measured at the beginning of each phase. This positive effect of the treatment is emphasized by the clear worsening of the score during the de-challenge phase, wherein a placebo is administered.

A strongly significant improvement of performances of patients in ADAS cog test is observed between V1 and V2 ($p<0.01$). The three months study led finally to a global significant improvement of patient condition and this despite the dividing de-challenge phase ($p<0.05$).

b) Baclofen-Acamprosate Combination Acts on the Electrophysiological Features of Cognition in Mild AD Patients.

Alterations in brain functions can be detected by electrophysiological techniques as electro encephalography (EEG). Event related potentials (ERPs) are observed within the EEG recordings in response to an experimental condition, and represent the corresponding activated cognitive phenomena such as perception, attention, decision-making process, answering, memory process, language, etc. ERPs characteristics and their components can vary as a function of various factors as stimulus relevance, task performed, lesions of the nervous system, the use of drugs and so on.

ERPs have been found altered in patient suffering from AD, vascular dementia or dementia associated with parkinsonian symptoms. Numerous research studies have helped to establish ERPs as a useful cognitive biomarker for the diagnosis of dementia, tracking disease progression, and evaluating the pro-cognitive effect of therapeutics. More particularly ERPs measures allow pointing out alteration of cognitive function at an early stage, and can contribute to the diagnostic of AD with good sensitivity and specificity.

The most frequently recorded potential in clinical practice is P300 which comprises P3 and N2 subcomponents:

P3 (or late positive complex) is a large centroparietal positivity in the ERP that occurs approximately with a latency of 300 ms after a discordant stimulus. P3 can be divided in the two subcomponents P3a and P3b. P3a is generally considered to be related to the degree of focal attention whereas P3b is supposed to index the working memory update. P3 amplitude notably refers to selective attention stimulus occurrence probability motivation and vigilance.

N2 is a negative wave which precedes P3 and which might be linked to the detection of the target stimulus and be the reflection of the selective attention processes coming into action.

Turning back to AD, a P3b latency increase and amplitude decrease are the most consensual objective parameters observed in AD patients. It is useful for the monitoring of the AD progression, and even for assessing AD treatment response. Generally speaking, latency refers to the time necessary to the making of a decision and amplitude refers to the difficulty of the task, probability of occurrence of the stimulus, or emotional state.

Recording of ERPs

ERPs assessment is done at visits V1-V4 of the above clinical trial.

Recording of cognitive ERPs is done according to the auditory oddball paradigm. Patients lay down on an "examination bed," with eyes opened, in a soundproof, darkened room. Tones (60 dB SPL, 100-ms duration) were presented binaurally through a headset up to a total of 150 stimuli. Patients were instructed to identify the odd 2000 Hz high-pitched stimuli (target sounds), which had a 20% occurrence probability among the standard 1000 Hz low-pitched stimuli (common sounds). The cognitive task required paying attention to the odd stimuli and counting them. The stimulus order of appearance was random and there was at least a 1140-ms gap between each stimulus. Three tests were recorded with a 2-minute pause followed by repeated instructions. The test was stopped once the 90 (3×30) target stimuli have been played out and the patient was asked to give out his/her count of the oddest sounds. Separate averaging of single records corresponding to frequent and rare stimuli were processed on line. Grand average of the evoked potentials was calculated from the three trials for Fz (frontal vertex), Cz (Central vertex) and Pz (Parietal vertex) electrodes.

Evoked potentials amplitudes were measured relative to the prestimulus baseline from the records collected at Fz, Cz and Pz:

P3 was the most positive wave after N2 between 279 and 440 ms.

N100 wave was the most negative peak in the range 75 to 150 ms.

N200 wave was the most negative peak between 196 and 300 ms.

In Alzheimer's disease latencies are hugely delayed and amplitudes are reduced. Latencies and amplitudes of the P3a and P3b subcomponents of P3 and N200 were taken from the signals recorded from Fz, Cz and Pz electrodes and used for statistical analyses. Delta of amplitudes between N2 and P3a, and delta of amplitudes between N2 and P3b were also calculated during statistical analyses. ASCII-format files were also recorded for PCA statistical analyses.

All these 24 latencies/amplitudes/deltas-of-amplitudes parameters and the PCA analysis were assessed for each period (challenge, dechallenge, rechallenge) and compared across all these 3 periods.

The analysis was computed with R. All Quantitative parameters of the ERPs were presented in terms of mean, standard deviation, median, extreme values, Q1, Q3, number of patients and missing data.

Case Study: Baclofen-Acamprosate Combinatorial Treatment Significantly Corrects ERP Features in an AD Subject.

Figure 27:
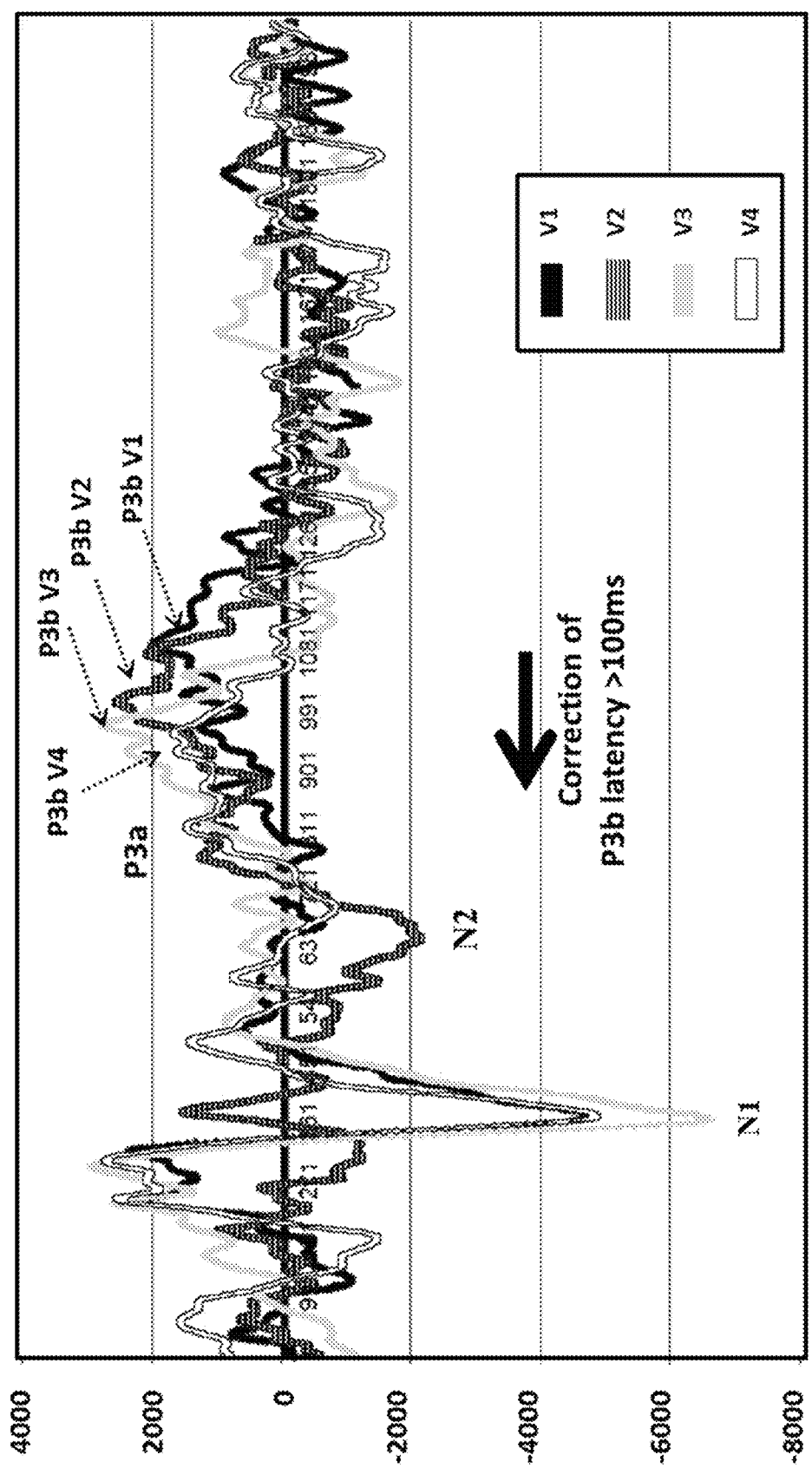
FIG. 27: Records of P300 wave all along the Challenge-De-challenge-Re-challenge (CDR) study, in a subject suffering from mild AD treated with 0.4 mg acamprosate and 6 mg baclofen, each bid. Baclofen-acamprosate combination is efficient in correcting the electrophysiological mechanisms underlying cognitive processes in AD patients. ERPs were recorded at each visit (V1-V4) to the neurophysiologist. Each curve is a modelling of the whole recordings from the different electrodes. It appears clearly that, from V2 to V4, P300 subcomponents wave consistently shift to the left during all the duration of the study, thereby showing a decrease in latency. An improvement of amplitudes is also observed (Student's T-test on paired data).

Results presented in FIG. 27 represents ERP measures gathered from all the three electrodes all along the CDR study for patient 601.

Patient 601 is a 74 years old female Caucasian subject with no known antecedent of familial dementia. She was diagnosed as suffering from probable AD since June 2012, and presents a moderate hypotrophy of hippocampus together with a global cerebral hypotrophy in neuroimaging which ascertains diagnostic. At V0 she obtained a MMSE score of 24. She was administered with the low dosing (dose 1) of the combination.

ERPs obtained at V1 for this patient are characterized by a substantial delay of P3, around 900 ms for this subject (FIG. 27).

As soon as V2, a significant correction of both the delay (a significant decrease) and the amplitude (a significant enhancement) of the P3b wave is noticed. This positive effect of the mix seems to be maintained even during the de-challenge phase: P3b at V3 is found shifted to the left when compared to the one of V2 and presents also a greater amplitude. Improvement of latency is still observed at V4 at the end of the re-challenged phase. These results suggest that the mix is efficient in improving working memory update in AD patients. Noteworthy, an improvement is also observed regarding the P3A and N2 components which are more related to the attention processes.

Hence, baclofen-acamprosate combination is efficient in correcting the alterations of brain electrophysiological functions which are observed in mild AD subjects.

c) Conclusion—Clinical Trial

Results of clinical trials performed in humans show the effectiveness of combinations of the invention in treating AD and related disorders as shown by the observed protection against memory processes degradation both in a chemically induced amnesia model and in patients diagnosed with mild AD. The correction of memory processes in patients is asserted by electrophysiology data that show a correction in brain functioning upon treatment in mild AD patients.

A great variability is commonly observed in plasmatic concentrations of a given drug, in response to the same dosing regimen in different subjects. This can be due notably to variations in the efficiency of metabolism of drugs within each patient. Despite of this, it is noteworthy that during the clinical trial patients have been exposed to plasmatic concentrations of drugs of the same order of magnitude than the concentrations of baclofen and acamprosate that have been shown to, simultaneously, protect neurons from death and to protect synaptic and endothelial functions (table 7).

TABLE 7

|  | Baclofen (ng/ml) | Acamprosate** (ng/ml) |
| --- | --- | --- |
| In vitro ranges for a simultaneous protection of neurons, synaptic and endothelial functions (FIG. 23) | 17.1-213.7 | 0.058-0.725 |
| Plasmatic ranges observed in patients after one month of treatment* | 57.6-261.4 | 0.58-1.20 |

*The lower value corresponds to the mean concentration observed in patients through clinical trial after one month of treatment on an empty stomach, just before administration of the composition, the higher value corresponds to the mean concentration of the drugs observed at Tmax.
**Acamprosate calcium D. Treatment of Age Associated Memory Impairment.

Memory is known as one of the earliest cognitive function to decline through the ageing process in humans and rodents [67, 68].

Inventors have evaluated the efficacy of the compositions of the invention in treating AD related diseases as age associated memory impairment. Working memory performances were evaluated through T-maze alternation test in treated and non-treated animals (roughly the same test as spontaneous alternation in part I.B)1)a)).

Animals—Treatment 24 months old C57L/6J male mice were used. Mice were held on a reversed light cycle. Each experiment has been performed between 8 am and 3 pm and, therefore, under red light condition.

Mice were administered by gavage, twice daily with either combination of the invention (acamprosate 0.2 mg/kg+baclofen 3 mg/kg) or the vehicle solution all along the experiment. Working memory performances of treated and non-treated animals were assayed 17 weeks and 29 weeks after the beginning of the treatment.

On the day of the test, animals were treated 2 hours before the test.

Experimental Procedure

The T-maze apparatus is made of gray Plexiglas with a main stem (55 cm long×10 cm wide×20 cm high) and two arms (30 cm long×10 cm wide×20 cm high) positioned at 90 degree angle relative to the main stem. A start box (15 cm long×10 cm wide) is separated from the main stem by a sliding door. Sliding doors are also provided to close specific arms during the force choice alternation task.

The experimental protocol consists of one single session, which starts with 1 "forced-choice" trial, is followed by 14 "free-choice" trials. In the first "forced-choice" trial, the animal is confined 5 s in the start arm and then it is released while either the left or right goal arm is blocked by closing the sliding door. Then the animal explores the open arm and returns to the start arm. At this point, the animal has completed the forced-choice trial. Immediately after the return of the animal to the start position, the left or right goal door is opened and the animal is allowed to freely choose between the left and right goal arm ("free choice" trials). Each time that the animal has chosen a goal arm, the opposite arm is closed in order to oblige the animal to return to the start arm. Once the animal returns to the start arm, all goal doors are opened to allow another round of free choice trial begins. The animal is considered as entered in a choice arm when it places its four paws in the arm. A session is terminated and the animal is removed from the maze as soon as 14 free-choice trials have been performed or 15 min have elapsed, whatever event occurs first.

The apparatus was cleaned between each animal using alcohol (70°). Urine and feces were removed from the maze.

During the trials, animal handling and the visibility of the operator were minimized as much as possible.

Calculation and Statistical Analysis

The percent spontaneous alternation was calculated as the number of spontaneous alternations divided by the number of free-choice trials. An alternation is defined as a succession of 2 different arms over consecutive choices (e.g., the sequence right-left-right represents 2 alternations).

Analysis of variance (ANOVA) has been performed on the results. Dunnett's test was applied to determine significance of differences.

Results

Figure 28:
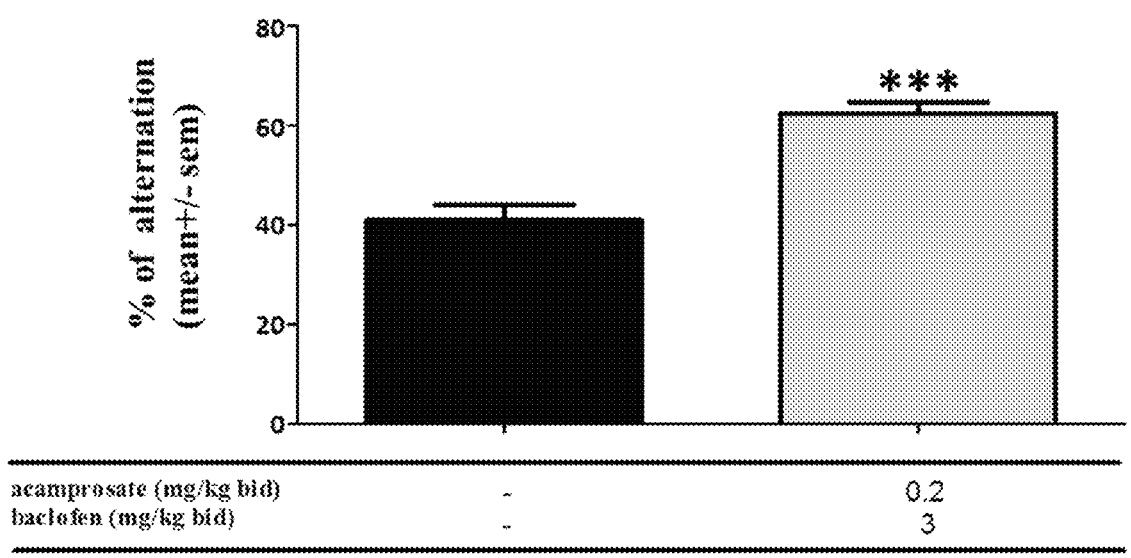
FIG. 28: A 17 weeks treatment with baclofen-acamprosate combination efficiently improves working memory performances of aged mice (of more than 28 months). Percentage of alternation in T-maze test is significantly improved (by more than 50%) in treated aged mice when compared to non-treated mice. Values are mean±s.e.m. ***$p<0.001$, treated aged animals are significantly different from non-treated aged animals (ANOVA+Dunnett Post-Hoc test).

As shown in FIG. 28, composition of the invention significantly improved (by more than 50%) memory of aged mice as soon as 17 weeks after the beginning of the treatment. A significant improvement is also observed after 29 weeks of treatment (not shown). Hence compositions of the invention are also efficient in counteracting AD related disorders as Age Associated Memory Impairment.

II. Treatment of Diseases Related to Glutamate Toxicity a. Prevention of Glutamate Toxicity on Neuronal Cells In Vitro In this further set of experiments, candidate compounds have been tested for their ability to prevent or reduce the toxic effects of glutamate toxicity on neuronal cells. Glutamate toxicity is involved in the pathogenesis of neurological diseases or disorder such as multiple sclerosis, Alzheimer's Disease, frontotemporal dementia, amyotrophic lateral sclerosis, Parkinson's Disease, Huntington's Disease, neuropathies, alcoholism or alcohol withdrawal, or spinal cord injury. The drugs are first tested individually, followed by assays for their combinatorial action.

Methods

The efficacy of drug combinations of the invention is assessed on primary cortical neuron cells. The protocol which is used in these assays is the same as described in section I.A.2 above.

Glutamate Toxicity Assays

The neuroprotective effect of compounds is assessed by quantification of the neurite network (Neurofilament immunostaining (NF), which specifically reveals the glutamatergic neurons).

After 12 days of neuron culture, drugs of the candidate combinations are solved in culture medium (+0.1% DMSO). Candidate combinations are then pre-incubated with neurons for 1 hour before the glutamate injury. One hour after incubation with, glutamate is added for 20 min, to a final concentration of 40 µM, in presence of candidate combinations, in order to avoid further drug dilutions. At the end of the incubation, medium is changed with medium with candidate combination but without glutamate. The culture is fixed 24 hours after glutamate injury. MK801 (Dizocilpinehydrogen maleate, 77086-22-7-20 µM) is used as a positive control.

After permeabilization with saponin (Sigma), cells are blocked for 2 h with PBS containing 10% goat serum, then the cells are incubated with mouse monoclonal primary antibody against Neurofilament antibody (NF, Sigma). This antibody is revealed with Alexa Fluor 488 goat anti-mouse IgG.

Nuclei of cells are labeled by a fluorescent marker (Hoechst solution, SIGMA), and neurite network quantified. Six wells per condition are used to assess neuronal survival in 3 different cultures.

Results

The combination baclofen-acamprosate gives a protective effect against glutamate toxicity for cortical neuronal cells. As exemplified in FIG. 15, combinations of the invention strongly protect neurons from glutamate toxicity under experimental conditions described above. It is noteworthy that an effective protection is noticed using drug concentrations at which drugs used alone have lower protective effect. Combination of baclofen and acamprosate induces an improvement of more than 200% compared to acamprosate alone and more than 47% compared to baclofen used alone.

B. Improvement of Other Disorders Related to Glutamate Excitoxicity Using Combinations of the Invention The above mentioned in vitro protective effect against glutamate toxicity of drugs and drug combinations of the invention combined with the protective effects exemplified herein in several AD models, prompted the inventors to test these drugs and combinations in some models of other diseases in the pathogenesis of which glutamate toxicity is also involved, as MS, ALS and neuropathic pain.

1. Protective Effect of Combinations in an In Vivo Model of Multiple Sclerosis.

A model in which myelin-oligodendrocyte glycoprotein-immunized (MOG-immunized) mice develop chronic progressive EAE is used to demonstrate the beneficial effect of compositions of the invention in multiple sclerosis treatment.

Animals and Chemicals

C57L/6J female mice (8 weeks old) are purchased from Janvier (France); after two weeks of habituation, female mice (10 weeks old) develop chronic paralysis after immunization with MOG (Myelin Oligodendrocyte Glycoprotein) peptide. The experimental encephalomyelitis is induced with the Hooke Kit $MOG_{35-55}$/CFA Emulsion PTX (Pertussis toxin) for EAE Induction (EK-0110, EK-0115; Hooke laboratories). The control kit is CK-0115 (Hooke laboratories).

Experimental Procedure

The experimental encephalomyelitis is induced by following procedure:

The day 0, two subcutaneous injections of 0.1 ml each are performed; one on upper back of the mouse and one in lower back. Each injection contains 100 µg of $MOG_{35-55}$ peptide (MEVGWYRSPFSRVVHLYRNGK, SEQ ID NO:1), 200 µg of inactivated *Mycobacterium tuberculosis* H37Ra and is emulsified in Complete Freund's adjuvant (CFA) (Hooke laboratories). The emulsion provides antigen needed to expand and differentiate MOG-specific autoimmune T cells.

Two intraperitoneal injections of 500 ng of Pertussis toxin in PBS (Hooke kit) are performed 2 hours (Day 0) and 24 hours (Day 1) after the MOG injection. Pertussis toxin enhances EAE development by providing additional adjuvant.

Mice develop EAE 8 days after immunization and stay chronically paralyzed for the duration of the experiment. After the immunization, mice are daily observed for clinical symptoms in a blind procedure. Animals are kept in a conventional pathogen-free facility and all experiments are carried out in accordance with guidelines prescribed by, and are approved by, the standing local committee of bioethics.

Experimental Groups and Drug Treatment:

Groups of female mice as disclosed are homogenized by weight before the immunization:

Control group: vehicle injection in the same conditions of EAE mice (from Day −1 to Day 28, placebo is given daily), EAE group: MOG injection (Day 0)+Pertussis toxin injections (Day 0 and 1)–from Day −1 to Day 28, placebo is given orally daily, EAE+positive control: MOG injection (Day 0)+Pertussis toxin injections (Day 0 and 1)–from Day −1 to Day 28, dexamethazone is given orally daily, EAE+treatment group: MOG injection (Day 0)+Pertussis toxin injections (Day 0 and 1). The treatments start one Day before immunization and last until Day 28. Treatments are applied into two divided doses (i.e. bid).

The clinical scores are measured at Days 0-5-8-9-12-14-16-19-21-23-26-28.

Statistical software (Statsoft Inc.) is utilized throughout for statistical analysis. ANOVA analysis and Student's t test are employed to analyse clinical disease score. P<0.05 is considered significant.

Delays of disease occurrence, clinical score and delay of death, have been compared between each group to the reference "immu" group with Kaplan-Meier curves and a Cox model (R package 'survival'). Resulting p-values are unilateral and test the hypothesis to be better than the reference 'immu' group.

The total clinical score is composed of the tail score, the hind limb score, the fore limb score and the bladder score described as below:

| Tail score: | |
|---|---|
| Score = 0 | A normal mouse holds its tail erect when moving. |
| Score = 1 | If the extremity of the tail is flaccid with a tendency to fall. |
| Score = 2 | If the tail is completely flaccid and drags on the table. |

| Hind limbs score: | |
|---|---|
| Score = 0 | A normal mouse has an energetic walk and doesn't drag his paws |
| Score = 1 | Either one of the following tests is positive:<br>A - Flip test: while holding the tail between thumb and index finger, flip the animal on his back and observe the time it takes to right itself. A healthy mouse will turn itself immediately. A delay suggests hind-limb weakness.<br>B - Place the mouse on the wire cage top and observe as it crosses from one side to the other. If one or both limbs frequently slip between the bars we consider that there is a partial paralysis. |
| Score = 2 | Both previous tests are positive. |
| Score = 3 | One or both hind limbs show signs of paralysis but some movements are preserved; for example: the animal can grasp and hold on to the underside of the wire cage top for a short moment before letting go. |
| Score = 4 | When both hind legs are paralyzed and the mouse drags them when moving. |

| Fore limbs score: | |
|---|---|
| Score = 0 | A normal mouse uses its front paws actively for grasping and walking and holds its head erect. |
| Score = 1 | Walking is possible but difficult due to a weakness in one or both of the paws, for example, the front paws are considered weak when the mouse has difficulty grasping the underside of the wire top cage. Another sign of weakness is head drooping. |
| Score = 2 | When one forelimb is paralyzed (impossibility to grasp and the mouse turns around the paralyzed limb). At this time the head has also lost much of its muscle tone. |
| Score = 3 | Mouse cannot move, and food and water are unattainable. |

| Bladder score: | |
|---|---|
| Score = 0 | A normal mouse has full control of its bladder. |
| Score = 1 | A mouse is considered incontinent when its lower body is soaked with urine. |

The global score for each animal is determined by the addition of all the above mentioned categories. The maximum score for live animals is 10.

Results-Combinations Therapies are Efficient in a MS Model

A significant improvement of global clinical score is observed in "EAE+treatment group" mice for the Baclofen and Acamprosate combination.

Figure 18:
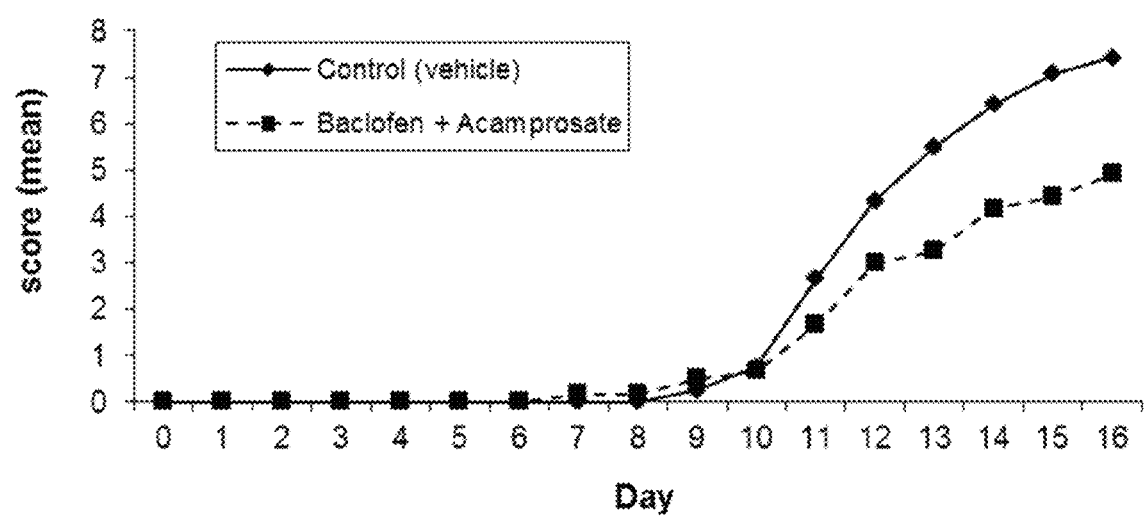
FIG. 18: Effect of acamprosate and baclofen combination therapy on the development of chronic progressive experimental autoimmune encephalomyelitis (EAE) as defined by clinical score. Immunization induces a significant decrease in physical features as measured by clinical score. This deleterious effect is significantly prevented (p-value<0.01) by the combination of acamprosate (2 mg/kg/day) and baclofen (30 mg/kg/day).

The combination of Baclofen (30 mg/kg/day) and Acamprosate (2 mg/kg/day) induced a significant protective effect against the development of chronic progressive EAE and hence confirmed the beneficial effect of the composition in multiple sclerosis treatment (FIG. 18). With more than 30% reduction of the symptoms, the results clearly show that the combination induces a significant reduction of disease development from Day 13. This result confirms the remarkable positive effect of Baclofen-Acamprosate combination on the neuronal protection including on demyelination and its implications.

Taken together, these results show that this combination enables effective protection of neurons against many stresses involved in the development of neurological disease such as β amyloid, BBB breakdown, glutamate excitotoxicity or demyelination.

2) Protective Effects of Combinations in Models of ALS.

The effect of combination therapies according to the present invention on ALS have been demonstrated in vitro, in a co-culture model, and in vivo, in a mouse model of ALS. Protocols and results are presented in this section.

a) Protective Effect Against Glutamate Toxicity in Primary Cultures of Nerve-Muscle Co-Culture Primary Cocultures of Nerve- and Muscle Cells Human muscle is prepared according to a previously described method from portions of biopsy of healthy patient [69]. Muscle cells are established from dissociated cells (10000 cells per wells), plated in gelatin-coated 0.1% on 48 wells plate and grown in a proliferating medium consisting of mix of MEM medium and M199 medium.

Immediately after satellite cells fusion, whole transverse slices of 13-day-old rat Wistar embryos spinal cords with dorsal root ganglia (DRG) attached are placed on the muscle monolayer 1 explant per well (in center area). DRG are necessary to achieve a good ratio of innervations. Innervated cultures are maintained in mix medium. After 24 h in the usual co-culture neuritis are observed growing out of the spinal cord explants. They make contacts with myotubes and induce the first contractions after 8 days. Quickly thereafter, innervated muscle fibres located in proximity to the spinal cord explants, are virtually continuously contracting Innervated fibres are morphologically and spatially distinct from the non-innervated ones and could easily be distinguished from them.

One co-culture is done (6 wells per conditions).

Glutamate Injury

On day 27, co-cultures are incubated with candidate compounds or Riluzole one hour before glutamate intoxication (60 µM) for 20 min. Then, co-cultures are washed and candidate compounds or Riluzole are added for an additional 48 h. After this incubation time, unfixed cocultures are incubated with α-bungarotoxin coupled with Alexa 488 at concentration 500 nmol/L for 15 min at room temperature. Then, cocultures fixed by PFA for 20 min at room temperature. After permeabilization with 0.1% of saponin, co-cultures are incubated with anti-neurofilament antibody (NF).

These antibodies are detected with Alexa Fluor 568 goat anti-mouse IgG (Molecular probe). Nuclei of neurons are labeled by a fluorescent marker (Hoechst solution).

Endpoints are (1) Total neurite length, (2) Number of motor units, (3) Total motor unit area, which are indicative of motor neuron survival and functionality.

For each condition, 2×10 pictures per well are taken using InCell Analyzer™ 1000 (GE Healthcare) with 20× magnification. All the images are taken in the same conditions.

Results

Baclofen and acamprosate combination effectively protects motor neurons and motor units in the coculture model.

b) Combinations Therapies are Efficient in ALS Mouse Model

Experiments are performed on male mice. Transgenic male mice B6SJL-Tg(SOD1)2Gur/J mice and their control (respectively SN2726 and SN2297 from Jackson Laboratories, Ben Harbor, USA and distributed by Charles River in France) are chosen in this set of experiments to mimic ALS.

Diseased mice express the SOD1-G93A transgene, designed with a mutant human SOD1 gene (a single amino acid substitution of glycine to alanine at codon 93) driven by its endogenous human SOD1 promoter. Control mice express the control human SOD1 gene.

Randomisation of the Animals

The group assignation and the randomisation of the animals are based on the body weight; for each group, the randomisation is done one day before the first treatment.

Drug Administration

Mice are dosed with candidate drug treatment diluted in vehicle from $60^{th}$ day after birth till death. Diluted solutions of drug candidates are prepared with water at room temperature just before the beginning of the administration.

In Drinking Water:

Riluzole is added in drinking water at a final concentration of 6 mg/ml (adjusted to each group mean body weight) in 5% cyclodextrin. As a mouse drinks about 5 ml/day, the estimated administrated dose is 30 mg/kg/day which is a dose that was shown to increase the survival of mice.

Cyclodextrin is used as vehicle at the final concentration of 5%, diluted in water at room temperature from stock solution (cyclodextrin 20%).

Oral Administration (Per Os):

Drug combinations are administrated per os, daily.

Cyclodextrin is used as vehicle at the final concentration of 5%, diluted in water at room temperature from stock solution (cyclodextrin 20%).

Clinical Observation

The clinical observation of each mouse is performed daily, from the first day of treatment (60 days of age) until the death (or sacrifice). Clinical observation consists in studying behavioural tests: onset of paralysis, "loss of splay", "loss of righting reflex", and general gait observation:

Onset of paralysis: The observation consists of paralysis observation of each limb. Onset of paralysis corresponds to the day of the first signs of paralysis.

The loss of splay test consists of tremors or shaking notification and the position of hind limb (hanging or splaying out) when the mouse is suspended by the tail.

The loss of righting reflex test evaluates the ability of the mouse to right itself within 30 sec of being turned on either side. The righting reflex is lost when the mouse is unable to right itself. The loss of righting reflex determines the end stage of disease: the mouse unable to right itself is euthanized.

Results-Combinations Therapies are Efficient in ALS In Vivo Model

An improvement of the disease is observed for the diseased animals treated with for the baclofen and acamprosate combination.

3. Protective Effect of Combinations in Oxaliplatin-Induced Neuropathy as an In Vivo Model for Neuropathic Pain.

Combinatorial therapies of the present invention are tested in vivo, in suitable models of peripheral neuropathy, i.e., acute model of oxaliplatin-induced neuropathy and chronic model of oxaliplatin-induced neuropathy. The animals, protocols and results are presented in this section.

Animal Husbandry

Sprague-Dawley rats (CERJ, France), weighing 150-175 g at the beginning of the experimental of the oxaliplatin treatment ($D_0$) are used. Animals are housed in a limited access animal facility in a temperature (19.5° C.-24.5° C.) and relative humidity (45%-65%) controlled room with a 12 h-light/dark cycle, with ad libitum access to standard pelleted laboratory chow and water throughout the study. Animals are housed 4 or 5 per cage and a one week-acclimation period is observed before any testing.

Experimental Design

Five following groups of rats are used in all experiments:

Control Groups:

Group 1: Vehicle of oxaliplatin (distilled water), i.p./Vehicle of candidate combination(s) (distilled water), p.o. daily.

Group 2: oxaliplatin (distilled water), i.p./Vehicle of candidate combination(s) (distilled water), p.o. daily.

Group 3: oxaliplatin 3 mg/kg i.p./single drug in distilled water, p.o. daily×9.

Tested Composition Groups:

Group 4: oxaliplatin 3 mg/kg i.p./candidate combination(s) in distilled water, p.o. daily×9.

Group 5: oxaliplatin 3 mg/kg i.p./Gabapentin (100 mg/kg) in distilled water, p.o. on testing days (i.e. $D_1$ & $D_8$).

Vehicle and test items are delivered daily from D-1 to D7 (the day before the last testing day) whereas gabapentin is administered on testing days (120 minutes before the test).

All treatments are administered in a coded and random order when it is possible. Doses are expressed in terms of free active substance.

Neuropathy Induction:

Acute neuropathy is induced by a single intraperitoneal injection of oxaliplatin (3 mg/kg).

Chronic peripheral neuropathy is induced by repeated intraperitoneal injections of oxaliplatin (3 mg/kg, i.p.) on days 0, 2, 4 and 7 (CD=12 mg/kg, i.p.). Chronic neuropathy in humans is cumulative as well and is most commonly seen in patients who have received total doses of oxaliplatin > or =540 mg/m² which corresponds to ~15 mg/kg as cumulative dose in rats [70].

The oxaliplatin-induced painful neuropathy in rat reproduces the pain symptoms in oxaliplatin-treated patients:

The thermal hyperalgesia is the earliest symptom. It can be measured with the acetone test or with the tail-immersion test;

The mechanical hyperalgesia appears later. It can be quantified with the Von Frey test or the paw pressure test.

Animal Dosing and Testing

All drug combinations are administered from the day before the first intraperitoneal injection of oxaliplatin 3 mg/kg (D-1) and pursued daily orally until D7. During the testing days (i.e. D1 and D7), the drug combinations are administered after the test. Animals from the reference-treated group (gabapentin) are dosed only during the testing days.

Acetone Test

Cold allodynia is assessed using the acetone test by measuring the responses to thermal non-nociceptive stimulation on D1 (around 24 h after the first injection of oxaliplatin 3 mg/kg (acute effect of oxaliplatin), and D8 (chronic effect of oxaliplatin).

In the acetone test, latency of hindpaw withdrawal is measured after application of a drop of acetone to the plantar surface of both hindpaws (reaction time) and the intensity of the response is scored (cold score). Reaction time to the cooling effect of acetone is measured within 20 sec (cut-off) after acetone application. Responses to acetone are also graded to the following 4-point scale: 0 (no response); 1 (quick withdrawal, flick of the paw); 2 (prolonged withdrawal or marked flicking of the paw); 3 (repeated flicking of the paw with licking or biting).

For each experimental group, results are expressed as:

The reaction time defined as the time expressed in sec required to elicit paw reaction (mean of 6 measures for each rat together±SEM).

The cumulative cold score defined as the sum of the 6 scores for each rat together±SEM. The minimum score being 0 (no response to any of the 6 trials) and the maximum possible score being 18 (repeated flicking and licking or biting of paws on each of the six trials).

Statistical Analyses

Student test, unilateral, type 3 is performed. The significance level is set as $p<0.05$; all the groups are compared to the diseased+vehicle group (oxaliplatin treated group). Means and standard error mean are shown on the figures.

Results

Oxaliplatin induced a significant decrease in reaction time of paw withdrawal after acetone application (diseased group+vehicle) during the time course. This decrease is progressive and significant from Day 1 (acute model of oxaliplatin-induced neuropathy) to Day 8 (chronic model) as compared to the vehicle group.

Anti-allodynic effect in acute model and chronic model of oxaliplatin-induced neuropathy: Baclofen and acamprosate combination is tested in both models of oxaliplatin-induced neuropathy. It induces a significant decrease in the cumulative cold score and a significant increase of reaction time as compared to the oxaliplatin-vehicle treated group. In conclusion, this drug combination protects from chronic and acute neuropathy.

REFERENCES

1 Crook R, Verkkoniemi A, Perez-Tur J, Mehta N, Baker M, Houlden H, Farrer M, Hutton M, Lincoln S, Hardy J, Gwinn K, Somer M, Paetau A, Kalimo H, Ylikoski R, Poyhonen M, Kucera S & Haltia M (1998) A variant of Alzheimer's disease with spastic paraparesis and unusual plaques due to deletion of exon 9 of presenilin 1. *Nat. Med.* 4, 452-5.

2 Houlden H, Baker M, McGowan E, Lewis P, Hutton M, Crook R, Wood N W, Kumar-Singh S, Geddes J, Swash M, Scaravilli F, Holton J L, Lashley T, Tomita T, Hashimoto T, Verkkoniemi A, Kalimo H, Somer M, Paetau A, Martin J J, Van Broeckhoven C, Golde T, Hardy J, Haltia M & Revesz T (2000) Variant Alzheimer's disease with spastic paraparesis and cotton wool plaques is caused by PS-1 mutations that lead to exceptionally high amyloid-beta concentrations. *Ann. Neurol.* 48, 806-8.

3 Kwok J B, Taddei K, Hallupp M, Fisher C, Brooks W S, Broe G A, Hardy J, Fulham M J, Nicholson G A, Stell R, St George Hyslop P H, Fraser P E, Kakulas B, Clarnette R, Relkin N, Gandy S E, Schofield P R & Martins R N (1997) Two novel (M233T and R278T) presenilin-1 mutations in early-onset Alzheimer's disease pedigrees and preliminary evidence for association of presenilin-1 mutations with a novel phenotype. *Neuroreport* 8, 1537-42.

4 Verkkoniemi A, Kalimo H, Paetau A, Somer M, Iwatsubo T, Hardy J & Haltia M (2001) Variant Alzheimer disease with spastic paraparesis: neuropathological phenotype. *J. Neuropathol. Exp. Neurol.* 60, 483-92.

5 Citron M (2004) Strategies for disease modification in Alzheimer's disease. *Nat. Rev. Neurosci.* 5, 677-85.

6 Suh Y-H & Checler F (2002) Amyloid precursor protein, presenilins, and alpha-synuclein: molecular pathogenesis and pharmacological applications in Alzheimer's disease. *Pharmacol. Rev.* 54, 469-525.

7 Blacker D, Albert M S, Bassett S S, Go R C, Harrell L E & Folstein M F (1994) Reliability and validity of NINCDS-ADRDA criteria for Alzheimer's disease. The National Institute of Mental Health Genetics Initiative. *Arch. Neurol.* 51, 1198-204.

8 Rossor M N, Fox N C, Freeborough P A & Harvey R J (1996) Clinical features of sporadic and familial Alzheimer's disease. *Neurodegeneration* 5, 393-7.

9 Glenner G G, Wong C W, Quaranta V & Eanes E D (1984) The amyloid deposits in Alzheimer's disease: their nature and pathogenesis. *Appl. Pathol.* 2, 357-69.

10. Ballatore C, Lee V M-Y & Trojanowski J Q (2007) Tau-mediated neurodegeneration in Alzheimer's disease and related disorders. *Nat. Rev. Neurosci.* 8, 663-72.
11. DiLuca M, Bell K F S & Claudio Cuello A (2006) Altered synaptic function in Alzheimer's disease. *Eur. J. Pharmacol.* 545, 11-21.
12. Hardy J A & Higgins G A (1992) Alzheimer's disease: the amyloid cascade hypothesis. *Science* 256, 184-5.
13. Braak H & Braak E (1991) Neuropathological stageing of Alzheimer-related changes. *Acta Neuropathol.* 82, 239-59.
14. Golde T E (2005) The Abeta hypothesis: leading us to rationally-designed therapeutic strategies for the treatment or prevention of Alzheimer disease. *Brain Pathol.* 15, 84-7.
15. Hardy J & Selkoe D J (2002) The amyloid hypothesis of Alzheimer's disease: progress and problems on the road to therapeutics. *Science* 297, 353-6.
16. Selkoe D J (2000) The genetics and molecular pathology of Alzheimer's disease: roles of amyloid and the presenilins. *Neurol. Clin.* 18, 903-22.
17. Zlokovic B V (2008) The blood-brain barrier in health and chronic neurodegenerative disorders. *Neuron* 57, 178-201.
18. Budd Haeberlein S L & Lipton S A (2009) Excitotoxicity in neurodegenerative disease. In *Encyclopedia of neuroscience* (Squire L R, ed), pp. 77-86. Elsevier.
19. Hughes J R (2009) Alcohol withdrawal seizures. *Epilepsy Behav.* 15, 92-7.
20. Kim A H, Kerchner G A & Choi D W (2002) *CNS Neuroprotection* (F. W. Marcoux and D. W. Choi, eds.) Springer Berlin Heidelberg, Berlin, Heidelberg.
21. Hama A & Sagen J (2011) Antinociceptive effect of riluzole in rats with neuropathic spinal cord injury pain. *J. Neurotrauma* 28, 127-34.
22. McGleenon B M, Dynan K B & Passmore A P (1999) Acetylcholinesterase inhibitors in Alzheimer's disease. *Br. J. Clin. Pharmacol.* 48, 471-480.
23. Parsons C G, Danysz W & Quack G (1999) Memantine is a clinically well tolerated N-methyl-D-aspartate (NMDA) receptor antagonist—a review of preclinical data. *Neuropharmacology* 38, 735-67.
24. Malgouris C, Bardot F, Daniel M, Pellis F, Rataud J, Uzan A, Blanchard J C & Laduron P M (1989) Riluzole, a novel antiglutamate, prevents memory loss and hippocampal neuronal damage in ischemic gerbils. *J. Neurosci.* 9, 3720-7.
25. Wahl F, Allix M, Plotkine M & Boulu R G (1993) Effect of riluzole on focal cerebral ischemia in rats. *Eur. J. Pharmacol.* 230, 209-14.
26. Wahl F, Renou E, Mary V & Stutzmann J M (1997) Riluzole reduces brain lesions and improves neurological function in rats after a traumatic brain injury. *Brain Res.* 756, 247-55.
27. Ettmayer P, Amidon G L, Clement B & Testa B (2004) Lessons learned from marketed and investigational prodrugs. *J. Med. Chem.* 47, 2393-404.
28. Beaumont K, Webster R, Gardner I & Dack K (2003) Design of ester prodrugs to enhance oral absorption of poorly permeable compounds: challenges to the discovery scientist. *Curr. Drug Metab.* 4, 461-85.
29. Heimbach T, Oh D M, Li L Y, Rodriguez-Hornedo N, Garcia G & Fleisher D (2003) Enzyme-mediated precipitation of parent drugs from their phosphate prodrugs. *Int. J. Pharm.* 261, 81-92.
30. Yang C Y, Dantzig A H & Pidgeon C (1999) Intestinal peptide transport systems and oral drug availability. *Pharm. Res.* 16, 1331-43.
31. Steffansen B, Nielsen C U, Brodin B, Eriksson A H, Andersen R & Frokjaer S (2004) Intestinal solute carriers: an overview of trends and strategies for improving oral drug absorption. *Eur. J. Pharm. Sci.* 21, 3-16.
32. Stella V J (2007) *Prodrugs: challenges and rewards*. (A. Press and Springer, eds.) Springer Singapore Pte. Limited, New-York.
33. Wermuth C G (2003) Designing prodrugs and bioprecursors. In *The Practice of Medicinal Chemistry* (Hardbound, ed), 2nd ed., pp. 561-585. Academic Press.
34. Pezron I, Mitra A K, Duvvuri S & Tirucherai G S (2002) Prodrug strategies in nasal drug delivery. *Expert Opin. Ther. Pat.* 12, 331-340.
35. Stella V J (2004) Prodrugs as therapeutics. *Expert Opin. Ther. Pat.* 14, 277-280.
36. Stella V J & Nti-Addae K W (2007) Prodrug strategies to overcome poor water solubility. *Adv. Drug Deliv. Rev.* 59, 677-94.
37. Higuchi T & Stella V J (1975) *Pro-drugs as Novel Drug Delivery System*, ACS Sympos American Chemical Society, Washington, D.C.
38. Roche E B (1977) Design of biopharmaceutical properties through prodrugs and analogs: a symposium, American P The Academy, Washington, D.C.
39. Lal R, Sukbuntherng J, Tai E H L, Upadhyay S, Yao F, Warren M S, Luo W, Bu L, Nguyen S, Zamora J, Peng G, Dias T, Bao Y, Ludwikow M, Phan T, Scheuerman R A, Yan H, Gao M, Wu Q Q, Annamalai T, Raillard S P, Koller K, Gallop M A & Cundy K C (2009) Arbaclofen placarbil, a novel R-baclofen prodrug: improved absorption, distribution, metabolism, and elimination properties compared with R-baclofen. *J. Pharmacol. Exp. Ther.* 330, 911-21.
40. Xu F, Peng G, Phan T, Dilip U, Chen J L, Chernov-Rogan T, Zhang X, Grindstaff K, Annamalai T, Koller K, Gallop M A & Wustrow D J (2011) Discovery of a novel potent GABA(B) receptor agonist. *Bioorg. Med. Chem. Lett.* 21, 6582-5.
41. Leach A R & Gillet V J *An Introduction to Chemoinformatics* (Springer-Verlag New York Inc, ed.).
42. Rahman S A, Bashton M, Holliday G L, Schrader R & Thornton J M (2009) Small Molecule Subgraph Detector (SMSD) toolkit. *J. Cheminform.* 1, 12.
43. Stahl H & Wermuth C G (2011) Pharmaceutical salts: Properties, selection, and use, 2nd ed. (Wiley-VCH, ed.).
44. Hanafi R, Mosad S, Abouzid K, Niess R & Spahn-Langguth H (2011) Baclofen ester and carbamate prodrug candidates: a simultaneous chromatographic assay, resolution optimized with DryLab. *J. Pharm. Biomed. Anal.* 56, 569-76.
45. Raboisson P, Breitholtz-Emanuelsson A, Dahlöf H, Edwards L, Heaton W L, Isaac M, Jarvie K, Kers A, Minidis A B E, Nordmark A, Sheehan S M, Slassi A, Strom P, Terelius Y, Wensbo D, Wilson J M, Xin T & McLeod D A (2012) Discovery and characterization of AZD9272 and AZD6538-Two novel mGluR5 negative allosteric modulators selected for clinical development. *Bioorg. Med. Chem. Lett.* 22, 6974-9.
46. Suzuki G, Kimura T, Satow A, Kaneko N, Fukuda J, Hikichi H, Sakai N, Maehara S, Kawagoe-Takaki H, Hata M, Azuma T, Ito S, Kawamoto H & Ohta H (2007) Pharmacological characterization of a new, orally active and potent allosteric metabotropic glutamate receptor 1 antagonist, 4-[1-(2-fluoropyridin-3-yl)-5-methyl-1H-1,2,3-triazol-4-yl]-N-isopropyl-N-methyl-3,6-dihydropyridine-1(2H)-carboxamide (FTIDC). *J. Pharmacol. Exp. Ther.* 321, 1144-53.

47 Kohara A, Nagakura Y, Kiso T, Toya T, Watabiki T, Tamura S, Shitaka Y, Itahana H & Okada M (2007) Antinociceptive profile of a selective metabotropic glutamate receptor 1 antagonist YM-230888 in chronic pain rodent models. *Eur. J. Pharmacol.* 571, 8-16.

48 Dekundy A, Gravius A, Hechenberger M, Pietraszek M, Nagel J, Tober C, van der Elst M, Mela F, Parsons C G & Danysz W (2011) Pharmacological characterization of MRZ-8676, a novel negative allosteric modulator of subtype 5 metabotropic glutamate receptors (mGluR5): focus on L: -DOPA-induced dyskinesia. *J. Neural Transm.* 118, 1703-16.

49 Goeldner C, Ballard T M, Knoflach F, Wichmann J, Gatti S & Umbricht D (2013) Cognitive impairment in major depression and the mGlu2 receptor as a therapeutic target. *Neuropharmacology* 64, 337-46.

50 Jaeschke G, Wettstein J G, Nordquist R E & Spooren W (2008) mGlu5 receptor antagonists and their therapeutic potential. *Expert Opin. Ther. Pat.* 18, 123-142.

51 Carroll F I (2008) Antagonists at metabotropic glutamate receptor subtype 5: structure activity relationships and therapeutic potential for addiction. *Ann. N. Y Acad. Sci.* 1141, 221-32.

52 Emmitte K A (2013) mGlu5 negative allosteric modulators: a patent review (2010-2012). *Expert Opin. Ther. Pat.* 23, 393-408.

53 Froestl W, Muhs A & Pfeifer A (2012) Cognitive enhancers (nootropics). Part 1: drugs interacting with receptors. *J. Alzheimers. Dis.* 32, 793-887.

54 Hemstapat K, Da Costa H, Nong Y, Brady A E, Luo Q, Niswender C M, Tamagnan G D & Conn P J (2007) A novel family of potent negative allosteric modulators of group II metabotropic glutamate receptors. *J. Pharmacol. Exp. Ther.* 322, 254-64.

55 Maksay G, Nemes P, Vincze Z & Bíró T (2008) Synthesis of (nor)tropeine (di)esters and allosteric modulation of glycine receptor binding. *Bioorg. Med. Chem.* 16, 2086-92.

56 Yevenes G E & Zeilhofer H U (2011) Allosteric modulation of glycine receptors. *Br. J. Pharmacol.* 164, 224-36.

57 Paris D, Ait-Ghezala G, Mathura V S, Patel N, Quadros A, Laporte V & Mullan M (2005) Anti-angiogenic activity of the mutant Dutch A(beta) peptide on human brain microvascular endothelial cells. *Brain Res. Mol. Brain Res.* 136, 212-30.

58 Singer C A, Figueroa-Masot X A, Batchelor R H & Dorsa D M (1999) The mitogen-activated protein kinase pathway mediates estrogen neuroprotection after glutamate toxicity in primary cortical neurons. *J. Neurosci.* 19, 2455-63.

59 Harrison N L (1990) On the presynaptic action of baclofen at inhibitory synapses between cultured rat hippocampal neurones. *J. Physiol.* 422, 433-46.

60 LOEWE S (1953) The problem of synergism and antagonism of combined drugs. *Arzneimittelforschung.* 3, 285-90.

61 Grabovsky Y & Tallarida R J (2004) Isobolographic analysis for combinations of a full and partial agonist: curved isoboles. *J. Pharmacol. Exp. Ther.* 310, 981-6.

62 BLISS C I (1939) THE TOXICITY OF POISONS APPLIED JOINTLY1. *Ann. Appl. Biol.* 26, 585-615.

63 Meunier J, Ieni J & Maurice T (2006) The anti-amnesic and neuroprotective effects of donepezil against amyloid beta25-35 peptide-induced toxicity in mice involve an interaction with the sigma1 receptor. *Br. J. Pharmacol.* 149, 998-1012.

64 Snyder P J, Bednar M M, Cromer J R & Maruff P (2005) Reversal of scopolamine-induced deficits with a single dose of donepezil, an acetylcholinesterase inhibitor. *Alzheimers. Dement.* 1, 126-35.

65 Folstein M F, Folstein S E & McHugh P R (1975) "Mini-mental state". A practical method for grading the cognitive state of patients for the clinician. *J. Psychiatr. Res.* 12, 189-98.

66 Gool W A van (2000) Het effect van rivastigmine bij de ziekte van Alzheimer: houdt rivastigmine het alledaagse gewoon ? *Geneesmiddelenbulletin* 34, 17-22.

67 Barnes C A Aging and the physiology of spatial memory. *Neurobiol. Aging* 9, 563-8.

68 Dember W N & Fowler H (1958) Spontaneous alternation behavior. *Psychol. Bull.* 55, 412-28.

69 Braun S, Croizat B, Lagrange M C, Warter J M & Poindron P (1996) Neurotrophins increase motoneurons' ability to innervate skeletal muscle fibers in rat spinal cord-human muscle cocultures. *J. Neurol. Sci.* 136, 17-23.

70 Cersosimo R J (2005) Oxaliplatin-associated neuropathy: a review. *Ann. Pharmacother.* 39, 128-35.

We claim:

1. A method of treating Alzheimer's disease or a related disease selected from senile dementia of AD type (SDAT), frontotemporal dementia (FTD), mild cognitive impairment (MCI) and age-associated memory impairment (AAMI), comprising administering twice daily to a subject in need thereof from 0.4 to 50 mg of acamprosate and from 6 to 15 mg of baclofen, or pharmaceutically acceptable salts thereof.

2. The method of claim 1, wherein baclofen and acamprosate compounds are mixed with a pharmaceutically acceptable carrier or excipient.

3. The method of claim 1, wherein baclofen and acamprosate are formulated or administered together, separately or sequentially.

4. The method of claim 1, wherein baclofen and acamprosate are administered repeatedly to the subject.

5. The method of claim 1, wherein baclofen and acamprosate are administered in an amount effective to protect neuronal and endothelial functions from Aβ toxicity.

6. The method of claim 1, comprising administering 1 mg acamprosate and 15 mg baclofen, twice daily.

7. The method of claim 1, comprising administering 20 mg acamprosate and 12 mg baclofen, twice daily.

8. The method of claim 1, comprising administering 40 mg acamprosate and 12 mg baclofen, twice daily.

9. The method of claim 1, further comprising administering donepezil, galantamine, rivastigmine, or memantine or pharmaceutically acceptable salts thereof.

10. The method of claim 1, further comprising administering 0.6 mg donepezil, twice daily.

11. The method of claim 1, comprising administering 20 mg acamprosate, 12 mg baclofen and 0.6 mg donepezil, twice daily.

12. The method of claim 1, comprising administering 40 mg acamprosate, 12 mg baclofen and 0.6 mg donepezil, twice daily.

13. The method of claim 1, wherein the subject is a human subject.

14. The method of claim 1, wherein the subject is a human subject suffering from AD.

15. The method of claim 1, wherein the subject is a human subject suffering from AAMI.

16. The method of claim 1, wherein the subject is a human subject suffering from FTD.

17. A method for correcting or treating cognitive impairment in a subject suffering from Alzheimer's disease, the method comprising administering twice daily to said subject from 0.4 to 50 mg of acamprosate and from 6 to 15 mg of baclofen, or pharmaceutically acceptable salts thereof.

18. A method for correcting or treating memory impairment in a subject suffering from Alzheimer's disease, the method comprising administering twice daily to said subject from 0.4 to 50 mg of acamprosate and from 6 to 15 mg of baclofen, or pharmaceutically acceptable salts thereof.

19. The method of claim 17, wherein baclofen and acamprosate compounds are mixed with a pharmaceutically acceptable carrier or excipient.

20. The method of claim 17, wherein baclofen and acamprosate are formulated or administered together, separately or sequentially.

21. The method of claim 17, wherein baclofen and acamprosate are administered repeatedly to the subject.

22. The method of claim 17, wherein baclofen and acamprosate are administered in an amount effective to protect neuronal and endothelial functions from Aβ toxicity.

23. The method of claim 17, comprising administering 1 mg acamprosate and 15 mg baclofen, twice daily.

24. The method of claim 17, comprising administering 20 mg acamprosate and 12 mg baclofen, twice daily.

25. The method of claim 17, comprising administering 40 mg acamprosate and 12 mg baclofen, twice daily.

26. The method of claim 17, further comprising administering donepezil, galantamine, rivastigmine, or memantine or pharmaceutically acceptable salts thereof.

27. The method of claim 17, further comprising administering 0.6 mg donepezil, twice daily.

28. The method of claim 17, comprising administering 20 mg acamprosate, 12 mg baclofen and 0.6 mg donepezil, twice daily.

29. The method of claim 17, comprising administering 40 mg acamprosate, 12 mg baclofen and 0.6 mg donepezil, twice daily.

30. The method of claim 17, wherein the subject is a human subject.

31. The method of claim 18, wherein baclofen and acamprosate compounds are mixed with a pharmaceutically acceptable carrier or excipient.

32. The method of claim 18, wherein baclofen and acamprosate are formulated or administered together, separately or sequentially.

33. The method of claim 18, wherein baclofen and acamprosate are administered repeatedly to the subject.

34. The method of claim 18, wherein baclofen and acamprosate are administered in an amount effective to protect neuronal and endothelial functions from Aβ toxicity.

35. The method of claim 18, comprising administering 1 mg acamprosate and 15 mg baclofen, twice daily.

36. The method of claim 18, comprising administering 20 mg acamprosate and 12 mg baclofen, twice daily.

37. The method of claim 18, comprising administering 40 mg acamprosate and 12 mg baclofen, twice daily.

38. The method of claim 18, further comprising administering donepezil, galantamine, rivastigmine, or memantine or pharmaceutically acceptable salts thereof.

39. The method of claim 18, further comprising administering 0.6 mg donepezil, twice daily.

40. The method of claim 18, comprising administering 20 mg acamprosate, 12 mg baclofen and 0.6 mg donepezil, twice daily.

41. The method of claim 18, comprising administering 40 mg acamprosate, 12 mg baclofen and 0.6 mg donepezil, twice daily.

42. The method of claim 18, wherein the subject is a human subject.

* * * * *

UNITED STATES PATENT AND TRADEMARK OFFICE
CERTIFICATE OF CORRECTION

PATENT NO. : 9,144,558 B2  Page 1 of 1
APPLICATION NO. : 14/479614
DATED : September 29, 2015
INVENTOR(S) : Daniel Cohen et al.

It is certified that error appears in the above-identified patent and that said Letters Patent is hereby corrected as shown below:

In the Specification

Column 3,
Line 43, "AB peptide" should read --Aβ peptide--.

Column 6,
Line 51, "A ◊ $_{25\text{-}35}$" should read --Aβ$_{25\text{-}35}$--.

Column 8,
Line 60, " ⌠⌡ : " should read -- ᴏᴏᴏ : --.

Column 22,
Line 48, "R00711401" should read --RO0711401--.
Line 60, "R00711401" should read --RO0711401--.

Column 23,
Lines 22-23, "R04432717, R04491533" should read --RO4432717, RO4491533--.

Column 37,
Line 63, "55798" should read --S5798--.

Column 45,
Line 28, "staining" should read --staining.--.

Signed and Sealed this
Twenty-sixth Day of April, 2016

Michelle K. Lee
*Director of the United States Patent and Trademark Office*

SEQUENCE LISTING

```
<160> NUMBER OF SEQ ID NOS: 1

<210> SEQ ID NO 1
<211> LENGTH: 21
<212> TYPE: PRT
<213> ORGANISM: Artificial sequence
<220> FEATURE:
<223> OTHER INFORMATION: myelin-oligodendrocyte glycoprotein

<400> SEQUENCE: 1

Met Glu Val Gly Trp Tyr Arg Ser Pro Phe Ser Arg Val Val His Leu
1               5                   10                  15

Tyr Arg Asn Gly Lys
                20
```